(12) United States Patent
Koltun et al.

(10) Patent No.: US 8,324,231 B2
(45) Date of Patent: Dec. 4, 2012

(54) PYRIMIDINONES AS CASEIN KINASE II (CK2) MODULATORS

(75) Inventors: Elena S. Koltun, Foster City, CA (US); Patrick Kearney, San Francisco, CA (US); Naing Aay, San Mateo, CA (US); Arlyn Arcalas, South San Francisco, CA (US); Wai Ki Vicky Chan, San Francisco, CA (US); Jeffry Kimo Curtis, San Anselmo, CA (US); Hongwang Du, Millbrae, CA (US); Ping Huang, Mountain View, CA (US); Brian Kane, Lynchburg, VA (US); Moon Hwan Kim, Palo Alto, CA (US); Michael Pack, San Francisco, CA (US); Amy L. Tsuhako, Milpitas, CA (US); Wei Xu, Danville, CA (US); Cristiana A. Zaharia, Redwood City, CA (US); Peiwen Zhou, Palo Alto, CA (US)

(73) Assignee: Exelixis, Inc., South San Francisco, CA (US)

( * ) Notice: Subject to any disclaimer, the term of this patent is extended or adjusted under 35 U.S.C. 154(b) by 182 days.

(21) Appl. No.: 12/597,271

(22) PCT Filed: Apr. 24, 2008

(86) PCT No.: PCT/US2008/005419
§ 371 (c)(1),
(2), (4) Date: Jan. 21, 2010

(87) PCT Pub. No.: WO2008/143759
PCT Pub. Date: Nov. 27, 2008

(65) Prior Publication Data
US 2010/0144770 A1    Jun. 10, 2010

Related U.S. Application Data

(60) Provisional application No. 60/926,358, filed on Apr. 25, 2007.

(51) Int. Cl.
*A01N 43/54* (2006.01)
*A61K 31/505* (2006.01)
(52) U.S. Cl. ......... 514/272; 544/315; 544/316; 544/318
(58) Field of Classification Search .................. 544/315, 544/316
See application file for complete search history.

(56) References Cited

U.S. PATENT DOCUMENTS

| | | | |
|---|---|---|---|
| 3,950,526 A | 4/1976 | Inaba et al. | |
| 6,964,968 B2 | 11/2005 | Giles et al. | |
| 8,101,625 B2 * | 1/2012 | Rice et al. | 514/274 |
| 2007/0293491 A1 * | 12/2007 | Shafer et al. | 514/234.5 |
| 2009/0215803 A1 * | 8/2009 | Rice et al. | 514/274 |
| 2010/0135954 A1 * | 6/2010 | Tsuhako et al. | 424/85.2 |

FOREIGN PATENT DOCUMENTS

| | | |
|---|---|---|
| GB | 1317338 A | 5/1973 |
| WO | 2007/048065 A | 4/2007 |
| WO | 2007/124288 A | 11/2007 |

OTHER PUBLICATIONS

S.B. Kale et al., Journal of Heterocyclic Chemistry, 44, 289-301 (2007).*
N.B. Hamdy, Egyptian Journal of Chemistry, 48(6), 749-758 (2005).*
K. Singh et al., Indian Journal of Heterocyclic Chemistry,14(4), 319-322 (2005).*
F.H. Al-Hajjar et al., Canadian Journal of Chemistry, 57(20), 2734-42 (1979).*
Shafer et al., Bioorganic & Medicinal Chemistry Letters, 18(16), 4482-4485 (2008).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
N.F. Smith et al., Molecular Cancer Therapeutics, 6, 428-440 (2007).*
Pasha et al., "Synthesis and antimicrobial screening of some pyrimidine derivatives", Indian Journal of Heterocyclic Chemistry, 2005, CAS: 145:397448, 1 page.
Thakar et al., "Synthesis of some pyrimidine derivatives", Journal of the Indian Chemical Society, 1983, CAS: 100:121000, 3 pages.
Andotra, et al., "Synthesis of N-benzylidene 4-substituted aryl-6-(2,4-dialkoxyphenyl)-2-pyrimido-hydrazines", Indin Journal of Heterocyclic Chemistry, 2002, CAS: 138:170177, 3 pages.
Fujisawa et al., "Pyrimidine derivatives", Japan Kokai Tokkyo Koho, 1985, CAS: 102:95665, 2 pages.
Bhat, et al., "Synthesis and in-vitro antimicrobial activity of 4,6-disubstituted pyrimidines", Pharmacy and Pharmacology Communications, 2000, CAS: 134:280800, 1 page.

(Continued)

*Primary Examiner* — James O Wilson
*Assistant Examiner* — Alexander R Pagano
(74) *Attorney, Agent, or Firm* — McDonnell Boehnen Hulbert & Berghoff LLP

(57) ABSTRACT

A compound having Formula I: or a pharmaceutically acceptable salt thereof, wherein X, R, R and R are as defined in the specification; pharmaceutical compositions thereof; and methods of use thereof. The compounds of Formula I are inhibitors of Casein kinase II (CK2) pathways.

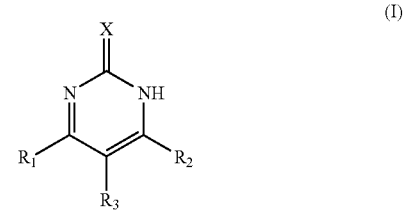

(I)

10 Claims, No Drawings

OTHER PUBLICATIONS

El-Gawad et al., "Synthesis, antimicrobial and antifungal activities of some pyrimidine derivatives", Bulletin of the Faculty of Pharmacy, 1999, CAS: 132:166201, 1 page.

Amine, M. S., "Utiliies of 4-(4"-Benzylphenyl)-6-arylpyrimidine-2-thiones for the synthesis of biologically active condensed and non-condensed heterocycles", Egyptian Journal of Chemistry, 1998, CAS: 130:311755, 1 page.

Wasfy et al., "Synthesis and reactions of 6(4)-(p-benzylphenyl)-4(6)-phenylpyrimidine-2(1H)-thione", Heterocyclic Communications, 1996, CAS: 125:300936, 1 page.

Sarno et al., "Development and exploitation of CK2 inhibitors", Molecular and Cellular Biochemistry, 274(1-2), 2005, 69-76.

Kale et al., "Synthesis and characterization of some important indazolyl derivatives", Journal of Heterocyclic Chemistry, 44(2), 2007, 289-301.

Harinadha et al., "Synthesis antitumor and antibacterial activities of certain substituted pyrimidines bearing benzofuran", Indian Journal of Pharmaceutical Sciences, 2004, 66(5), 647-652.

Singh et al., "Synthesis and fungicidal activity of benzofuran incorporated substituted pyrimidines", Indian Journal of Heterocyclic Chemistry, 2005, 14(4), 319-322.

Bhendkar et al., "Synthesis and antimicrobial activity of 2-amino-4-(2"-furyl)-6-(substituted phenyl)-pyrimidine and its pyrimidinone derivatives", Oriental Journal of Chemistry, 2003, 19(3), 731-732.

Barot, "Synthesis and antibacterial activity of some new 2-aminopyrimidines and 2(1H)-pyrimidinones", Asian Journal of Chemistry, 1996, 8(4), 802-804.

Al-Hajjar et al., "Synthesis and spectroscopic studies of the pyrimidine-2(1H)thione derivatives", Canadian Journal of Chemistry, 1979, 57(20), 2734-42.

* cited by examiner

PYRIMIDINONES AS CASEIN KINASE II (CK2) MODULATORS

This application is a US national phase of International Application No. PCT/US2008/005419 filed on Apr. 24, 2005, which claims the benefit of priority of US Provisional Application No. 60/926,358 filed on Apr. 25, 2007.

BACKGROUND OF THE INVENTION

1. Field of the Invention

This invention relates to the field of protein kinases and inhibitors thereof. In particular, the invention relates to inhibitors of Casein kinase II (CK2) pathways.

2. Summary of the Related Art

Casein kinase II (CK2) is a highly conserved, ubiquitously expressed protein serine/threonine kinase that phosphorylates acidic proteins such as casein. It has a tetrameric $\alpha(2)/\beta(2)$ structure. The alpha subunit possesses catalytic activity, and the beta subunit is autophosphorylated in vitro. While consideration of CK2 as a tetrameric complex remains relevant, significant evidence has emerged to challenge the view that its individual subunits exist exclusively within these complexes (Bibby et al (2005) Int J Biol Sci. 1:67-79). Circumscribed as having a vast array of substrates located in a number of cellular compartments, CK2 has been implicated in critical cellular processes such as proliferation, apoptosis, differentiation, and transformation (Olsten et al (2004) Biochem Cell Biol. 82:681-93).

Thus, there is a need for novel compounds that specifically inhibit, regulate and/or modulate kinases, particularly Casein kinase II (CK2), in order to treat, prevent, and/or inhibit diseases and conditions that involve critical cellular processes such as proliferation, apoptosis, differentiation, and transformation, such as cancers.

SUMMARY OF THE INVENTION

The invention relates to compounds and pharmaceutical compositions of the compounds for inhibiting CK2.

One aspect of the invention relates to compounds that inhibit CK2 function. The compounds are exemplified by Formula I as described herein.

Another aspect of the invention relates to a pharmaceutical composition comprising a compound according Formula I and a pharmaceutically acceptable carrier, excipient, or diluent.

Another aspect of the invention relates to a method of inhibiting CK2 in a cell, comprising contacting the cell, in which inhibition of CK2 is desired, with a compound according to Formula I.

Another aspect of the invention relates to a method of inhibiting CK2 in a cell, comprising contacting a cell in which inhibition of CK2 is desired with a pharmaceutical composition comprising a compound according to Formula I and a pharmaceutically acceptable carrier, excipient, or diluent.

Another aspect of the invention relates to a method of treating a disease or condition that involves CK2 comprising administering to a patient, in need of said treatment, a compound according to Formula I.

Another aspect of the invention relates to a method of treating a disease or condition that involves CK2 comprising administering to a patient, in need of said treatment, a pharmaceutical composition comprising a compound according to Formula I and a pharmaceutically acceptable carrier, excipient, or diluent.

The disease or condition that can be treated by the compounds of Formula I, and the pharmaceutical compositions thereof, include cancer. Non-limiting examples of the types of cancer that can be treated include ovarian cancer, cervical cancer, breast cancer, colorectal cancer, or glioblastomas.

There are many different aspects of the compounds, pharmaceutical compositions thereof, and methods of use thereof, as described hereinbelow, and each aspect is non-limiting in regard to the scope of the invention. The transitional term "comprising" as used herein, which is synonymous with "including," "containing," or "characterized by," is inclusive or open-ended and does not exclude additional, unrecited elements or method steps.

The foregoing only summarizes certain aspects of the invention and is not intended to be limiting in nature. These aspects and other aspects and embodiments are described more fully below.

DETAILED DESCRIPTION OF THE INVENTION

The first aspect of the invention relates to compounds of Formula I:

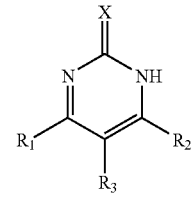

or a pharmaceutically acceptable salt thereof, wherein:
X is O or S;
$R_1$ is —$(C_6$-$C_{10})$aryl substituted with 1, 2 or 3 groups independently selected from —O$(C_1$-$C_6)$alkyl-$R_4$, —N(H)$(C_1$-$C_6)$alkyl-$R_5$, —N[$(C_1$-$C_6)$alkyl]$(C_1$-$C_6)$alkyl-$R_6$, —O$(C_1$-$C_6)$alkenyl-$R_7$, —O$(C_1$-$C_6)$alkynyl-$R_8$, —OH, —OCF$_3$, —$(C_1$-$C_6)$alkyl and halo;
$R_2$ is benzodioxolyl, benzofuranyl, imidazolyl, 1,2-dihydro-2H-benzimidizol-2-one, 1,3-dihydro-2H-benzimidizol-2-one, thiazolyl, pyridinyl, indazolyl, furanyl, or benzisoxazolyl, wherein each of said benzodioxolyl, benzofuranyl, imidazolyl, 1,2-dihydro-2H-benzimidizol-2-one, 1,3-dihydro-2H-benzimidizol-2-one, thiazolyl, pyridinyl, indazolyl, furanyl, or benzisoxazolyl is optionally substituted with 1, 2 or 3 groups, which can be the same or different, selected from —N(H)$(C_1$-$C_6)$alkyl-N(H)C(O)—$(C_1$-$C_6)$alkyl-N[$(C_1$-$C_6)$alkyl]$_2$, —N(H)$(C_1$-$C_6)$alkyl-$R_9$, —$(C_1$-$C_6)$alkyl, —N[$(C_1$-$C_6)$alkyl]$(C_1$-$C_6)$alkyl-$R_{10}$, —N(H)C(O)$(C_1$-$C_6)$alkyl-N[$(C_1$-$C_6)$alkyl]$_2$, —O—$(C_1$-$C_6)$alkyl, —NH$_2$, —N(H)$(C_1$-$C_6)$alkyl-N[$(C_1$-$C_6)$alkyl]$_2$, —N(H)C(O)—$(C_1$-$C_6)$alkyl, phenyl optionally substituted with halo, —N(H)$(C_1$-$C_6)$alkyl-$(C_6$-$C_{10})$aryl optionally substituted with halo or alkoxy at any ring position, and —N(H)$(C_1$-$C_6)$alkyl-NH$_2$;
$R_3$ is H;
or $R_1$ and $R_3$ can join to form a ring of 5-6 carbon atoms;
or $R_1$ is —$(C_6$-$C_{10})$aryl and $R_2$ is indazolyl substituted with 1, 2 or 3 groups, which can be the same or different, selected from —N(H)$(C_1$-$C_6)$alkyl-N(H)C(O)—$(C_1$-$C_6)$alkyl-N[$(C_1$-$C_6)$alkyl]$_2$, —N(H)$(C_1$-$C_6)$alkyl-$R_9$, —$(C_1$-$C_6)$alkyl, —N[$(C_1$-$C_6)$alkyl]$(C_1$-$C_6)$alkyl-$R_{10}$, —N(H)C(O)$(C_1$-$C_6)$alkyl-N[$(C_1$-$C_6)$alkyl]$_2$, —O—$(C_1$-$C_6)$alkyl, —NH$_2$, —N(H)C(O)—$(C_1$-$C_6)$alkyl, phenyl optionally substituted with halo, —N(H)(C$_1$-C$_6$)alkyl-(C$_6$-C$_{10}$)aryl optionally substituted with halo or alkoxy at any ring position, and —N(H)(C$_1$-C$_6$)alkyl-NH$_2$;

wherein each of R$_4$, R$_5$, R$_6$, R$_7$, R$_8$, R$_9$, and R$_{10}$ are independently selected from H, —OH, halo, —CF$_3$, —O(C$_1$-C$_6$) alkyl, —(C$_6$-C$_{10}$)aryl optionally substituted with halo or alkoxy, —O—(C$_1$-C$_6$)alkyl-(C$_6$-C$_{10}$)aryl, —(C$_3$-C$_{10}$)cycloalkyl, —CN, -(5-10 membered)heteroaryl, -(4-10 membered)heterocycloalkyl, —NH$_2$, —N(H)(C$_1$-C$_6$)alkyl, and —N(H)[(C$_1$-C$_6$)alkyl]$_2$.

In another embodiment of Formula I, or a pharmaceutically acceptable salt thereof, R$_2$ is benzodioxolyl, benzofuranyl, imidazolyl, 1,2-dihydro-2H-benzimidizol-2-one, 1,3-dihydro-2H-benzimidizol-2-one, thiazolyl, indazolyl, furanyl, or benzisoxazolyl, wherein each of said benzodioxolyl, benzofuranyl, imidazolyl, 1,2-dihydro-2H-benzimidizol-2-one, 1,3-dihydro-2H-benzimidizol-2-one, thiazolyl, indazolyl, furanyl, or benzisoxazolyl is optionally substituted with 1, 2 or 3 groups, which can be the same or different, selected from —N(H)(C$_1$-C$_6$)alkyl-N(H)C(O)—(C$_1$-C$_6$)alkyl-N[(C$_1$-C$_6$)alkyl]$_2$, —N(H)(C$_1$-C$_6$)alkyl-R$_9$, —(C$_1$-C$_6$)alkyl, —N[(C$_1$-C$_6$)alkyl](C$_1$-C$_6$)alkyl-R$_{10}$, —N(H)C(O)(C$_1$-C$_6$)alkyl-N[(C$_1$-C$_6$)alkyl]$_2$, —O—(C$_1$-C$_6$)alkyl, —NH$_2$, —N(H)(C$_1$-C$_6$)alkyl-N([C$_1$-C$_6$)alkyl]$_2$, —N(H)C(O)—(C$_1$-C$_6$)alkyl, phenyl optionally substituted with halo, —N(H)(C$_1$-C$_6$)alkyl-(C$_6$-C$_{10}$)aryl optionally substituted with halo or alkoxy at any ring position, and —N(H)(C$_1$-C$_6$)alkyl-NH$_2$.

In another embodiment of Formula I, or a pharmaceutically acceptable salt thereof, X is O.

In another embodiment of Formula I, or a pharmaceutically acceptable salt thereof, R$_3$ is H.

Throughout this disclosure, if there is a phrase, immediately after a chemical group, stating that this preceding group can be optionally substituted at any ring position, this is meant to mean that any hydrogen atom off of any atom of this ring can be replaced by any of these optional substituents. For example, when —N(H)(C$_1$-C$_6$)alkyl-(C$_6$-C$_{10}$)aryl can be optionally substituted with halo or alkoxy at any ring position, this means that any hydrogen atom of the —(C$_6$-C$_{10}$)aryl portion of —N(H)(C$_1$-C$_6$)alkyl-(C$_6$-C$_{10}$)aryl can be optionally substituted with halo or alkoxy.

In another embodiment of Formula I, or a pharmaceutically acceptable salt thereof, R$_1$ is phenyl substituted with 1, 2 or 3 groups independently selected from —O(C$_1$-C$_6$)alkyl-R$_4$, —N(H)(C$_1$-C$_6$)alkyl —R$_5$, —N[(C$_1$-C$_6$)alkyl](C$_1$-C$_6$)alkyl-R$_6$, —O(C$_1$-C$_6$)alkenyl-R$_7$, —O(C$_1$-C$_6$)alkynyl-R$_8$, —OH, —OCF$_3$, —(C$_1$-C$_6$)alkyl and halo.

In another embodiment of Formula I, or a pharmaceutically acceptable salt thereof, R$_1$ is phenyl substituted with 1 or 2 groups selected from —O(C$_1$-C$_6$)alkyl-R$_4$, —(C$_1$-C$_6$)alkyl and —NH(C$_1$-C$_6$)alkyl-R$_5$, and wherein the R$_1$ phenyl group is optionally further substituted with one or two more groups independently selected from —OH, —OCF$_3$, —(C$_1$-C$_3$)alkyl, and halo.

In another embodiment of Formula I, or a pharmaceutically acceptable salt thereof, R$_1$ is phenyl substituted with —O(C$_1$-C$_6$)alkyl-R$_4$.

In another embodiment of Formula I, or a pharmaceutically acceptable salt thereof, R$_1$ is phenyl ortho-substituted with —O(C$_1$-C$_6$)alkyl-R$_4$.

An ortho-substituted phenyl group is generally represented by the following structure:

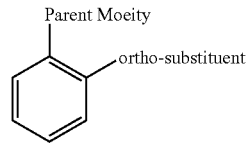

wherein the ortho-substitutent is ortho to the parent moiety.

A para-substituted phenyl group is generally represented by the following structure:

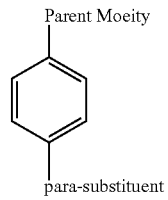

wherein the para-substitutent is para to the parent moiety.

In another embodiment of Formula I, or a pharmaceutically acceptable salt thereof, R$_1$ is phenyl substituted with —O—CH$_2$—C(H)(CH$_3$)$_2$.

In another embodiment of Formula I, or a pharmaceutically acceptable salt thereof, R$_1$ is phenyl ortho-substituted with —O—CH$_2$—C(H)(CH$_3$)$_2$.

In another embodiment of Formula I, or a pharmaceutically acceptable salt thereof, R$_1$ is phenyl substituted with —OH and —(C$_1$-C$_3$)alkyl.

In another embodiment of Formula I, or a pharmaceutically acceptable salt thereof, R$_1$ is

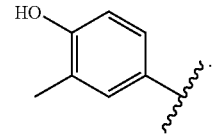

In another embodiment of Formula I, or a pharmaceutically acceptable salt thereof, R$_1$ is —O—(C$_1$-C$_6$)alkyl-OH.

In another embodiment of Formula I, or a pharmaceutically acceptable salt thereof, R$_1$ is phenyl substituted with —N(H)(C$_1$-C$_6$)alkyl-NH$_2$ or —N(H)(C$_1$-C$_6$)alkyl-(4-6 membered) heterocycloalkyl, and the R$_1$ phenyl group is further optionally substituted with one —(C$_1$-C$_6$)alkyl. One non-limiting example of the heterocylcoalkly group in this embodiment includes piperidine.

In another embodiment of Formula I, or a pharmaceutically acceptable salt thereof, R$_1$ is phenyl para-substituted with —N(H)(C$_1$-C$_6$)alkyl-NH$_2$ or —N(H)(C$_1$-C$_6$)alkyl-(4-6 membered)heterocycloalkyl, and the R$_1$ phenyl group is further optionally ortho-substituted with one —(C$_1$-C$_6$)alkyl.

In another embodiment of Formula I, or a pharmaceutically acceptable salt thereof, R$_2$ is indazolyl optionally substituted with 1, 2 or 3 groups, which can be the same or different, selected from —N(H)(C$_1$-C$_6$)alkyl-N(H)C(O)—(C$_1$-C$_6$)alkyl-N[(C$_1$-C$_6$)alkyl]$_2$, —N(H)(C$_1$-C$_6$)alkyl-R$_9$, —(C$_1$-C$_6$)alkyl, —N[(C$_1$-C$_6$)alkyl](C$_1$-C$_6$)alkyl-R$_{10}$, —N(H)C(O)(C$_1$-C$_6$)alkyl-N[(C$_1$-C$_6$)alkyl]$_2$, —O—(C$_1$-C$_6$)alkyl, —NH$_2$, —N(H)C(O)—$(C_1-C_6)$alkyl, phenyl optionally substituted with halo, —N(H)$(C_1-C_6)$alkyl-$(C_6-C_{10})$aryl optionally substituted with halo or alkoxy at any ring position, and —N(H)$(C_1-C_6)$alkyl-$NH_2$.

In another embodiment of Formula I, or a pharmaceutically acceptable salt thereof, $R_2$ is indazolyl optionally substituted with 1, 2 or 3 groups independently selected from —N(H)$(C_1-C_6)$alkyl-N(H)C(O)—$(C_1-C_6)$alkyl-N$[(C_1-C_6)$alkyl$]_2$, —N(H)C(O)$(C_1-C_6)$alkyl-N$[(C_1-C_6)$alkyl$]_2$, —$NH_2$, —N(H)$(C_1-C_6)$alkyl, —N(H)C(O)—$(C_1-C_6)$alkyl, —$(C_1-C_3)$alkyl, —N(H)$(C_1-C_6)$alkyl-$(C_6-C_{10})$aryl optionally substituted with halo or alkoxy at any ring position, and —N(H)$(C_1-C_6)$alkyl-$NH_2$.

In another embodiment of Formula I, or a pharmaceutically acceptable salt thereof, $R_2$ is indazolyl optionally substituted with —N(H)$(C_1-C_3)$alkyl-N(H)C(O)—$(C_1-C_3)$alkyl-N$[(C_1-C_3)$alkyl$]_2$, —N(H)C(O)$(C_1-C_3)$alkyl-N$[(C_1-C_3)$alkyl$]_2$, —$NH_2$, —N(H)$(C_1-C_3)$alkyl, —N(H)C(O)—$(C_1-C_3)$alkyl, —N(H)$(C_1-C_3)$alkyl-phenyl optionally substituted with halo or alkoxy at any ring position, or —N(H)$(C_1-C_3)$alkyl-$NH_2$.

In another embodiment of Formula I, or a pharmaceutically acceptable salt thereof, $R_2$ is furanyl optionally substituted with 1, 2 or 3 methyl groups.

In other embodiments of Formula I, or a pharmaceutically acceptable salt thereof, each of $R_4$, $R_5$, $R_6$, $R_7$, $R_9$, in any of the above embodiments, are independently selected from H, —OH, halo, —$CF_3$, —O$(C_1-C_4)$alkyl, phenyl, —O—$(C_1-C_4)$alkyl-phenyl, —$(C_3-C_6)$cycloalkyl, —CN, -(5-9 membered)heteroaryl, -(4-6 membered)heterocycloalkyl, —$NH_2$, —N(H)$(C_1-C_4)$alkyl, and —N(H)$[(C_1-C_4)$alkyl$]_2$.

In other embodiments of Formula I, or a pharmaceutically acceptable salt thereof, each of $R_4$, $R_5$, $R_6$, $R_7$, $R_9$, in any of the above embodiments, are independently selected from H, —OH, halo, —$CF_3$, —O$(C_1-C_4)$alkyl, phenyl, —O—$(C_1-C_4)$alkyl-phenyl, —$(C_3-C_6)$cycloalkyl, —CN, (5-9 membered)heteroaryl, -(4-6 membered)heterocycloalkyl, phenyl, —$NH_2$, —N(H)$(C_1-C_4)$alkyl, and —N(H)$[(C_1-C_4)$alkyl$]_2$.

In other embodiments of Formula I, or a pharmaceutically acceptable salt thereof, each of $R_9$, and $R_{10}$, in any of the above embodiments, are independently selected from H, —OH, halo, —$CF_3$, —O$(C_1-C_4)$alkyl, phenyl optionally substituted with halo or alkoxy, —O—$(C_1-C_4)$alkyl-phenyl, —$(C_3-C_6)$cycloalkyl, —CN, -(5-9 membered)heteroaryl, -(4-6 membered)heterocycloalkyl, phenyl, —$NH_2$, —N(H)$(C_1-C_4)$alkyl, and —N(H)$[(C_1-C_4)$alkyl$]_2$.

In other embodiments of Formula I, or a pharmaceutically acceptable salt thereof, each of $R_4$, $R_5$, $R_6$, $R_7$, $R_8$, in any of the above embodiments, is H. In other embodiments of Formula I, or a pharmaceutically acceptable salt thereof, each of $R_9$, and $R_{10}$, in any of the above embodiments, is H.

In other embodiments of Formula I, or a pharmaceutically acceptable salt thereof, each of $R_4$, $R_5$, $R_6$, $R_7$, $R_8$, in any of the above embodiments, is —OH. In other embodiments of Formula I, or a pharmaceutically acceptable salt thereof, each of $R_9$, and $R_{10}$, in any of the above embodiments, is —OH.

In other embodiments of Formula I, or a pharmaceutically acceptable salt thereof, each of $R_4$, $R_5$, $R_6$, $R_7$, $R_8$, in any of the above embodiments, is halo. In other embodiments of Formula I, or a pharmaceutically acceptable salt thereof, each of $R_9$, and $R_{10}$, in any of the above embodiments, is halo.

In other embodiments of Formula I, or a pharmaceutically acceptable salt thereof, each of $R_4$, $R_5$, $R_6$, $R_7$, $R_8$, in any of the above embodiments, is —$CF_3$. In other embodiments of Formula I, or a pharmaceutically acceptable salt thereof, each of $R_9$, and $R_{10}$, in any of the above embodiments, is —$CF_3$.

In other embodiments of Formula I, or a pharmaceutically acceptable salt thereof, each of $R_4$, $R_5$, $R_6$, $R_7$, $R_8$, in any of the above embodiments, is —O$(C_1-C_4)$alkyl.

In other embodiments of Formula I, or a pharmaceutically acceptable salt thereof, each of $R_9$, and $R_{10}$, in any of the above embodiments, is —O$(C_1-C_4)$alkyl.

In other embodiments of Formula I, or a pharmaceutically acceptable salt thereof, each of $R_4$, $R_5$, $R_6$, $R_7$, $R_8$, in any of the above embodiments, is phenyl. In other embodiments of Formula I, or a pharmaceutically acceptable salt thereof, each of $R_9$, and $R_{10}$, in any of the above embodiments is phenyl optionally substituted with halo or alkoxy.

In other embodiments of Formula I, or a pharmaceutically acceptable salt thereof, each of $R_4$, $R_5$, $R_6$, $R_7$, $R_8$, in any of the above embodiments, is —O—$(C_1-C_4)$alkyl-phenyl. In other embodiments of Formula I, or a pharmaceutically acceptable salt thereof, each of $R_9$, and $R_{10}$, in any of the above embodiments, is —O—$(C_1-C_4)$alkyl-phenyl.

In other embodiments of Formula I, or a pharmaceutically acceptable salt thereof, each of $R_4$, $R_5$, $R_6$, $R_7$, $R_8$, in any of the above embodiments, is —$(C_3-C_6)$cycloalkyl.

In other embodiments of Formula I, or a pharmaceutically acceptable salt thereof, each of $R_9$, and $R_{10}$, in any of the above embodiments is —$(C_3-C_6)$cycloalkyl.

In other embodiments of Formula I, or a pharmaceutically acceptable salt thereof, each of $R_4$, $R_5$, $R_6$, $R_7$, $R_8$, in any of the above embodiments, is —CN. In other embodiments of Formula I, or a pharmaceutically acceptable salt thereof, each of $R_9$, and $R_{10}$, in any of the above embodiments, is —CN.

In other embodiments of Formula I, or a pharmaceutically acceptable salt thereof, each of $R_4$, $R_5$, $R_6$, $R_7$, $R_8$, in any of the above embodiments, is -(5-9 membered)heteroaryl. In other embodiments of Formula I, or a pharmaceutically acceptable salt thereof, each of $R_9$, and $R_{10}$, in any of the above embodiments is -(5-9 membered)heteroaryl.

In other embodiments of Formula I, or a pharmaceutically acceptable salt thereof, each of $R_4$, $R_5$, $R_6$, $R_7$, $R_8$, in any of the above embodiments, is -(4-6 membered)heterocycloalkyl.

In other embodiments of Formula I, or a pharmaceutically acceptable salt thereof, each of $R_9$, and $R_{10}$, in any of the above embodiments, is -(4-6 membered)heterocycloalkyl.

In other embodiments of Formula I, or a pharmaceutically acceptable salt thereof, each of $R_4$, $R_5$, $R_6$, $R_7$, $R_8$, in any of the above embodiments, is —$NH_2$. In other embodiments of Formula I, or a pharmaceutically acceptable salt thereof, each of $R_9$, and $R_{10}$, in any of the above embodiments, is —$NH_2$.

In other embodiments of Formula I, or a pharmaceutically acceptable salt thereof, each of $R_4$, $R_5$, $R_6$, $R_7$, $R_9$, in any of the above embodiments, is —N(H)$(C_1-C_4)$alkyl. In other embodiments of Formula I, or a pharmaceutically acceptable salt thereof, each of $R_9$, and $R_{10}$, in any of the above embodiments, is —N(H)$(C_1-C_4)$alkyl.

In other embodiments of Formula I, or a pharmaceutically acceptable salt thereof, each of $R_4$, $R_5$, $R_6$, $R_7$, $R_9$, in any of the above embodiments, is —N(H)$[(C_1-C_4)$alkyl$]_2$.

In other embodiments of Formula I, or a pharmaceutically acceptable salt thereof, each of $R_9$, and $R_{10}$, in any of the above embodiments, is —N(H)$[(C_1-C_4)$alkyl$]_2$.

All compounds of Formula I disclosed above include any of the disclosed alternative aspects or embodiments for each of $R_1$, $R_2$, $R_6$, $R_7$, $R_8$, $R_9$, $R_{10}$ and X in combination with any other of the disclosed alternative aspects or embodiments of $R_1$, $R_2$, $R_6$, $R_7$, $R_8$, $R_9$, $R_{10}$ and X as well as any pharmaceutically acceptable salt and stereoisomer of any such combination.

In another embodiment of Formula I, or a pharmaceutically acceptable salt thereof, X is O; $R_1$ is phenyl substituted with 1 group selected from —O($C_1$-$C_6$)alkyl-$R_4$, —($C_1$-$C_6$)alkyl and —N(H)($C_1$-$C_6$)alkyl-$R_5$, and the $R_1$ phenyl group is further optionally substituted with one or two more groups independently selected from —OH, —OCF$_3$, —($C_1$-$C_3$)alkyl, and halo; $R_2$ is indazolyl optionally substituted with 1, 2 or 3 groups, which can be the same or different, selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N[($C_1$-$C_6$)alkyl]$_2$, —O—($C_1$-$C_6$)alkyl, —NH$_2$, —N(H)($C_1$-$C_6$)alkyl, —N(H)C(O)—($C_1$-$C_6$)alkyl, phenyl optionally substituted with halo, —N(H)($C_1$-$C_6$)alkyl-($C_6$-$C_{10}$)aryl optionally substituted with halo or alkoxy at any ring position, and —N(H)($C_1$-$C_6$)alkyl-NH$_2$; $R_3$ is H; and $R_4$ and $R_5$ are as defined in any of the above embodiments.

In another embodiment of Formula I, or a pharmaceutically acceptable salt thereof, X is O; $R_1$ is phenyl ortho-substituted with —O($C_1$-$C_6$)alkyl-$R_4$; $R_2$ is indazolyl optionally substituted with 1, 2 or 3 groups, which can be the same or different, selected from —N(H)($C_1$-$C_6$)alkyl —N(H)C(O)—($C_1$-$C_6$)alkyl-N [($C_1$-$C_6$)alkyl]$_2$, —N(H)C(O)($C_1$-$C_6$)alkyl-N[($C_1$-$C_6$)alkyl]$_2$, —O—($C_1$-$C_6$)alkyl, —NH$_2$, —N(H)($C_1$-$C_6$)alkyl, —N(H)C(O)—($C_1$-$C_6$)alkyl, phenyl optionally substituted with halo, —N(H)($C_1$-$C_6$)alkyl-($C_6$-$C_{10}$)aryl optionally substituted with halo or alkoxy at any ring position, and —NH($C_1$-$C_6$)alkyl-NH$_2$; $R_3$ is H; and $R_4$ is as defined in any of the above embodiments.

In another embodiment of Formula I, or a pharmaceutically acceptable salt thereof, X is O; $R_1$ is phenyl substituted with —O—CH$_2$—C(H)(CH$_3$)$_2$; $R_2$ is indazolyl optionally substituted with 1, 2 or 3 groups, which can be the same or different, selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N[($C_1$-$C_6$)alkyl]$_2$, —O—($C_1$-$C_6$)alkyl, —NH$_2$, —N(H)($C_1$-$C_6$)alkyl, —N(H)C(O)—($C_1$-$C_6$)alkyl, phenyl optionally substituted with halo, —N(H)($C_1$-$C_6$)alkyl-($C_6$-$C_{10}$)aryl optionally substituted with halo or alkoxy at any ring position, and —N(H)($C_1$-$C_6$)alkyl-NH$_2$; and $R_3$ is H.

In another embodiment of Formula I, or a pharmaceutically acceptable salt thereof, X is O; $R_1$ is phenyl substituted with —O($C_1$-$C_6$)alkyl-$R_4$; $R_2$ is indazolyl optionally substituted with 1, 2 or 3 groups, which can be the same or different, selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N [($C_1$-$C_6$)alkyl]$_2$, —O—($C_1$-$C_6$)alkyl, —NH$_2$, —N(H)($C_1$-$C_6$)alkyl, —N(H)C(O)—($C_1$-$C_6$)alkyl, phenyl optionally substituted with halo, —N(H)($C_1$-$C_6$)alkyl-($C_6$-$C_{10}$)aryl optionally substituted with halo or alkoxy at any ring position, and —N(H)($C_1$-$C_6$)alkyl-NH$_2$; $R_3$ is H; and $R_4$ is as defined in any of the above embodiments.

In another embodiment of Formula I, or a pharmaceutically acceptable salt thereof, X is O; $R_1$ is phenyl substituted with —O($C_1$-$C_6$)alkyl-$R_4$; $R_2$ is indazolyl optionally substituted with 1, 2 or 3 groups, which can be the same or different, selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N [($C_1$-$C_6$)alkyl]$_2$, —O—($C_1$-$C_6$)alkyl, —NH$_2$, —N(H)($C_1$-$C_6$)alkyl, —N(H)C(O)—($C_1$-$C_6$)alkyl, phenyl optionally substituted with halo, —N(H)($C_1$-$C_6$)alkyl-($C_6$-$C_{10}$)aryl optionally substituted with halo or alkoxy at any ring position, and —N(H)($C_1$-$C_6$)alkyl-NH$_2$; $R_3$ is H; and $R_4$ is as defined in any of the above embodiments.

In another embodiment of Formula I, or a pharmaceutically acceptable salt thereof, X is O; $R_1$ is phenyl ortho-substituted with —O—CH$_2$—C(H)(CH$_3$)$_2$; $R_2$ is indazolyl optionally substituted with 1, 2 or 3 groups, which can be the same or different, selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N[($C_1$-$C_6$)alkyl]$_2$, —O—($C_1$-$C_6$)alkyl, —NH$_2$, —N(H)($C_1$-$C_6$)alkyl, —N(H)C(O)—($C_1$-$C_6$)alkyl, phenyl optionally substituted with halo, —N(H)($C_1$-$C_6$)alkyl-($C_6$-$C_{10}$)aryl optionally substituted with halo or alkoxy at any ring position, and —N(H)($C_1$-$C_6$)alkyl-NH$_2$; and $R_3$ is H.

In another embodiment of Formula I, or a pharmaceutically acceptable salt thereof, X is O; $R_1$ is phenyl substituted with —OH and —($C_1$-$C_3$)alkyl; $R_2$ is indazolyl optionally substituted with 1, 2 or 3 groups, which can be the same or different, selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N[($C_1$-$C_6$)alkyl]$_2$, —O—($C_1$-$C_6$)alkyl, —NH$_2$, —N(H)($C_1$-$C_6$)alkyl, —N(H)C(O)—($C_1$-$C_6$)alkyl, phenyl optionally substituted with halo, —N(H)($C_1$-$C_6$)alkyl-($C_6$-$C_{10}$)aryl optionally substituted with halo or alkoxy at any ring position, and —N(H)($C_1$-$C_6$)alkyl-NH$_2$; and $R_3$ is H.

In another embodiment of Formula I, or a pharmaceutically acceptable salt thereof, X is O; $R_1$ is

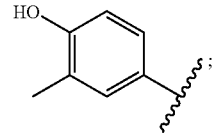

$R_2$ is indazolyl optionally substituted with 1, 2 or 3 groups, which can be the same or different, selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N[($C_1$-$C_6$)alkyl]$_2$, —O—($C_1$-$C_6$)alkyl, —NH$_2$, —N(H)($C_1$-$C_6$)alkyl, —N(H)C(O)—($C_1$-$C_6$)alkyl, phenyl optionally substituted with halo, —N(H)($C_1$-$C_6$)alkyl-($C_6$-$C_{10}$)aryl optionally substituted with halo or alkoxy at any ring position, and —N(H)($C_1$-$C_6$)alkyl-NH$_2$; and $R_3$ is H.

In another embodiment of Formula I, or a pharmaceutically acceptable salt thereof, X is O; $R_1$ is —O—($C_1$-$C_6$)alkyl-OH; $R_2$ is indazolyl optionally substituted with 1, 2 or 3 groups, which can be the same or different, selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N[($C_1$-$C_6$)alkyl]$_2$, —O—($C_1$-$C_6$)alkyl, —NH$_2$, —N(H)($C_1$-$C_6$)alkyl, —N(H)C(O)—($C_1$-$C_6$)alkyl, phenyl optionally substituted with halo, —N(H)($C_1$-$C_6$)alkyl-($C_6$-$C_{10}$)aryl optionally substituted with halo or alkoxy at any ring position, and —N(H)($C_1$-$C_6$)alkyl-NH$_2$; and $R_3$ is H.

In another embodiment of Formula I, or a pharmaceutically acceptable salt thereof, X is O; $R_1$ is phenyl substituted with —N(H)($C_1$-$C_6$)alkyl-NH$_2$ or —N(H)($C_1$-$C_6$)alkyl-(4-6 membered)heterocycloalkyl, and the $R_1$ phenyl group is further optionally substituted with one —($C_1$-$C_6$)alkyl; $R_2$ is indazolyl optionally substituted with 1, 2 or 3 groups, which can be the same or different, selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N[($C_1$-$C_6$)alkyl]$_2$, —O—($C_1$-$C_6$)alkyl, —NH$_2$, —N(H)($C_1$-$C_6$)alkyl, —N(H)C(O)—($C_1$-$C_6$)alkyl, phenyl optionally substituted with halo, —N(H)($C_1$-$C_6$)alkyl-($C_6$-$C_{10}$)aryl optionally substituted with halo or alkoxy at any ring position, and —N(H)($C_1$-$C_6$)alkyl-NH$_2$; and $R_3$ is H.

In another embodiment of Formula I, or a pharmaceutically acceptable salt thereof, X is O; $R_1$ is phenyl para-substituted with —N(H)($C_1$-$C_6$)alkyl-NH$_2$ or —N(H)($C_1$-$C_6$)alkyl-(4-6 membered)heterocycloalkyl, and the $R_1$ phenyl group is further optionally ortho-substituted with one —$(C_1-C_6)$alkyl; $R_2$ is indazolyl optionally substituted with 1, 2 or 3 groups, which can be the same or different, selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N[($C_1$-$C_6$)alkyl]$_2$, —O—($C_1$-$C_6$)alkyl, —NH$_2$, —N(H)($C_1$-$C_6$)alkyl, —N(H)C(O)—($C_1$-$C_6$)alkyl, phenyl optionally substituted with halo, —N(H)($C_1$-$C_6$)alkyl-($C_6$-$C_{10}$)aryl optionally substituted with halo or alkoxy at any ring position, and N(H)($C_1$-$C_6$)alkyl-NH$_2$; and $R_3$ is H.

In another embodiment of Formula I, or a pharmaceutically acceptable salt thereof, X is O; $R_1$ is phenyl substituted with 1 group selected from —O($C_1$-$C_6$)alkyl-$R_4$, —($C_1$-$C_6$)alkyl and —N(H)($C_1$-$C_6$)alkyl-$R_5$, and the $R_1$ phenyl group is further optionally substituted with one or two more groups independently selected from —OH, —OCF$_3$, —($C_1$-$C_3$)alkyl, and halo; $R_2$ is indazolyl optionally substituted with —N(H)—($C_1$-$C_3$)alkyl-N(H)C(O)—($C_1$-$C_3$)alkyl-N[($C_1$-$C_3$)alkyl]$_2$, —N(H)C(O)($C_1$-$C_3$)alkyl-N[($C_1$-$C_3$)alkyl]$_2$, —NH$_2$, —N(H)($C_1$-$C_3$)alkyl, —N(H)C(O)—($C_1$-$C_3$)alkyl, —N(H)($C_1$-$C_3$)alkyl-phenyl optionally substituted with halo or alkoxy at any ring position, and —N(H)($C_1$-$C_3$)alkyl-NH$_2$; $R_3$ is H; and $R_4$ and $R_5$ are as defined in any of the above embodiments.

In another embodiment of Formula I, or a pharmaceutically acceptable salt thereof, X is O; $R_1$ is phenyl substituted with 1 group selected from —O($C_1$-$C_6$)alkyl-$R_4$—($C_1$-$C_6$)alkyl and —N(H)($C_1$-$C_6$)alkyl-$R_5$, and the $R_1$ phenyl group is further optionally substituted with one or two more groups independently selected from —OH, —OCF$_3$, —($C_1$-$C_3$)alkyl, and halo; $R_2$ is indazolyl optionally substituted with 1, 2 or 3 groups selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N[($C_1$-$C_6$)alkyl]$_2$, —NH$_2$, —N(H)($C_1$-$C_6$)alkyl, —N(H)C(O)—($C_1$-$C_6$)alkyl, —($C_1$-$C_3$)alkyl, —N(H)($C_1$-$C_6$)alkyl-($C_6$-$C_{10}$)aryl optionally substituted with halo or alkoxy at any ring position, and —N(H)($C_1$-$C_6$)alkyl-NH$_2$; $R_3$ is H; and $R_4$ and $R_5$ are as defined in any of the above embodiments.

In another embodiment of Formula I, or a pharmaceutically acceptable salt thereof, X is O; $R_1$ is phenyl substituted with 1 group selected from —O($C_1$-$C_6$)alkyl-$R_4$, —($C_1$-$C_6$)alkyl and —NH($C_1$-$C_6$)alkyl-$R_5$, and the $R_1$ phenyl group is further optionally substituted with one or two more groups independently selected from —OH, —OCF$_3$, —($C_1$-$C_3$)alkyl, and halo; $R_2$ is indazolyl optionally substituted with 1, 2 or 3 groups selected from —N(H)($C_1$-$C_6$)alkyl-N(H)C(O)—($C_1$-$C_6$)alkyl-N[($C_1$-$C_6$)alkyl]$_2$, —N(H)C(O)($C_1$-$C_6$)alkyl-N[($C_1$-$C_6$)alkyl]$_2$, —NH$_2$, —N(H)($C_1$-$C_6$)alkyl, —N(H)C(O)—($C_1$-$C_6$)alkyl, —($C_1$-$C_3$)alkyl, —N(H)($C_1$-$C_6$)alkyl-($C_6$-$C_{10}$)aryl optionally substituted with halo or alkoxy at any ring position, and —N(H)($C_1$-$C_6$)alkyl-NH$_2$; $R_3$ is H; and $R_4$ and $R_5$ are as defined in any of the above embodiments.

In other embodiments, any of the alkyl groups referred to in any of the above embodiments, including alkyl portions attached to other groups, can be a —($C_1$-$C_3$)alkyl group.

In other embodiments, any of the alkoxy groups referred to in any of the above embodiments, including alkoxy portions attached to other groups, can be a —($C_1$-$C_3$)alkoxy group.

In other embodiments, any of the alkoxy groups referred to in any of the above embodiments, including alkoxy portions attached to other groups, can be a —($C_1$-$C_2$)alkoxy group.

Another aspect of the invention relates to a pharmaceutical composition comprising a compound according to Formula I, or a pharmaceutically acceptable salt thereof, and a pharmaceutically acceptable carrier, excipient, or diluent.

Another aspect of the invention relates to a method of inhibiting CK2 in a cell, comprising contacting a cell in which inhibition of CK2 is desired with a compound according to Formula I, or a pharmaceutically acceptable salt thereof.

Another aspect of the invention relates to a method of inhibiting CK2 in a cell, comprising contacting a cell in which inhibition of CK2 is desired with a pharmaceutical composition comprising a compound according to Formula I, or a pharmaceutically acceptable salt thereof, and a pharmaceutically acceptable carrier, excipient, or diluent.

Another aspect of the invention relates to a method of treating a disease or condition that involves CK2 comprising administering to a patient, in need of the treatment, a compound according to Formula I, or a pharmaceutically acceptable salt thereof. Non-limiting examples of the disease or condition that can be treated include cancer such as ovarian cancer, cervical cancer, breast cancer, colorectal cancer, or glioblastomas.

Another aspect of the invention relates to a method of treating a disease or condition that involves CK2 comprising administering to a patient, in need of the treatment, a pharmaceutical composition comprising a compound according to Formula I, or a pharmaceutically acceptable salt thereof, and a pharmaceutically acceptable carrier, excipient, or diluent. Non-limiting examples of the disease or condition that can be treated include cancer such as ovarian cancer, cervical cancer, breast cancer, colorectal cancer, or glioblastomas.

Another aspect of the invention relates to a method of treating a disease or condition that involves CK2 comprising administering to a patient, in need of the treatment, a compound according to Formula I, or a pharmaceutically acceptable salt thereof, in combination with radiation treatment and/or one or more therapeutic angents selected from Camptothecin, Topotecan, 9-Nitrocamptothecin, 9-Aminocamptothecin, Karenitecin, Irinotecan, Etoposide, Etoposide Phosphate, Teniposide, Amsacrine, Razoxane, Dexrazoxane, Mechlorethamine, Cyclophosphamide, Ifosfamide, Chlorambucil, Melphalan, Thiotepa, Trenimon, Triethylenemelamine, Rapamycin, Dianhydrogalactitol, Dibromodulcitol, Busulfan, dimethylsulfate, Chloroethylnitrosourea, BCNU, CCNU, Methyl-CCNU, Streptozotocin, Chlorozotocin, Prednimustine, Estramustine, Procarbazine, Dacarbazine, Hexamethylmel amine, Pentamethylmelamine, Temozolomide, Cisplatin, Carboplatin, Oxaliplatin, Bleomycin, Dactinomycin, Mithramycin, Mitomycin C, Daunorubicin, Doxorubicin, Epirubicin, Idarubicin, Methotrexate, Edatrexate, Trimethoprim, Nolatrexed, Raltitrexed, Hydroxyurea, 5-fluorouracil, Ftorafur, Capecitabine, Furtulon, Eniluracil, ara-C, 5-azacytidine, Gemcitabine, Mercaptopurine, Thioguanine, Pentostatin, antisense DNA, antisense RNA, an antisense DNA/RNA hybrid, a ribozyme, ultraviolet radiation, Vincristine, Vinblastine, Paclitaxel, Docetaxel, L-Asparaginase, a kinase inhibitor, Imatinib, Mitotane, Aminoglutethimide, Diethylstilbestrol, Ethinyl estradiol, Tamoxifen, Anastrozole, Testosterone propionate, Fluoxymesterone, Flutamide, Leuprolide, Prednisone, Hydroxyprogesterone caproate, Medroxyprogesterone acetate, Megestrol acetate, Interferon-alfa, and Interleukin. In a more specific embodiment, the combination is with Rapamycin.

In another embodiment, the compound of Formula I, or its pharmaceutically acceptable salt, is selected from one of the compounds from Table 1 below. Table I illustrates some examples of the compounds of the invention. The examples in Table 1 are merely illustrative, and do not limit the scope of the invention in any way.

For purposes of this disclosure, if the number of possible optional or non-optional substituents in any of the above embodiments is not specified, than it is assumed that the number of these optional or non-optional substituents for this particular embodiment is 1 substituent.

TABLE 1

| Compound Number | Structure | Name |
|---|---|---|
| 1 | 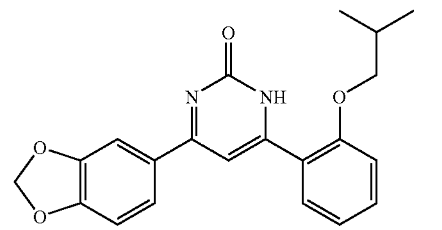 | 4-(1,3-benzodioxol-5-yl)-6-{2-[(2-methylpropyl)oxy]phenyl}pyrimidin-2-(1H)-one |
| 2 | 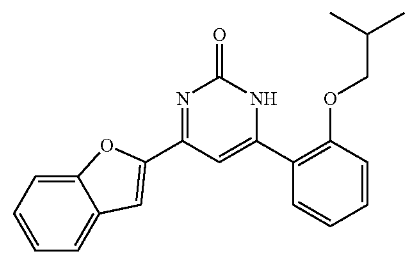 | 4-(1-benzofuran-2-yl)-6-{2-[(2-methylpropyl)oxy]phenyl}pyrimidin-2(1H)-one |
| 3 | 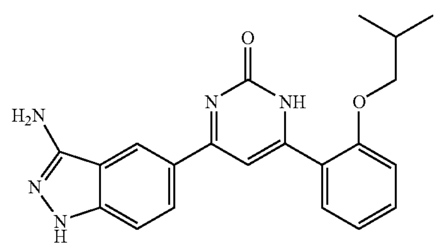 | 4-(3-amino-1H-indazol-5-yl)-6-{2-[(2-methylpropyl)oxy]phenyl}pyrimidin-2(1H)-one |
| 4 | 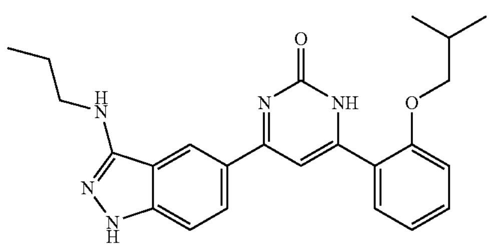 | 6-{2-[(2-methylpropyl)oxy]phenyl}-4-[3-(propylamino)-1H-indazol-5-yl]pyrimidin-2(1H)-one |
| 5 | 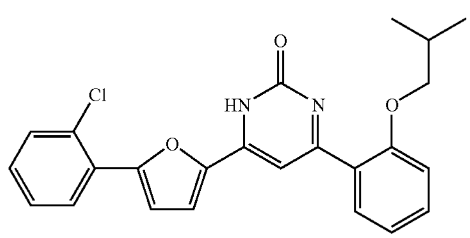 | 6-[5-(2-chlorophenyl)furan-2-yl]-4-{2-[(2-methylpropyl)oxy]phenyl}pyrimidin-2-(1H)-one |
| 6 | 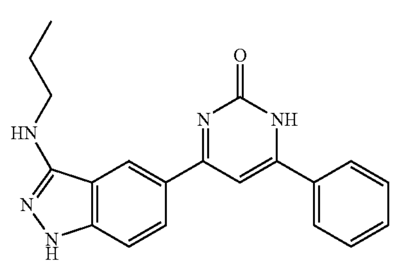 | 6-phenyl-4-[3-(propylamino)-1H-indazol-5-yl]pyrimidin-2(1H)-one |

TABLE 1-continued

| Compound Number | Structure | Name |
|---|---|---|
| 7 | 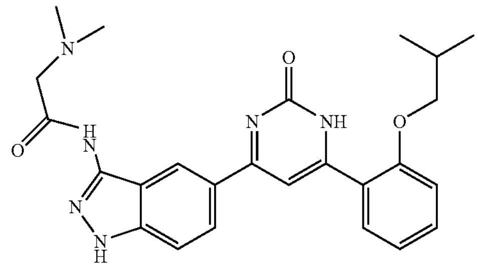 | N²,N²-dimethyl-N-[5-(6-{2-[(2-methylpropyl)oxy]phenyl}-2-oxo-1,2-dihydropyrimidin-4-yl)-1H-indazol-3-yl]glycinamide |
| 8 | 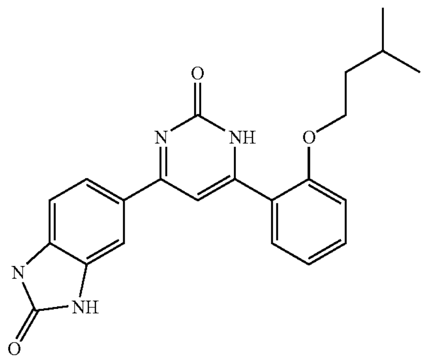 | 5-(6-{2-[(3-methytbutyl)oxy]phenyl}-2-oxo-1,2-dihydropyrimidin-4-yl)-1,3-dihydro-2H-benzimidazol-2-one |
| 9 | 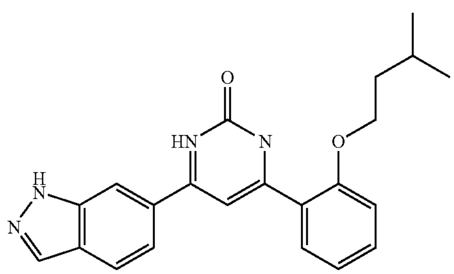 | 6-(1H-indazol-6-yl)-4-{2-[(3-methylbutyl)oxy]phenyl}pyrimidin-2(1H)-one |
| 10 | 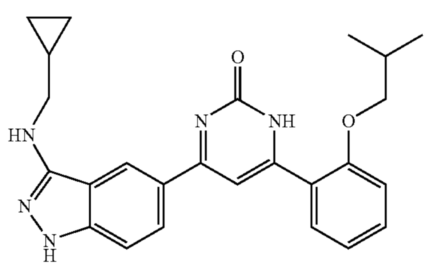 | 4-{3-[(cyclopropylmethyl)amino]-1H-indazol-5-yl}-6-{2-[(2-methylpropyl)oxy]phenyl}pyrimidin-2(1H)-one |
| 11 | 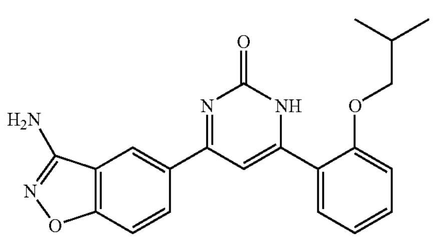 | 4-(3-amino-1,2-benzisoxazol-5-yl)-6-{2-[(2-methylpropyl)oxy]phenyl}pyrimidin-2(1H)-one |

TABLE 1-continued

| Compound Number | Structure | Name |
|---|---|---|
| 12 | 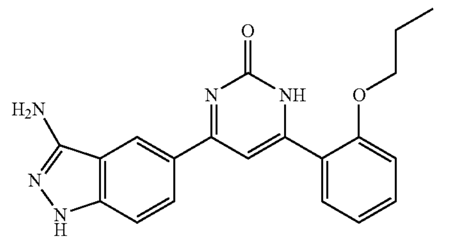 | 4-(3-amino-1H-indazol-5-yl)-6-[2-(propyloxy)phenyl]pyrimidin-2(1H)-one |
| 13 | 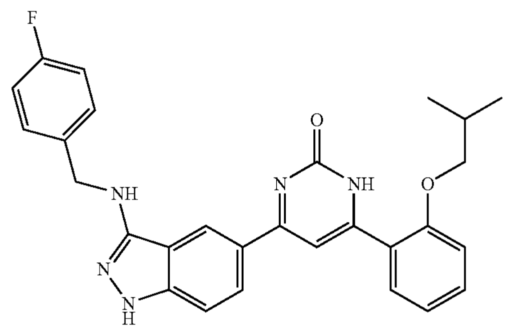 | 4-(3-{[(4-fluorophenyl)methyl]amino}-1H-indazol-5-yl)-6-{2-[(2-methylpropyl)oxy]phenyl}pyrimidin-2(1H)-one |
| 14 | 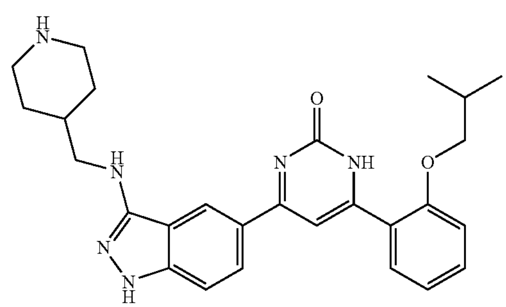 | 6-{2-[(2-methylpropyl)oxy]phenyl}-4-{3-[(piperidin-4-ylmethyl)amino]-1H-indazol-5-yl}pyrimidin-2(1H)-one |
| 15 | 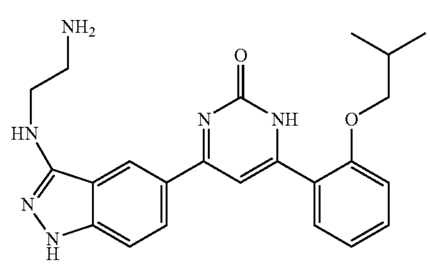 | 4-{3-[(2-aminoethyl)amino]-1H-indazol-5-yl}-6-{2-[(2-methylpropyl)oxy]phenyl}pyrimidin-2(1H)one |
| 16 | 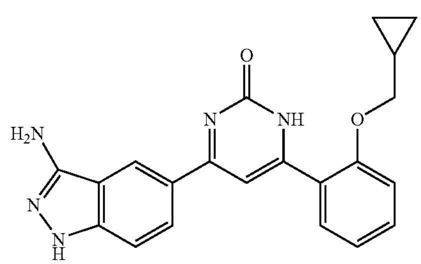 | 4-(3-amino-1H-indazol-5-yl)-6-{2-[(cyclopropylmethyl)oxy]phenyl}pyrimidin-2(1H)-one |

TABLE 1-continued

| Compound Number | Structure | Name |
|---|---|---|
| 17 | 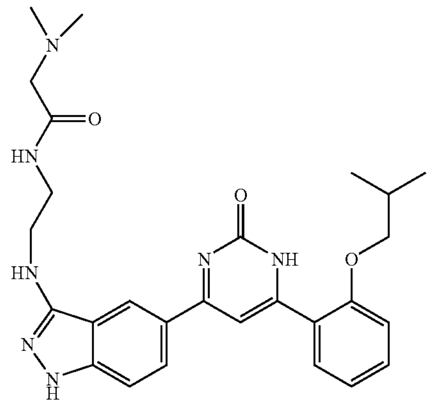 | N~2~,N~2~-dimethyl-N-(2-{[5-(6-{2-[(2-methylpropyloxy]phenyl}-2-oxo-1,2-dihydropyrimidin-4-yl)-1H-indazol-3-yl]amino}ethyl)glycinamide |
| 18 | 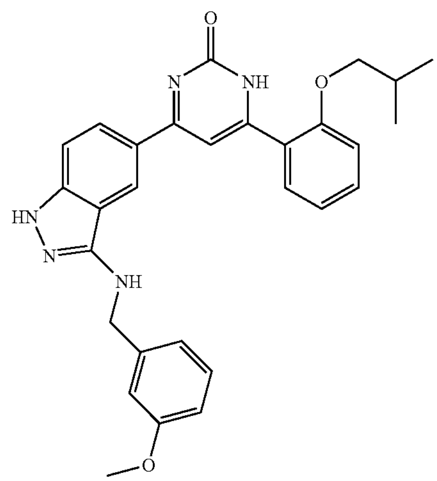 | 4-[3-({[3-(methyloxy)phenyl]methyl}amino)-1H-indazol-5-yl]-6-{2-[(2-methylpropyl)oxy]phenyl}pyrimidin-2(1H)-one |
| 19 | 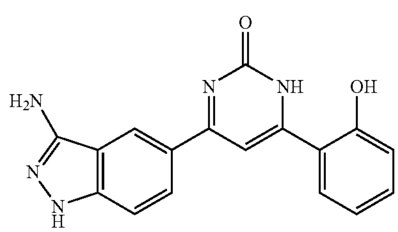 | 4-(3-amino-1H-indazol-5-yl)-6-(2-hydroxyphenyl)pyrimidin-2(1H)-one |
| 20 | 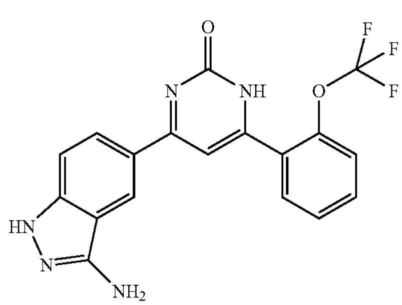 | 4-(3-amino-1H-indazol-5-yl)-6-{2-[(trifluoromethyl)oxy]phenyl}pyrimidin-2(1H)-one |

TABLE 1-continued

| Compound Number | Structure | Name |
| --- | --- | --- |
| 21 | 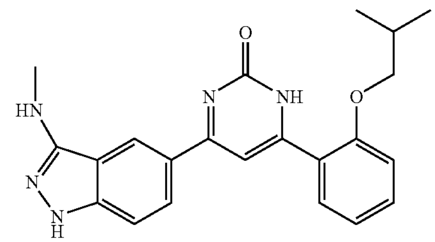 | 4-[3-(methylamino)-1H-indazol-5-yl]-6-{2-[(2-methylpropyl)oxy]phenyl}pyrimidin-n1 2(1H)-one |
| 22 | 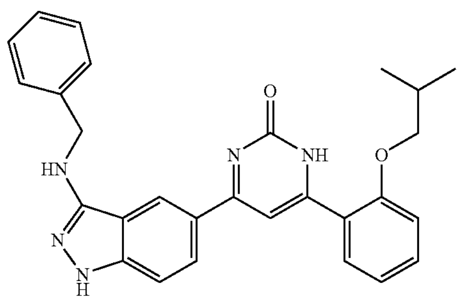 | 6-{2-[(2-methylpropyl)oxy]phenyl}-4-{3-[(phenylmethyl)amino]-1H-indazol-5-yl}pyrimidin-2(1H)-one |
| 23 | 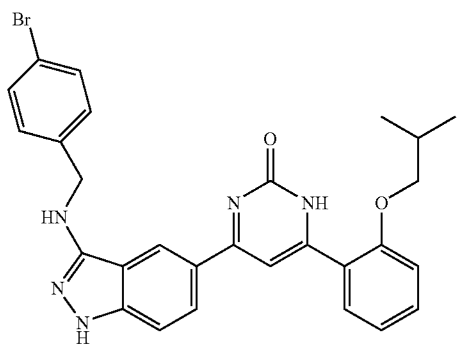 | 4-(3-{[(4-bromophenyl)methyl]amino}-1H-indazol-5-yl)-6-{2-[(2-methylpropyl)oxy]phenyl}pyrimidin-2(1H)-one |
| 24 | 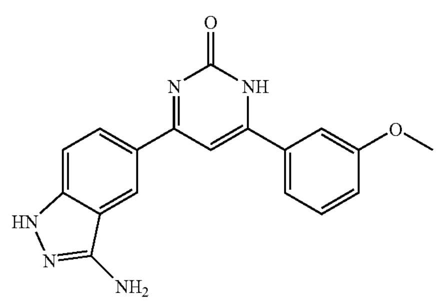 | 4-(3-amino-1H-indazol-5-yl)-6-[3-(methoyloxy)phenyl]pyrimidin-2(1H)-one |
| 25 | 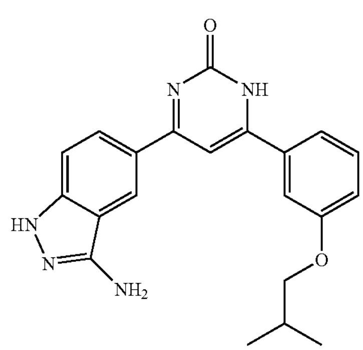 | 4-(3-amino-1H-indazol-5-yl)-6-(3-isobutoxyphenyl)pyrimidin-2(1H)-one |

TABLE 1-continued

| Compound Number | Structure | Name |
|---|---|---|
| 26 | 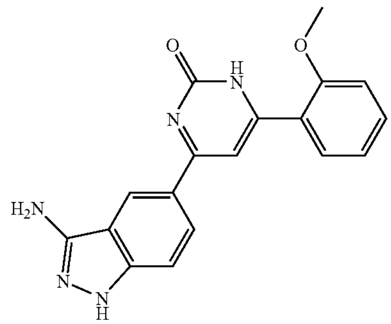 | 4-(3-amino-1H-indazol-5-yl)-6-[2-methloxy)phenyl]pyrimidin-2(1H)-one |
| 27 | 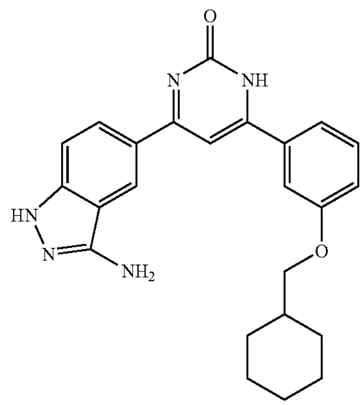 | 4-(3-amino-1H-indazol-5-yl)-6-{3-[(cyclohexylmethyl)oxy]phenyl}pyrimidin-2(1H)-one |
| 28 | 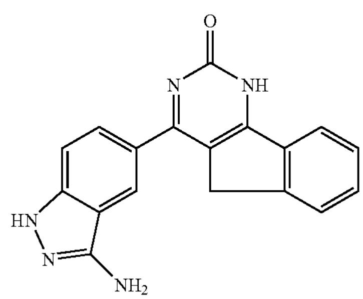 | 4-(3-amino-1H-indazol-5-yl)-1,5-dihydro-2H-indeno[1,2-d]pyrimidin-2-one |
| 29 | 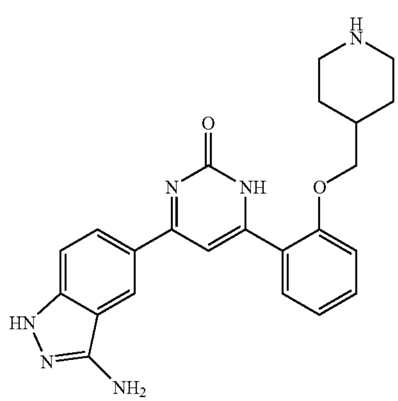 | 4-(3-amino-1H-indazol-5-yl)-6-{2-[(piperidin-4-ylmethyl)oxy]phenyl}pyrimidin-2(1H)-one |

TABLE 1-continued

| Compound Number | Structure | Name |
|---|---|---|
| 30 | 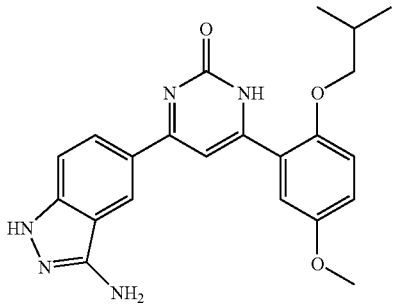 | 4-(3-amino-1H-indazol-5-yl)-6-{5-(methyloxy)-2-[(2-methylpropyl)oxy]phenyl}pyrimidin-2(1H)-one |
| 31 | 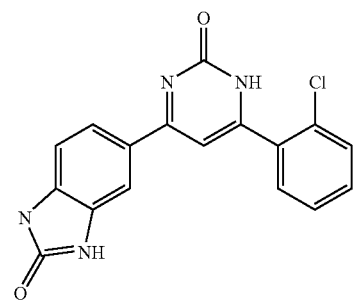 | 5-[6-(2-chlorophenyl)-2-oxo-1,2-dihydropyrimidin-4-yl]-1,3-dihydro-2H-benzimidazol-2-one |
| 32 | 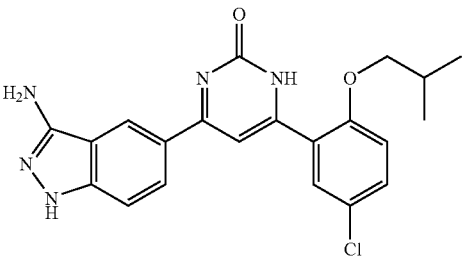 | 4-(3-amino-1H-indazol-5-yl)-6-{5-chloro-2-[(2-methylpropyl)oxy]phenyl}pyrimidin-2(1H)-one |
| 33 | 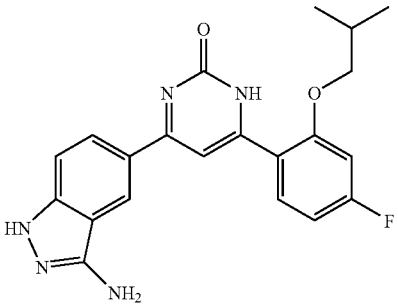 | 4-(3-amino-1H-indazol-5yl)-6{4-fluoro-2-methylpropyl)oxy]phenyl}pyrimidin-2(1H)-one |
| 34 | 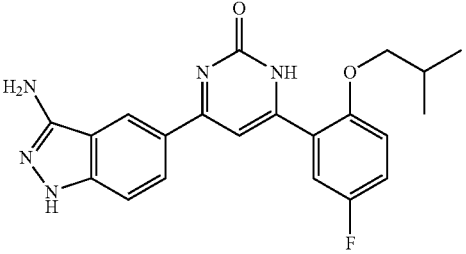 | 4-(3-amino-1H-indazol-5-yl)-6-{5-fluoro-2-[(2-methylpropyl)oxy]phenyl}pyrimidin-2(1H)-one |

TABLE 1-continued

| Compound Number | Structure | Name |
|---|---|---|
| 35 | 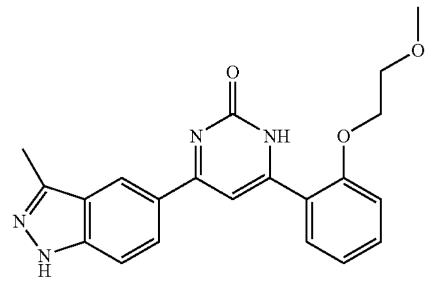 | 4-(3-methyl-1H-indazol-5-yl)-6-(2-{[2-(methyloxy)ethyl]oxy}phenyl)pyrimidin-2(1H)-one |
| 36 | 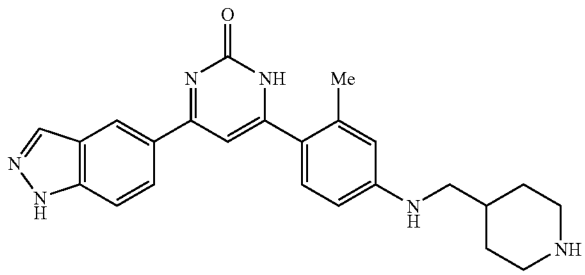 | 4-(1H-indazol-5-yl)-6-{2-methyl-4-[(piperidin-4-ylmethyl)amino]phenyl}pyrimidin-2(1H)-one |
| 37 | 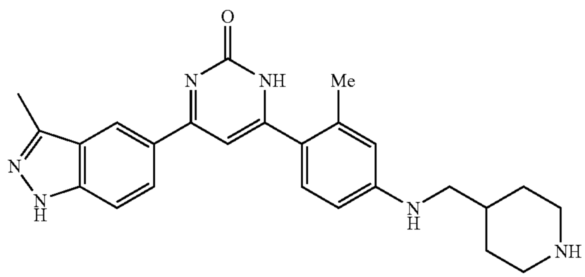 | 4-(3-methyl-1H-indazol-5-yl)-6-{2-methyl-4-[(piperidin-4-ylmethyl)amino]phenyl}pyrimidin-2(1H)-one |
| 38 | 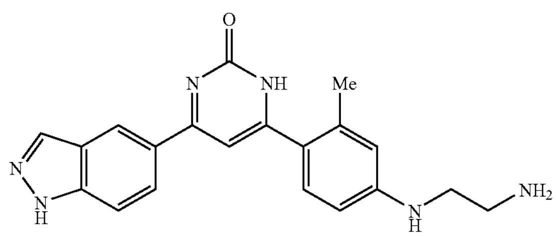 | 6-{4-[(2-aminoethyl)amino]-2-methylphenyl}-4-(1H-indazol-5-yl)pyrimidin-2(1H)-one |
| 39 | 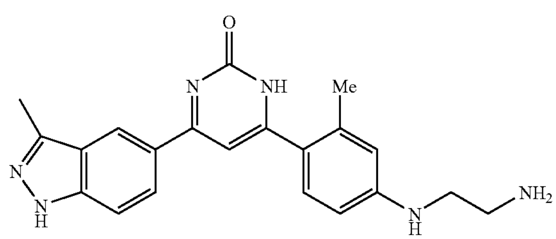 | 6-{4-[(2-aminoethyl)amino]-2-methylphenyl}-4-(3-methyl-1H-indazol-5-yl)pyrimidin-2(1H)-one |
| 40 | 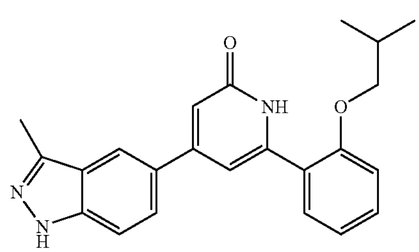 | 4-(3-methyl-1H-indazol-5-yl)-6-{2-[(2-methylpropyl)oxy]phenyl}pyridin-2(1H)-one |

TABLE 1-continued

| Compound Number | Structure | Name |
|---|---|---|
| 41 | 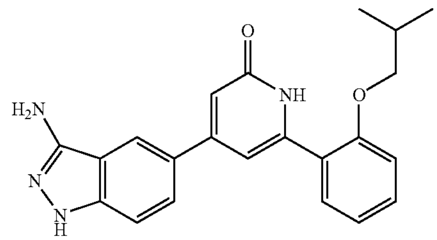 | 4-(3-amino-1H-indazol-5-yl)-6-{2-[(2-methylpropyl)oxy]phenyl}pyridin-2(1H)-one |
| 42 | 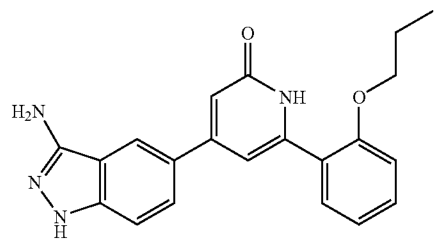 | 4-(3-amino-1H-indazol-5-yl)-6-[2-(propyloxy)phenyl]pyridin-2(1H)-one |
| 43 | 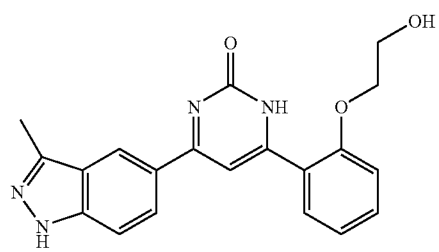 | 6-{2-[(2-hydroxyethyl)oxy]phenyl}4-(3-methyl-1H-indazol-5-yl)pyrimidin-2(1H)-one |
| 44 | 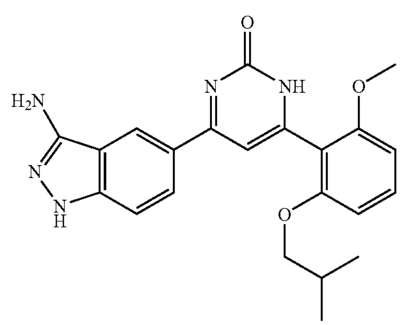 | 4-(3-amino-1H-indazol-5-yl)-6-{2-(methyloxy)-6-[(2-methylpropyl)oxy]phenyl}pyrimidin-2(1H)-one |
| 45 | 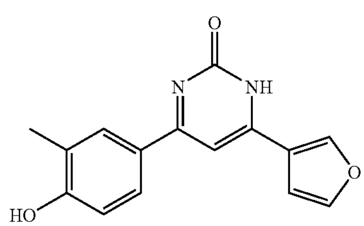 | 6-furan-3-yl-4-(4-hydroxy-3-methylphenyl)pyrimidin-2(1H)-one |
| 46 | 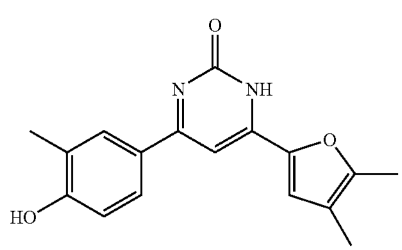 | 6-(4,5-dimethylfuran-2-yl)-4-(4-hydroxy-3-methylphenyl)pyrimidin-2(1H)-one |

TABLE 1-continued

| Compound Number | Structure | Name |
|---|---|---|
| 47 | 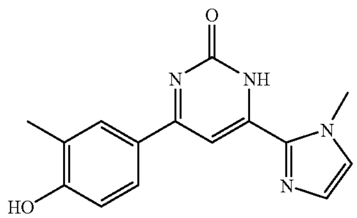 | 4-(4-hydroxy-3-methylphenyl)-6-(1-methyl-1H-imidazol-2-yl)pyrimidin-2(1H)-one |
| 48 | 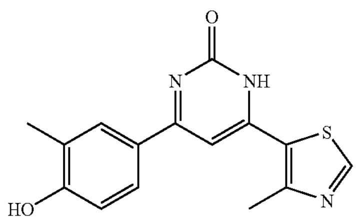 | 4-(4-hydroxy-3-methylphenyl)-6-(4-methyl-1,3-thiazol-5-yl)pyrimidin-2(1H)-one |
| 49 | 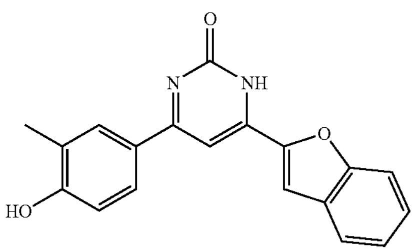 | 6-(1-benzofuran-2-yl)-4-(4-hydroxy-3-methylphenyl)pyrimidin-2(1H)-one |
| 50 | 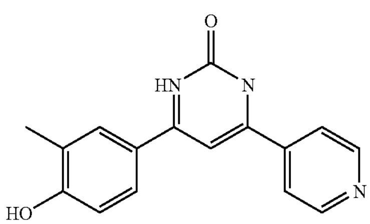 | 6-(4-hydroxy-3-methylphenyl)-4-pyridin-4-ylpyrimidin-2(1H)-one |

In another embodiment, the compound of Formula I is selected from compounds I-49 in Table 1.

The compounds in the table above can be prepared using art recognized methods.

ABBREVIATIONS AND DEFINITIONS

The following abbreviations and terms have the indicated meanings throughout:

| Abbreviation | Meaning |
|---|---|
| Ac | Acetyl |
| ° C. | degrees Celsius |
| CBZ | CarboBenZoxy = benzyloxycarbonyl |
| D | Doublet |
| DIPEA | N,N-diisopropylethylamine |
| DMF | N,N-dimethylformamide |
| DMSO | dimethyl sulfoxide |
| EI | Electron Impact ionization |
| Et | Ethyl |
| G | gram(s) |
| GC | gas chromatography |
| h or hr | hour(s) |
| HOAc | acetic acid |
| HOBt | Hydroxybenzotriazole |
| HPLC | high pressure liquid chromatography |
| L or L | liter(s) |
| M | molar or molarity |
| M | Multiplet |
| Me | Methyl |
| Mesyl | Methanesulfonyl |
| Mg or mg | milligram(s) |
| MHz | megahertz (frequency) |
| Min | minute(s) |
| mL | milliliter(s) |
| mM | Millimolar |
| Mmol | millimole(s) |
| Mol or mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | Nanomolar |
| NMO | N-methylmorpholine oxide |
| NMR | nuclear magnetic resonance spectroscopy |
| Ph | Phenyl |
| PhOH | Phenol |

| Abbreviation | Meaning |
|---|---|
| PPTS | Pyridinium p-toluenesulfonate |
| Q | Quartet |
| RT or rt | Room temperature |
| Sat'd | Saturated |
| S | Singlet |
| T | Triplet |
| TFA | trifluoroacetic acid |
| THF | Tetrahydrofuran |
| TMOF | trimethyl orthoformate |
| TMS | Trimethylsilyl |
| Tosyl | p-toluenesulfonyl |
| uL | microliter(s) |
| uM | Micromole(s) or micromolar |
| LS/MSD | A type of Liquid Chromatography Mass Spectrometer |
| PPh$_3$ | Triphenylphosphine |

DEFINITIONS

As used in the present specification, the following words and phrases are generally intended to have the meanings as set forth below, except to the extent that the context in which they are used indicates otherwise or they are expressly defined to mean something different.

The symbol "-" means a single bond and/or the point of attachment. Thus, the point of attachment of a —(C$_1$-C$_6$) alkyl-(C$_6$-C$_{10}$)aryl group to the parent moiety is at the —(C$_1$-C$_6$)alkyl moiety of this group. "=====" means a single or double bond. When a group is depicted removed from its parent formula, the "～～～" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

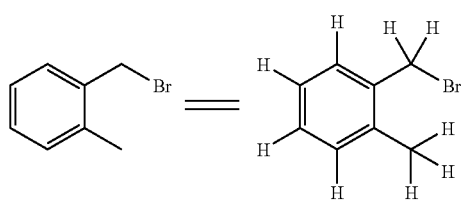

If a group "R" is depicted as "floating" on a ring system, as for example in the formula:

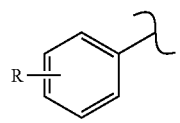

then, unless otherwise defined, a substituent "R" can reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

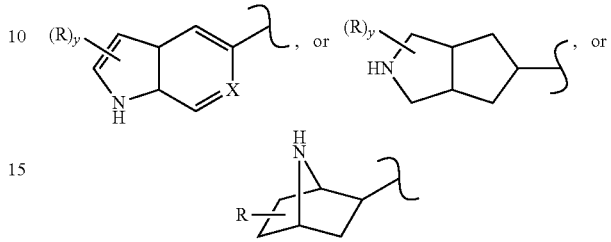

then, unless otherwise defined, a substituent "R" can reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group can reside on either the 5-membered or the 6-membered ring of the fused ring system. In the formula depicted above, when y is 2 for example, then the two "R's" can reside on any two atoms of the ring system, again assuming each replaces a depicted, implied, or expressly defined hydrogen on the ring.

When a group "R" is depicted as existing on a ring system containing saturated carbons, as for example in the formula:

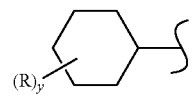

where, in this example, "y" can be more than one, assuming each replaces a currently depicted, implied, or expressly defined hydrogen on the ring; then, unless otherwise defined, where the resulting structure is stable, two "R's" can reside on the same carbon. A simple example is when R is a methyl group; there can exist a geminal dimethyl on a carbon of the depicted ring (an "annular" carbon). In another example, two R's on the same carbon, including that carbon, can form a ring, thus creating a spirocyclic ring (a "spirocyclyl" group) structure with the depicted ring as for example in the formula:

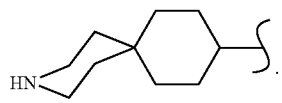

"(C$_1$-C$_6$)alkyl" is intended to mean C$_1$-C$_6$ linear or branched structures and combinations thereof, inclusively. For example, "C$_6$ alkyl" can refer to an n-hexyl, iso-hexyl, and the like. (C$_1$-C$_6$)alkyl is intended to include (C$_1$-C$_4$)alkyl and (C$_1$-C$_3$)alkyl without limitation. Examples of (C$_1$-C$_6$) alkyl groups include methyl, ethyl, propyl, isopropyl, butyl, s-butyl, t-butyl, isobutyl, pentyl, hexyl and the like. In this application, alkyl refers to alkanyl, alkenyl, and alkynyl residues (and combinations thereof); it is intended to include vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl.

"$(C_3\text{-}C_{10})$cycloalkyl" means a non-aromatic mono- or multicyclic ring system comprising about 3 to 10 carbon atoms. $(C_3\text{-}C_{10})$cycloalkyl is intended to include $(C_5\text{-}C_6)$cycloalkyl. Non-limiting examples of monocyclic cycloalkyls include cyclopropyl, cyclopentyl, cyclohexyl, cycloheptyl and the like. Non-limiting examples of multicyclic cycloalkyls include 1-decalin, norbornyl, adamantyl and the like. Cycloalkyls can be fused or bridge ring systems or spirocyclic systems.

"Alkylene" is a subset of alkyl and refers to straight or branched chain divalent group consisting solely of carbon and hydrogen atoms, containing no unsaturation and having from one to six carbon atoms, for example, methylene, ethylene, propylene, n-butylene and the like. Alkylene refers to the same residues as alkyl, but having two points of attachment and, specifically, fully saturated. Examples of alkylene include ethylene ($-CH_2CH_2-$), propylene ($-CH_2CH_2CH_2-$), and dimethylpropylene ($-CH_2C(CH_3)_2CH_2-$).

"alkylene," when optionally substituted, can contain alkyl substitution which itself contains unsaturation. For example, 2-(2-phenylethynyl-but-3-enyl)-naphthalene (IUPAC name) contains an n-butylid-3-ynyl group with a vinyl substituent at the 2-position of said group.

"$(C_1\text{-}C_6)$alkoxy" refers to the group $O-(C_1\text{-}C_6)$alkyl, wherein the term "$(C_1\text{-}C_6)$alkyl" is as defined hereinabove. "$(C_1\text{-}C_6)$alkoxy" is intended to include $(C_1\text{-}C_3)$alkoxy. Examples include methoxy, ethoxy, propoxy, isopropoxy, and the like.

"$(C_6\text{-}C_{10})$aryl" means a monovalent five- to ten-membered mono- or multicyclic ring, wherein the monocyclic ring is aromatic and at least one of the rings in the multicyclic ring is aromatic. Representative non-limiting examples of aryl include phenyl, naphthyl, and indanyl, and the like.

"$-(C_1\text{-}C_6)$alkyl-$(C_6\text{-}C_{10})$aryl," is intended to mean a $(C_6\text{-}C_{10})$aryl moiety attached to a parent structure via $(C_1\text{-}C_6)$ alkylene group. Examples include benzyl, phenethyl, and the like.

In some examples, as appreciated by one of ordinary skill in the art, two adjacent groups on an aromatic system can be fused together to form a ring structure. The fused ring structure can contain heteroatoms and can be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems includes non-aromatic and aromatic systems. Typically, but not necessarily, fused-polycyclics share a vicinal set of atoms, for example naphthalene or 1,2,3,4-tetrahydro-naphthalene. A Spiro ring system is not a fused-polycyclic by this definition, but fused polycyclic ring systems of the invention can themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl groups that are substituted with one or more halogens, respectively. Non-limiting examples of "haloalkyl" include $-CH_2F$, $-CHCl_2$ or $-CF_3$.

"Heteroatom" refers to O, S, N, or P.

"(4-10 membered)heterocycloalkyl" refers to a stable four- to ten-membered ring substituent that consists of carbon atoms and from one to five heteroatoms selected from the nitrogen, phosphorus, oxygen and sulfur. For purposes of this invention, the heterocycloalkyl substituent can be a monocyclic or a multicyclic ring system, which can include fused or bridged ring systems as well as spirocyclic systems. "(4-10 membered)heterocycloalkyl" is intended to include, without limitation, (4-6 membered)heterocycloalkyl.

"(5-10 membered)heteroaryl" refers to a stable five- to ten-membered ring substituent that consists of carbon atoms and from one to five heteroatoms selected from the nitrogen, phosphorus, oxygen and sulfur. For purposes of this invention, the heteroaryl substituent can be a monocyclic or a multicyclic ring system, which can include fused or bridged ring systems as well as spirocyclic systems. (5-10 membered) heteroaryl is intended to include, without limitation, (5-6 membered)heteroaryl.

In the above heteroaryl and heterocycloalkyl substituents, the nitrogen, phosphorus, carbon or sulfur atoms can be optionally oxidized to various oxidation states. In a specific example, the group $-S(O)_{0-2}-$, refers to $-S-$ (sulfide), $-S(O)-$ (sulfoxide), and $-SO_2-$ (sulfone) respectively. For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms can be optionally quaternized; and the ring substituent can be partially or fully saturated or aromatic.

Non-limiting examples of (4-10 membered)heterocycloalkyl and (5-10 membered)heteroaryl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, tetrahydrofuranyl, tetrahydroisoquinolinyl, and tetrahydroquinolinyl.

Representative examples of "(5-10 membered)heteroaryl" include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzdioxolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Fused, bridged, and spiro moieties are also included within the scope of this definition.

When a group is referred to as "$-(C_1\text{-}C_6)$alkyl-(4-10 membered)heterocycloalkyl" the heterocycloalkyl is attached to a parent structure via one of an alkylene, alkylidene, or alkylidyne group. Examples include (4-methylpiperazin-1-yl)methyl, (morpholin-4-yl)methyl, (pyridine-4-yl) methyl, 2-(oxazolin-2-yl)ethyl, 4-(4-methylpiperazin-1-yl)-

2-butenyl, and the like. Both the heterocyclyl and the corresponding alkylene, alkylidene, or alkylidyne portion of a heterocyclylalkyl group can be optionally substituted.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" means substituted or unsubstituted and refers to all subsequent modifiers in a term unless otherwise specified.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

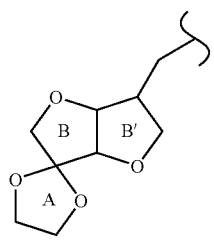

Some of the compounds of the invention can have imino, amino, oxo or hydroxy substituents off aromatic heterocyclyl systems. For purposes of this disclosure, it is understood that such imino, amino, oxo or hydroxy substituents can exist in their corresponding tautomeric form, i.e., amino, imino, hydroxy or oxo, respectively.

The compounds of the invention, or their pharmaceutically acceptable salts, can have asymmetric carbon atoms, oxidized sulfur atoms or quaternized nitrogen atoms in their structure.

The compounds of the invention and their pharmaceutically acceptable salts can exist as single stereoisomers, racemates, and as mixtures of enantiomers and diastereomers. The compounds can also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that theoretically some constructs which would not normally be considered as stable compounds (that is, sterically practical and/or synthetically feasible, supra).

When a particular group with its bonding structure is denoted as being bonded to two partners; that is, a divalent group, for example, —OCH$_2$—, then it is understood that either of the two partners can be bound to the particular group at one end, and the other partner is necessarily bound to the other end of the particular group, unless stated explicitly otherwise. Stated another way, divalent groups are not to be construed as limited to the depicted orientation, for example.

"—OCH$_2$—" is meant to mean not only "—OCH$_2$—" as drawn, but also "—CH$_2$O—."

In addition to the various embodiments recited hereinabove, also encompassed by this invention are combinations of the embodiments described herein.

Methods for the preparation and/or separation and isolation of single stereoisomers from racemic mixtures or non-racemic mixtures of stereoisomers are well known in the art. For example, optically active (R)- and (S)-isomers can be prepared using chiral synthons or chiral reagents, or resolved using conventional techniques. Enantiomers (R- and S-isomers) can be resolved by methods known to one of ordinary skill in the art, for example by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step can be required to liberate the desired enantiomeric form. Alternatively, specific enantiomer can be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer can be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, can also modulate, either directly or indirectly, phosphatase activity. This additional modulation, if present, can be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt can be the biologically active form of the compound in the body. In one example, a prodrug can be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention. All compounds of this invention described in all aspects and embodiments herein are intended to include both solvated and unsolvated forms thereof.

It is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition can be necessary, and will be ascertainable with routine experimentation by one of ordinary skill in the art.

One of ordinary skill in the art would understand that certain crystallized, protein-ligand complexes, in particular CK2-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods can be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods can further entail: performing rational drug design with the model of the three-dimensional structure, and selecting a potential candidate agent in conjunction with computer modeling.

Additionally, one skilled in the art would appreciate that such methods can further entail: employing a candidate agent, so-determined to fit spatially into the ligand binding domain, in a biological activity assay for kinase modulation, and determining whether said candidate agent modulates kinase activity in the assay. Such methods can also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method can be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

In the another aspect, the invention provides pharmaceutical compositions comprising an inhibitor of CK2 according to the invention and a pharmaceutically acceptable carrier, excipient, or diluent. In other embodiments, administration can preferably be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions can include a conventional pharmaceutical carrier or excipient and a compound of the invention as the/an active agent, and, in addition, can include other medicinal agents, pharmaceutical agents, carriers, adjuvants, etc. Compositions of the invention can be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It can also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention can also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid dosage forms as described above can be prepared with coatings and shells, such as enteric coatings and others well known in the art. They can contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, can contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with, for example, suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as can be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example CK2, the protein is bound to a support, and a compound of the invention is added to the assay. Alternatively, the compound of the invention is bound to the support and the protein is added. Classes of candidate agents among which novel binding agents can be sought include specific antibodies, non-natural binding agents identified in screens of chemical libraries, peptide analogs, etc. Of particular interest are screening assays for candidate agents that have a low toxicity for human cells. A wide variety of assays can be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, CK2 can be done in a number of ways. In one example, the candidate agent (the compound of the invention) is labeled, for example, with a fluorescent or radioactive moiety and binding determined directly. For example, this can be done by attaching all or a portion of the CK2 protein to a solid support, adding a labeled agent (for example a compound of the invention in which at least one atom has been replaced by a detectable isotope), washing off excess reagent, and determining whether the amount of the label is that present on the solid support. Various blocking and washing steps can be utilized as is known in the art.

The term "labeled" as used herein is meant to include both direct and indirect labeling with a compound that provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, CK2 protein can be labeled at tyrosine positions using $^{125}$I, or with fluorophores. Alternatively, more than one component can be labeled with different labels; using $^{125}$I for the proteins, for example, and a fluorophor for the candidate agents.

The compounds of the invention can also be used as competitors to screen for additional drug candidates. The terms "candidate bioactive agent" or "drug candidate" or grammatical equivalents as used herein describe any molecule, e.g., protein, oligopeptide, small organic molecule, polysaccharide, polynucleotide, etc., to be tested for bioactivity. They can be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to CK2.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to IGF1R, such as an antibody, peptide, binding partner, ligand, etc. Under certain circumstances, there can be competitive binding as between the candidate agent and the binding moiety, with the binding moiety displacing the candidate agent.

In some embodiments, the candidate agent is labeled. Either the candidate agent, or the competitor, or both, is added first to CK2 protein for a time sufficient to allow binding, if present. Incubations can be performed at any temperature that facilitates optimal activity, typically between 4° C. and 40° C.

Incubation periods are selected for optimum activity, but can also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to CK2 and thus is capable of binding to, and potentially modulating, the activity of the CK2. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor can indicate the candidate agent is bound to CK2 with a higher affinity. Thus, if the candidate agent is labeled, the presence of the label on the support, coupled with a lack of competitor binding, can indicate the candidate agent is capable of binding to CK2.

It can be of value to identify the binding site of CK2. This can be done in a variety of ways. In one embodiment, once CK2 is identified as binding to the candidate agent, the CK2 is fragmented or modified and the assays repeated to identify the necessary components for binding.

Modulation is tested by screening for candidate agents capable of modulating the activity of CK2 comprising the steps of combining a candidate agent with CK2, as above, and determining an alteration in the biological activity of the CK2. Thus, in this embodiment, the candidate agent should both bind to (although this can not be necessary), and alter its biological or biochemical activity as defined herein. The methods include both in vitro screening methods and in vivo screening of cells for alterations in cell viability, morphology, and the like.

Alternatively, differential screening can be used to identify drug candidates that bind to native CK2, but cannot bind to modified CK2.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which can be used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components can be added in any order that provides for the requisite binding.

One of ordinary skill in the art would understand that certain crystallized, protein-ligand complexes, in particular CK2-ligand complexes, and their corresponding x-ray structure coordinates can be used to reveal new structural information useful for understanding the biological activity of CK2 kinases as described herein. As well, the key structural features of the aforementioned proteins, particularly, the shape of the ligand binding site, are useful in methods for designing or identifying selective modulators of CK2 kinases and in solving the structures of other proteins with similar features. Ligands of such complexes can include compounds of the invention as described herein.

As well, one of ordinary skill in the art would appreciate that such suitable x-ray quality crystals can be used as part of a method of identifying a candidate agent capable of binding to and modulating the activity of CK2 kinases. Such methods can be characterized by the following aspects: a) introducing into a suitable computer program, information defining a ligand binding domain of a CK2 kinase in a conformation (e.g. as defined by x-ray structure coordinates obtained from suitable x-ray quality crystals as described above) the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods can further entail: performing rational drug design with the model of the three-dimensional structure, and selecting a potential candidate agent in conjunction with computer modeling.

Additionally, one skilled in the art would appreciate that such methods can further entail: employing a candidate agent, so-determined to fit spatially into the ligand binding domain, in a biological activity assay for CK2 kinase modulation, and determining whether said candidate agent modulates CK2 kinase activity in the assay. Such methods can also include administering the candidate agent, determined to modulate CK2 kinase activity, to a mammal suffering from a condition treatable by CK2 kinase modulation, such as those described above.

Also, one skilled in the art would appreciate that compounds of the invention can be used in a method of evaluating the ability of a test agent to associate with a molecule or molecular complex comprising a ligand binding domain of a CK2 kinase. Such a method can be characterized by the following aspects: a) creating a computer model of a CK2 kinase binding pocket using structure coordinates obtained from suitable x-ray quality crystals of the CK2 kinase, b) employing computational algorithms to perform a fitting operation between the test agent and the computer model of the binding pocket, and c) analyzing the results of the fitting operation to quantify the association between the test agent and the computer model of the binding pocket.

Synthetic Procedures

Generally, the compounds listed below were identified by LC-MS, and/or isolated, and characterized by $^1$H-NMR (most typically 400 MHz). Liquid chromatography-mass spectral (LC-MS) analyses were performed using at least one of: a Hewlett-Packard Series 1100 MSD, an Agilent 1100 Series LC/MSD (available from Agilent Technologies Deutschland GmbH of Waldbronn Germany), or a Waters 8-Channel MUX System (available from Waters Corporation of Milford, Mass.). Compounds were identified according to either their observed mass [M+1] or [M+Na] ion (positive mode) or [M−1] ion (negative mode). $^1$H-NMR data for compounds was taken with a Varian AS400 Spectrometer (400 MHz, available from Varian GmbH, Darmstadt, Germany).

Compound Synthesis

Examples

The following examples serve to provide further appreciation of the invention, but are not meant in any way to restrict the effective scope of the invention.

Compound Synthesis:

Compounds of the invention that are of the 4,6-diarylpyrimidin-2(1H)-one and 4,6-diarylpyrimidon-2(1H)-one classes can be synthesized by the synthetic route outlined in Scheme 1. Thus, commercially available 1H-indazole-5-carbaldehyde (1), or another heterocyclic aldehyde, is condensed with a suitably functionalized —C(O)—($C_6$-$C_{10}$)aryl such as benzophenone (2).

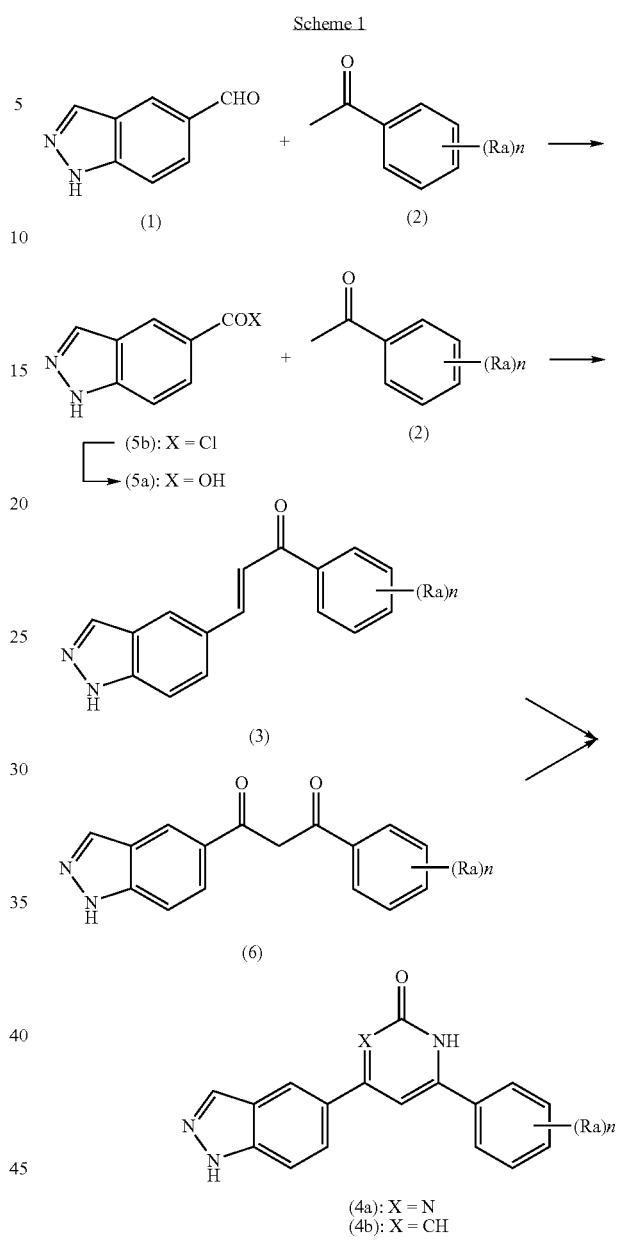

wherein Ra is independently selected from —O($C_1$-$C_6$)alkyl-$R_4$, —NH($C_1$-$C_6$)alkyl-$R_5$, —N[($C_1$-$C_6$)alkyl]($C_1$-$C_6$)alkyl-$R_6$, —O($C_1$-$C_6$)alkenyl-$R_7$, —O($C_1$-$C_6$)alkynyl-$R_8$, —OH, —OCF$_3$, —($C_1$-$C_6$)alkyl and halo;
and n is 0, 1, 2 or 3.

The condensation reaction is typically carried out in the presence of a base such as NaOH to give a chalcone (3). Reaction with urea under acidic conditions with heating affords a pyrimidin-2(1H)-one (4a), or with acetamidoacetomide (or with 2-(1H-benzo[d][1,2,3]-triazol-1-yl)acetamide) under basic condition to give pyridin-2(1H)-one (4b). (Wang, S.; Yu, G.; Lu, J.; Xiao, K.; Hu, Y.; Hu, H. Synthesis 2003, 4, 487-490; Katritzky, A. R.; et al. J. Org. Chem. 1997, 62, 6210-6214). Alternatively, the synthesis can be carried out thorough the preparation of a diketone intermediate (6). Thus, benzoic acid (5a) is converted into the corresponding chloroanhydride (5b) and condensed with a suitably functionalized benzophenone. The condensation is typically carried out in the presence of a base such as LiHMDS to give a diketone intermediate (6). Reaction with urea under acidic condition with heating affords a pyrimidin-2(1H)-one (4a).

Scheme 2

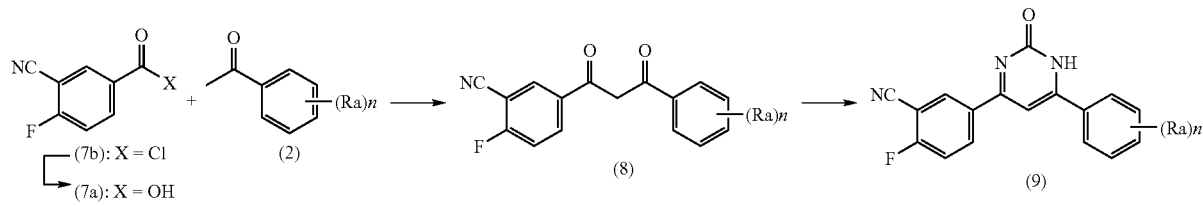

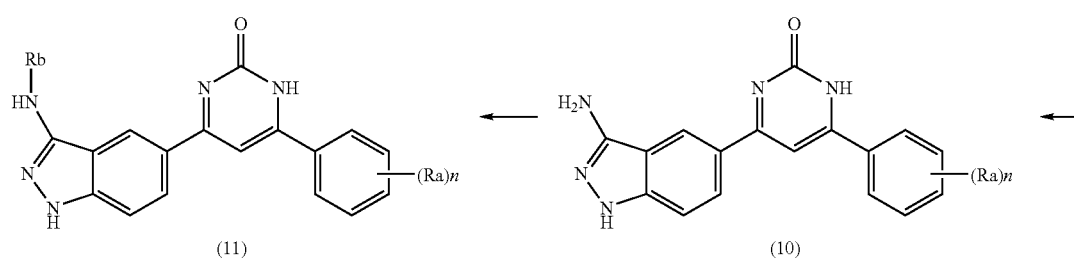

wherein Ra independently selected from
—O(C$_1$-C$_6$)alkyl-R$_4$, —NH(C$_1$-C$_6$)alkyl-R$_5$, —N[(C$_1$-C$_6$)alkyl](C$_1$-C$_6$)alkyl-R$_6$, —O(C$_1$-C$_6$)alkenyl-R$_7$, —O(C$_1$-C$_6$)alkynyl-R$_8$, —OH, —OCF$_3$, —(C$_1$-C$_6$)alkyl and halo; and n is 0, 1, 2 or 3.

Scheme 2 illustrates the general method of synthesis for compounds of the invention with aminoindazole moiety. In this instance commercially available 3-cyano-4-fluorobenzoic acid (7a) is converted into the corresponding chloroanhydride (7b) and condensed with a suitably functionalized benzophenone (2). The condensation is typically carried out in the presence of a base such as LiHMDS to give a diketone intermediate (8). Reaction with urea under acidic conditions with heating affords a pyrimidin-2(1H)-one (9). The resulting cyanofluoro substituted phenyl can then be converted to a corresponding aminoindazole (10) by treatment with hydrazine hydrate, and can be further derivatised by the means of reductive alkylation or acylation (11).

EXAMPLES

Example 1

4-(3-amino-1H-indazol-5-yl)-6-{2-[(2-methylpropyl)oxy]phenyl}pyrimidin-2(1H)-one Scheme 3

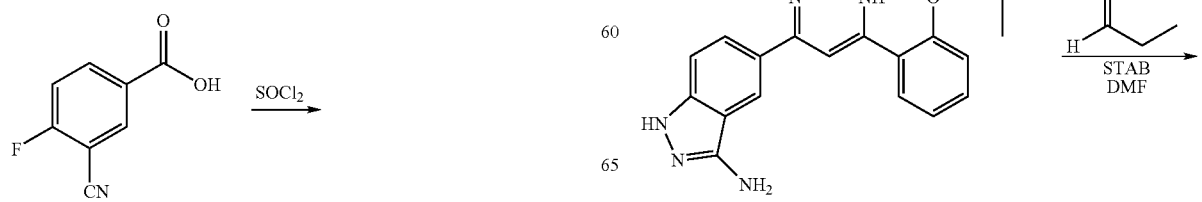

-continued

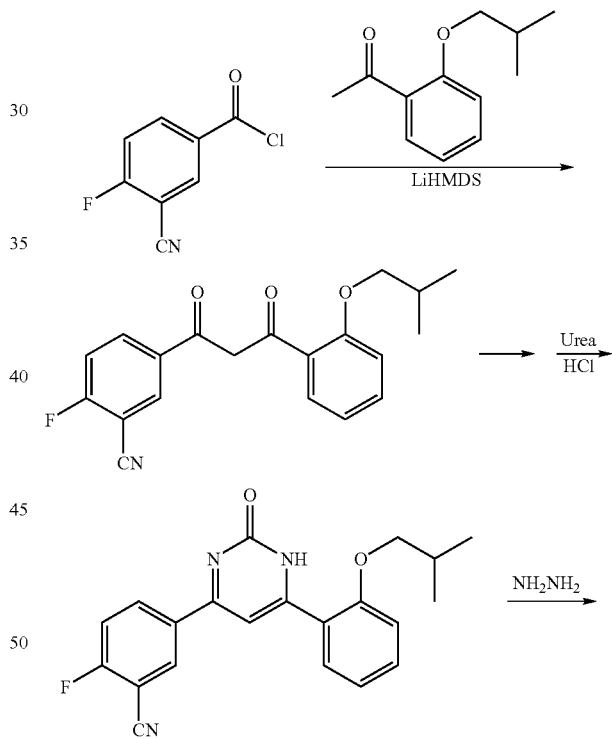

-continued

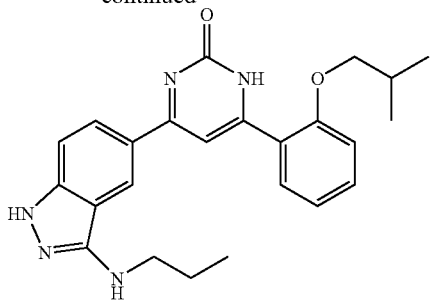

Step 1

1-(2-isobutoxyphenyl)ethanone

To a sealed vessel were added commercially available 1-(2-hydroxyphenyl)ethanone (54.4 g, 0.4 mol), acetonitrile (300 mL), commercially available 1-bromo-2-methyl propane (56.5 mL, 0.52 mol) and potassium carbonate (72 g, 0.52 mol). The reaction mixture was heated in an oil bath at 90° C. for 16 h, concentrated in vacuo then partitioned between ethyl acetate and water. The layers were separated and the aqueous layer was extracted with ethyl acetate. The combined organic layers were dried over anhydrous magnesium sulfate, filtered and concentrated in vacuo. Vacuum distillation resulted in 40.0 (55%) g 1-(2-isobutoxyphenyl)ethanone. $^1$H NMR (400 MHz, CDCl$_3$): δ 7.72 (d, 1H), 7.42 (t, 1H), 6.95 (dd, 2H), 3.90 (d, 2H), 2.63 (s, 3H), 2.18-2.10 (m, 1H), 1.05 (d, 6H).

Step 2

3-cyano-4-fluorobenzoyl chloride

In a 250 mL round bottom flask a mixture of 3-cyano-4-fluorobenzoic acid (7.75 g, 0.047 mol) and thionyl chloride (28 mL, 0.38 mol, 8 eq) was heated to 80° C. for 1 h. The reaction mixture was concentrated in vacuo to give 8.6 g of 3-cyano-4-fluorobenzoyl chloride which can be used in the next step without further purification. $^1$H NMR (400 MHz, CDCl$_3$): δ 8.49-8.43 (m, 1H), 8.42-8.36 (m, 1H), 7.44 (t, 1H).

Step 3

2-fluoro-5-(3-(2-isobutoxyphenyl)-3-oxopropanoyl)benzonitrile

To a solution of 1-(2-isobutoxyphenyl)ethanone (9.0 g, 0.047 mol) in tetrahydrofuran (150 mL) under N$_2$ at −78° C. was added a 1.0 M solution of lithium hexamethyl disilazide in hexanes (100 mL, 2.2 eq) over 5 minutes. The reaction was stirred at −78° C. for 1 h. To the reaction solution was added 3-cyano-4-fluorobenzoyl chloride (8.6 g, 0.047 mmol) in tetrahydrofuran (28 mL) over 5 minutes at −78° C. The reaction mixture was then removed from the dry ice bath and allowed to stir for 1 h. The reaction was quenched with 1N HCl then partitioned between ethyl acetate and water. The layers were separated and the aqueous layer was extracted with ethyl acetate. The combined organic layers were dried over anhydrous magnesium sulfate, filtered and concentrated in vacuo. The resulting solid was triturated with acetonitrile and filtered yielding 10.9 g (90%) of 2-fluoro-5-(3-(2-isobutoxyphenyl)-3-oxopropanoyl)benzonitrile and was submitted to the next step without further purification.

Step 4

2-fluoro-5-(6-(2-isobutoxyphenyl)-2-oxo-1,2-dihydropyrimidin-4-yl)benzonitrile

To a sealed vessel were added 2-fluoro-5-(3-(2-isobutoxyphenyl)-3-oxopropanoyl)benzonitrile (5.9 g, 17.4 mmol), urea (10 g) and a solution of 4 N HCl in dioxane (80 mL). The reaction mixture was heated at 115° C. for 4 h then cooled. More urea (10 g) and 4 N HCl in dioxane (50 mL) were added to the vessel and the reaction was again heated to 115° C. for 4 h. Upon cooling, a precipitate formed and the reaction mixture was filtered in vacuo. The filtrate was determined by LC/MS to contain the desired product and was concentrated in vacuo. The concentrated reaction mixture was dissolved in dichloromethane (100 mL) and was neutralized with a solution of saturated sodium bicarbonate and was then partitioned between dichloromethane and water. The layers were separated and the aqueous layer was extracted with dichloromethane. The combined organic layers were dried over anhydrous magnesium sulfate, filtered and concentrated in vacuo yielding 1.1 g crude 2-fluoro-5-(6-(2-isobutoxyphenyl)-2-oxo-1,2-dihydropyrimidin-4-yl)benzonitrile and was submitted to the next step with no further purification.

Step 5

4-(3-amino-1H-indazol-5-yl)-6-{2-[(2-methylpropyl)oxy]phenyl}pyrimidin-2(1H)-one To a sealed vessel were added 2-fluoro-5-(6-(5-fluoro-2-isobutoxyphenyl)-2-oxo-1,2-dihydropyrimidin-4-yl)benzonitrile (900 mg), butanol (15 mL) and hydrazine hydrate (5 mL). The reaction mixture was heated to 115° C. for 3 h. Upon cooling the mixture was concentrated in vacuo and dissolved in methanol. Formation of product was confirmed by LC/MS and the product was purified by preparatory HPLC (reverse-phase, acetonitrile/water with 0.1% formic acid) to yield 200 mg (98%) of the title compound: $^1$H-NMR (400 MHz, d6-DMSO): δ 8.84 (s, 1H), 8.11 (d, 1H), 7.67 (d, 1H), 7.56-7.63 (m, 1H), 7.44 (d, 1H), 7.31 (s, 1H), 7.25 (d, 1H), 7.11-7.18 (m, 1H), 3.88 (d, 2H), 1.95-2.10 (m, 1H), 0.94 (d, 6H). MS (EI) for C$_{21}$H$_{21}$N$_5$O$_2$: 375 (MH$^+$).

Example 2

6-{2-[(2-methylpropyl)oxy]phenyl}-4-[3-(propylamino)-1H-indazol-5-yl]pyrimidin-2(1H)-one In a 5 mL round bottom flask a mixture of 4-(3-amino-1H-indazol-5-yl)-6-{2-[(2-methylpropyl)oxy]phenyl}pyrimidin-2(1H)-one from Example 1 (100 mg, 0.26 mmol), propional (150 mg, 2.6 mmol), AcOH (1 drop) and 5 mL DMF were heated to 50° C. for 1 h, then sodium triacetoxyborohydrate (0.5 g 2.6 mmol) was added. The resulting slurry was stirred at room temperature for 24 h then concentrated under vacuo. The product was purified by preparatory HPLC to yield 15 mg (14%) of 6-{2-[(2-methylpropyl)oxy]phenyl}-4-[3-(propylamino)-1H-indazol-5-yl]pyrimidin-2(1H)-one mono HCl salt. $^1$H-NMR (400 MHz, d6-DMSO): δ 8.81 (s, 1H), 8.08 (d, 1H), 7.67 (d, 1H), 7.67 (d, 1H), 7.59 (t, 1H), 7.39 (d, 1H), 7.26 (m, 2H), 7.15 (t, 1H), 3.88 (d, 2H), 2.03 (m, 1H), 1.65 (m, 2H), 0.97 (d, 3H), 0.94 (d, 6H). MS (EI) for C$_{24}$H$_{27}$N$_5$O$_2$: 418 (MH$^+$).

Example 3

4-[3-({[3-(methyloxy)phenyl]methyl}amino)-1H-indazol-5-yl]-6-{2-[(2-methylpropyl)oxy]phenyl}pyrimidin-2(1H)-one To a 50 mL round bottom flask were added commercially available 4-(3-amino-1H-indazol-5-yl)-6-(2-isobutoxyphenyl)pyrimidin-2(1H)-one (130 mg, 0.35 mmol), m-anisaldehyde (420 µL, 3.5 mmol, 10 eq), dimethylformamide (10 mL) and glacial acetic acid (10 drops). The reaction mixture was heated to 50° C. in an oil bath and stirred for 1 h. The mixture was allowed to cool before adding sodium cyanoborohydride (1M THF solution (Aldrich), 3 mL, 3 mmol) and subsequently stirred at room temperature for 1 h. Formation of product was confirmed by LC/MS and was purified by preparatory HPLC (reverse-phase, acetonitrile/water with 0.1% formic acid) to yield 40 mg (98%) of the title compound: $^1$H-NMR (400 MHz, d6-DMSO): δ 11.78 (s, 1H), 11.64 (s, 1H), 8.73 (s, 1H), 8.06 (d, 1H), 7.60 (d, 1H), 7.46-7.54 (m, 1H), 7.28-7.34 (m, 1H), 7.15-7.26 (m, 2H), 7.06-7.12 (m, 1H), 6.96-7.01 (m, 1H), 6.73-6.81 (m, 1H), 4.42-4.48 (m, 2H), 3.82-3.88 (m, 2H), 3.72 (s, 3H), 1.94-2.07 (m, 1H), 0.90-0.95 (m, 6H). MS (EI) for $C_{29}H_{29}N_5O_3$: 495 (MH$^+$).

Example 4

4-{3-[(cyclopropylmethyl)amino]-1H-indazol-5-yl}-6-{2-[(2-methylpropyl)oxy]phenyl}pyrimidin-2(1H)-one To a 50 mL round bottom flask were added commercially available 4-(3-amino-1H-indazol-5-yl)-6-(2-isobutoxyphenyl)pyrimidin-2(1H)-one (83 mg, 0.22 mmol), cyclopropanecarbaldehyde (150 mg, 2.2 mmol), THF (10 mL) and glacial acetic acid (2 drops). The reaction mixture was heated to 45° C. and stirred for 1 h then concentrated under reduced pressure. The resulting solid was dissolved in 3 mL of THF which was followed by the addition of sodium cyanoborohydride (1M THF solution (Aldrich), 3 mL, 3 mmol). The reaction mixture was stirred at room temperature for 1 h. Formation of product was confirmed by LC/MS and the product was purified by preparatory HPLC (reverse-phase, acetonitrile/water with 0.1% formic acid) to yield 20 mg (21%) of the HCl salt of the title compound: $^1$H-NMR (400 MHz, d6-DMSO): δ 8.87 (s, 1H), 8.07 (s, 1H), 7.68 (d, 1H), 7.62 (t, 1H), 7.41 (d, 1H), 7.33 (br s, 1H), 7.26 (d, 1H), 7.16 (t, 1H), 3.76 (d, 2H), 3.19 (d, 2H), 2.05 (m, 1H), 1.15 (m, 1H), 0.95 (d, 6H), 0.50 (dd, 2H), 0.27 (dd, 2H). MS (EI) for $C_{25}H_{27}N_5O_2$: 430 (MH$^+$).

Example 5

4-(3-{[(4-fluorophenyl)methyl]amino}-1H-indazol-5-yl)-6-{2-[(2-methylpropyl)oxy]phenyl}pyrimidin-2(1H)-one 4-(3-{[(4-fluorophenyl)methyl]amino}-1H-indazol-5-yl)-6-{2-[(2-methylpropyl)oxy]phenyl}pyrimidin-2(1H)-one was prepared by a procedure analogous to Example 4, in which commercially available 4-fluorobenzaldehyde was substituted for cyclopropanecarbaldehyde. $^1$H-NMR (400 MHz, d6-DMSO): δ 11.78 (s, 1H), 7.60 (br s, 1H), 7.50 (t, 1H), 7.45 (m, 2H), 7.31 (d, 1H), 7.18-7.07 (m, 5H), 6.81 (t, 1H), 6.57 (br s, 1H), 4.47 (d, 2H), 3.85 (d, 2H), 2.01 (m, 1H), 0.93 (d, 6H). MS (EI) for $C_{28}H_{26}FN_5O_2$: 484 (MH$^+$).

Example 6

6-phenyl-4-[3-(propylamino)-1H-indazol-5-yl]pyrimidin-2(1H)-one 6-phenyl-4-[3-(propylamino)-1H-indazol-5-yl]pyrimidin-2(1H)-one was prepared by a procedure analogous to Examples 1 and 2, in which commercially available acetophenone was substituted for 1-(2-isobutoxyphenyl)ethanone. NMR (400 MHz, d6-DMSO): δ 8.90 (s, 1H), 8.15-8.05 (m, 2H), 7.65-7.43 (m, 5H), 3.70 (t, 2H), 1.78-1.65 (m, 2H), 0.95 (t, 3H). MS (EI) for $C_{20}H_{19}N_5O$: 346 (MH$^+$).

Example 7

4-(3-amino-1H-indazol-5-yl)-6-[2-(propyloxy)phenyl]pyrimidin-2(1H)-one 4-(3-amino-1H-indazol-5-yl)-6-[2-(propyloxy)phenyl]pyrimidin-2(1H)-one was prepared by a procedure analogous to Example 1, in which commercially available 1-bromopropane was substituted for 1-bromo-2-methyl propane. $^1$H NMR (400 MHz, d6-DMSO): δ 8.60 (s, 2H), 8.00 (s, 1H), 7.62-7.42 (m, 2H), 7.23 (d, 1H), 7.18-7.02 (m, 3H), 5.58 (s, 2H), 4.00 (t, 2H), 1.77-1.68 (m, 2H), 0.95 (t, 2H). MS (EI) for $C_{20}H_{19}N_5O_2$: 362 (MH$^+$).

Example 8

4-(3-amino-1H-indazol-5-yl)-6-{2-[(piperidin-4-ylmethyl)oxy]phenyl}pyrimidin-2(1H)-one 4-(3-amino-1H-indazol-5-yl)-6-{2-[(piperidin-4-ylmethyl)oxy]phenyl}pyrimidin-2(1H)-one was prepared by a procedure analogous to Example 1, in which commercially available tert-butyl 4-((2-acetylphenoxy)methyl)piperidine-1-carboxylate was substituted for 1-bromo-2-methyl propane. tert-Butyl 4-((2-acetylphenoxy)methyl)piperidine-1-carboxylate was prepared by the procedure below. 4-(3-amino-1H-indazol-5-yl)-6-{2-[(piperidin-4-ylmethyl)oxy]phenyl}pyrimidin-2(1H)-one was isolated after treatment of the Boc protected precursor with 4N HCl/Dioxane (Aldrich) for 10 h in MeOH. Preparatory HPLC (reverse-phase, acetonitrile/water with 0.1% formic acid) purification resulted in the title compound. $^1$H NMR (400 MHz, d6-DMSO): δ 8.73 (s, 1H), 8.64 (s, 1H), 8.02 (d, 1H), 7.62 (d, 1H), 7.50 (t, 1H), 7.36 (d, 1H), 7.25-7.07 (m, 3H), 5.62 (s, 1H), 3.95 (d, 2H), 3.20-3.05 (m, 2H), 2.78-2.63 (m, 2H), 2.06-2.00 (m, 1H), 1.88-1.75 (m, 3H), 1.50-1.35 (m, 2H). MS (EI) for $C_{23}H_{24}N_6O_2$: 417 (MH$^+$).

tert-butyl 4-((2-acetylphenoxy)methyl)piperidine-1-carboxylate

To a solution of 2'-hydroxyacetophenone (2.72 g, 20 mmol), commercially available 1-Boc-4-(hydroxymethyl)piperidine (4.28 g, 20 mmol) and triphenylphosphine (5.76 g, 22 mmol) in dichloromethane (80 mL), diisopropylazodicarboxylate (4.75 mL, 24 mmol) were added dropwise at 0° C. The solution was stirred at room temperature for 4 hours, then quenched with water, extracted with dichloromethane, dried with sodium sulfate, filtered, and concentrated under reduced pressure. The residue was purified by column chromatography to give a colorless oil, which slowly solidified to result in tert-butyl 4-((2-acetylphenoxy)-methyl)piperidine-1-carboxylate (3.6 g, 54%). $^1$H NMR (400 MHz, CDCl$_3$): δ 7.75 (d, 2H), 7.46 (t, 1H), 7.00 (t, 1H), 6.95 (d, 1H), 4.22-4.10 (m, 2H), 3.93 (d, 2H), 2.80-2.75 (m, 2H), 2.18 (s, 3H), 2.08-2.00 (m, 1H), 1.85-1.80 (m, 2H) 1.44 (s, 9H), 1.40-1.23 (m, 2H).

Example 9

4-(3-amino-1H-indazol-5-yl)-6-{2-[(cyclopropylmethyl)oxy]phenyl}pyrimidin-2(1H)-one 4-(3-amino-1H-indazol-5-yl)-6-{2-[(cyclopropylmethyl)oxy]phenyl}pyrimidin-2(1H)-one was prepared by a procedure analogous to Example 1, in which commercially available (bromomethyl)cyclopropane was substituted for 1-bromo-2-methyl propane. Step 4 and Step 5 resulted in 4-(3-amino-1H-indazol-5-yl)-6-{2-[(cyclopropylmethyl)oxy]phenyl}pyrimidin-2(1H)-one and 4-(3-amino-1H-indazol-5-yl)-6-(2-hydroxyphenyl)pyrimidin-2(1H)-one. 4-(3-amino-1H-indazol-5-yl)-6-{2-[(cyclopropylmethyl)oxy]phenyl}pyrimidin-2(1H)-one was separated by preparatory HPLC (reverse-phase, acetonitrile/water with 0.1% formic acid). $^1$H NMR (400 MHz, d6-DMSO): δ 8.63 (s, 1H), 8.20 (s, 1H), 8.03 (d, 1H), 7.64-7.58 (m, 1H), 7.46 (t, 1H), 7.35-7.20 (m, 2H), 7.18 (d, 1H), 7.05 (t, 1H), 5.60 (s, 2H), 3.96 (d, 2H), 1.30-1.18 (m, 1H), 0.55-0.45 (d, 2H), 0.35-0.30 (d, 2H), 0.95 (t, 3H). MS (EI) for $C_{21}H_{19}N_5O_2$: 374 (MH$^+$).

Example 10

4-(3-amino-1H-indazol-5-yl)-6-(2-hydroxyphenyl)pyrimidin-2(1H)-one 4-(3-amino-1H-indazol-5-yl)-6-(2-hydroxyphenyl)pyrimidin-2(1H)-one was isolated as a byproduct in the synthesis of 4-(3-amino-1H-indazol-5-yl)-6-{2-[(cyclopropylmethyl)oxy]-phenyl}pyrimidin-2(1H)-one (EXAMPLE 9). $^1$H NMR (400 MHz, d6-DMSO): δ 8.58 (s, 1H), 8.04 (d, 1H), 7.97 (d, 1H), 7.40-7.28 (m, 3H), 6.82-6.75 (m, 2H), 5.60 (s, 2H). MS (EI) for $C_{17}H_{13}N_5O_2$: 320 (MH$^+$).

Example 11

4-(3-amino-1H-indazol-5-yl)-6-{2-[(trifluoromethyl)oxy]phenyl}pyrimidin-2(1H)-one 4-(3-amino-1H-indazol-5-yl)-6-{2-[(trifluoromethyl)oxy]phenyl}pyrimidin-2(1H)-one was prepared by a procedure analogous to Example 1, in which commercially available 1-(2-(trifluoromethoxy)phenyl)ethanone was substituted for 1-(2-isobutoxyphenyl)ethanone. $^1$H NMR (400 MHz, d6-DMSO): δ 8.64 (s, 1H), 8.03 (d, 1H), 7.80 (d, 1H), 7.75-7.66 (m, 1H), 7.63-7.58 (m, 1H), 7.35 (d, 1H), 7.15 (s, 1H), 5.62 (s, 2H). MS (EI) for $C_{18}H_{12}F_3N_5O_2$: 388 (MH$^+$).

Example 12

4-(3-amino-1H-indazol-5-yl)-6-[3-(methyloxy)phenyl]pyrimidin-2(1H)-one 4-(3-amino-1H-indazol-5-yl)-6-[3-(methyloxy)phenyl]pyrimidin-2(1H)-one was prepared by a procedure analogous to Example 1, in which commercially available 1-(3-methoxyphenyl)ethanone was substituted for 1-(2-hydroxyphenyl)ethanone. $^1$H NMR (400 MHz, d6-DMSO): δ 11.80 (s, 2H), 8.65 (s, 1H), 8.03 (s, 1H), 7.70-7.60 (m, 2H), 7.50-7.38 (m, 2H), 7.35 (d, 1H), 7.17 (d, 1H), 5.62 (s, 2H), 3.88 (s, 3H). MS (EI) for $C_{18}H_{15}N_5O_2$: 334 (MH$^+$).

Example 13

4-(3-amino-1H-indazol-5-yl)-6-[2-(methyloxy)phenyl]pyrimidin-2(1H)-one 4-(3-amino-1H-indazol-5-yl)-6-[2-(methyloxy)phenyl]pyrimidin-2(1H)-one was prepared by a procedure analogous to Example 1, in which commercially available 1-(2-methoxyphenyl)ethanone was substituted for 1-(2-isobutoxyphenyl)ethanone. $^1$H NMR (400 MHz, d6-DMSO): δ 8.63 (s, 1H), 8.05 (d, 1H), 7.58 (d, 1H), 7.52 (t, 1H), 7.32 (d, 1H), 7.20 (d, 1H), 7.11 (t, 1H), 7.08 (s, 1H), 5.62 (s, 2H), 3.84 (s, 3H). MS (EI) for $C_{18}H_{15}N_5O_2$: 334 (MH$^±$).

Example 14

4-(3-amino-1H-indazol-5-yl)-6-[3-[(2-methylpropyl)oxy]pyrimidin-2(1H)-one 4-(3-amino-1H-indazol-5-yl)-6-[3-[(2-methylpropyl)oxy]pyrimidin-2(1H)-one was prepared by a procedure analogous to Example 1, in which commercially available 1-(3-hydroxyphenyl)ethanone was substituted for 1-(2-hydroxyphenyl)ethanone. $^1$H-NMR (400 MHz, d6-DMSO): δ 11.80 (s, 2H), 8.70 (s, 1H), 8.04 (d, 1H), 7.65-7.60 (m, 2H), 7.47-7.38 (m, 2H), 7.37 (d, 1H), 7.18 (d, 1H), 5.62 (s, 2H), 3.85 (d, 2H), 2.10-2.00 (m, 1H), 1.01 (d, 6H). MS (EI) for $C_{21}H_{21}N_5O_2$: 376 (MH$^+$).

Example 15

4-(3-amino-1H-indazol-5-yl)-6-{3-[(cyclohexylmethyl)oxy]phenyl}pyrimidin-2(1H)-one 4-(3-amino-1H-indazol-5-yl)-6-{3-[(cyclohexylmethyl)oxy]phenyl}pyrimidin-2(1H)-one was prepared by a procedure analogous to Example 1, in which commercially available 1-(3-hydroxyphenyl)ethanone was substituted for 1-(2-hydroxyphenyl)ethanone and (bromomethyl)cyclohexane was substituted for 1-bromo-2-methylpropane. $^1$H NMR (400 MHz, d6-DMSO): δ 8.90 (s, 1H), 8.18 (d, 1H), 7.70-7.60 (m, 2H), 7.55-7.39 (m, 3H), 7.20 (d, 1H), 3.98 (d, 2H), 1.95-1.80 (m, 5H), 1.37-1.05 (m, 41-1). MS (EI) for $C_{24}H_{25}N_5O_2$: 416 (MH$^+$).

Example 16

4-(3-amino-1H-indazol-5-yl)-1,5-dihydro-2H-indeno[1,2-d]pyrimidin-2-one 4-(3-amino-1H-indazol-5-yl)-1,5-dihydro-2H-indeno[1,2-d]pyrimidin-2-one was prepared by a procedure analogous to Example 1, in which commercially available 2,3-dihydro-1H-inden-1-one was substituted for 1-(2-isobutoxyphenyl)ethanone. $^1$H NMR (400 MHz, d6-DMSO): δ 8.65 (s, 1H), 8.40 (d, 1H), 7.90-7.75 (m, 3H), 7.68-7.62 (m, 1H), 7.53 (d, 1H), 4.36 (s, 2H). MS (EI) for $C_{18}H_{13}N_5O$: 316 (MH$^+$).

Example 17

4-(3-amino-1H-indazol-5-yl)-6-{5-(methyloxy)-2-[(2-methylpropyl) oxy]phenyl}pyrimidin-2(1H)-one 4-(3-amino-1H-indazol-5-yl)-6-{5-(methyloxy)-2-[(2-methylpropyl)oxy]phenyl}pyrimidin-2(1H)-one was prepared by a procedure analogous to Example 1, in which commercially available 1-(2-hydroxy-5-methoxyphenyl)

ethanone was substituted for 1-(2-hydroxyphenyl)ethanone. ¹H NMR (400 MHz, d6-DMSO): δ 8.66 (s, 2H), 8.0 (d, 2H), 7.58-7.05 (m, 5H), 3.80 (s, 3H), 3.45 (d, 2H), 2.01-1.96 (m, 1H), 0.98 (d, 6H). MS (EI) for $C_{22}H_{23}N_5O_3$: 406 (MH$^+$).

Example 18

4-(3-amino-1H-indazol-5-yl)-6-{4-fluoro-2-[(2-methylpropyl)oxy]phenyl}pyrimidin-2(1H)-one 4-(3-amino-1H-indazol-5-yl)-6-{4-fluoro-2-[(2-methylpropyl)oxy]phenyl}pyrimidin-2(1H)-one was prepared by a procedure analogous to Example 1, in which commercially available 1-(4-fluoro-2-hydroxyphenyl)ethanone was substituted for 1-(2-hydroxyphenyl)-ethanone. ¹H NMR (400 MHz, d6-DMSO): δ 8.62 (s, 1H), 8.00 (d, 1H), 7.70 (t, 1H), 7.32 (d, 1H), 7.18-7.05 (m, 2H), 6.98-6.94 (m, 1H), 5.60 (s, 1H), 3.83 (d, 2H), 2.05-1.98 (m, 1H), 0.98 (d, 6H). MS (EI) for $C_{21}H_{20}FN_5O_2$: 394 (MH$^±$).

Example 19

4-(3-amino-1H-indazol-5-yl)-6-{5-fluoro-2-[(2-methylpropyl)oxy]phenyl}pyrimidin-2(1H)-one 4-(3-amino-1H-indazol-5-yl)-6-{5-fluoro-2-[(2-methylpropyl)oxy]phenyl}-pyrimidin-2(1H)-one was prepared by a procedure analogous to Example 1, in which commercially available 1-(5-fluoro-2-hydroxyphenyl)ethanone was substituted for 1-(2-hydroxyphenyl)ethanone. ¹H-NMR (400 MHz, d6-DMSO): δ 11.72 (s, 1H), 8.61 (s, 1H), 8.02 (s, 1H), 7.48-7.58 (m, 1H), 7.27-7.43 (m, 1H), 7.16-7.25 (m, 1H), 6.56 (s, 1H), 5.63 (s, 1H), 3.82-3.88 (m, 2H), 1.96-2.10 (m, 1H), 0.86-1.02 (m, 6H). MS (EI) for $C_{21}H_{20}N_5O_2$: 393 (MH$^+$).

Example 20

4-(3-amino-1H-indazol-5-yl)-6-{5-chloro-2-[(2-methylpropyl)oxy]phenyl}pyrimidin-2(1H)-one 4-(3-amino-1H-indazol-5-yl)-6-{5-chloro-2-[(2-methylpropyl)oxy]phenyl}-pyrimidin-2(1H)-one was prepared by a procedure analogous to Example 1, in which commercially available 1-(5-chloro-2-hydroxyphenyl)ethanone was substituted for 1-(2-hydroxyphenyl)ethanone. ¹H-NMR (400 MHz, d6-DMSO): δ 11.75 (s, 1H), 8.64 (s, 1H), 8.03 (d, 1H), 7.72 (s, 1H), 7.56 (d, 1H), 7.31 (d, 1H), 7.23 (d, 1H), 5.67 (s, br, 2H), 3.86 (s, 2H), 1.95-2.10 (m, 1H), 0.90-0.96 (m, 6H). MS (EI) for $C_{21}H_{20}N_5O_2$: 409 (MH$^+$).

Example 21

4-(3-amino-1H-indazol-5-yl)-6-{2-(methyloxy)-6-[(2-methylpropyl)oxy]phenyl}pyrimidin-2(1H)-one 4-(3-amino-1H-indazol-5-yl)-6-{2-(methyloxy)-6-[(2-methylpropyl)oxy]phenyl}-pyrimidin-2(1H)-one was prepared by a procedure analogous to Example 1, in which commercially available 2'-hydroxy-6-methoxyacetophenone was substituted for 1-(2-hydroxyphenyl)ethanone. ¹H NMR (400 MHz, d6-DMSO): δ 8.61 (s, 1H), 8.15 (d, 1H), 7.46 (t, 1H), 7.38 (d, 1H), 7.06 (s, 1H), 6.79 (d 1H), 6.75 (d, 1H), 3.84 (s, 3H), 3.79 (d, 2H), 1.95 (m, 1H), 0.95 (d, 6H). MS (EI) for $C_{22}H_{25}N_5O_3$: 406 (MH$^±$).

Example 22

4-(3-amino-1H-indazol-5-yl)-6-{3-[(2-methylpropyl)oxy]-4-pyridyl}pyrimidin-2(1H)-one 4-(3-amino-1H-indazol-5-yl)-6-{3-[(2-methylpropyl)oxy]-4-pyridyl}pyrimidin-2(1H)-one was prepared by a procedure analogous to Example 1, in which commercially available 1-(3-isobutoxypyridin-4-yl)ethanone was substituted for 1-(2-isobutoxyphenyl)-ethanone. The synthesis of 1-(3-isobutoxypyridin-4-yl)ethanone is described below. ¹H-NMR (400 MHz, d6-DMSO): δ 8.63 (s, 1H), 8.58 (s, 1H), 8.36 (d, 1H), 8.00 (d, 1H), 7.66 (d, 1H), 7.30 (d, 2H), 5.60 (m, 2H), 4.01 (d, 2H), 2.04 (m, 1H), 0.94 (d, 6H). MS (EI) for $C_{20}H_{20}N_6O_2$: 377 (MH$^+$).

1-(3-isobutoxypyridin-4-yl)ethanone

Step 1

3-isobutoxyisonicotinic acid

Sodium metal (7.3 g, 0.32 mol) was added in small portions to 2-methyl-1-propanol (145 mL, 0.63 mol) at 80° C. over 30 min period, and the reaction mixture was stirred for an additional 3 h at 80° C. Subsequently, a solution of commercially available 3-chloroisonicotinic acid (10 g, 63 mmol) in 5 mL of DMSO was added to the reaction mixture at 80° C. The resulting slurry was heated to 120° C. for an additional 16 h, then cooled down to room temperature, concentrated down to half volume under the reduced pressure, and filtered. The filtrate was concentrated down to half volume under the reduced pressure, and filtered again. The combined solids were mixed with 10 mL of MeOH and 1 mL of water and acidified with concentrated HCl at 0° C. to pH=7. The resulting precipitate was filtered out and dried under vacuum, resulting in 10 g (81%) of 3-isobutoxyisonicotinic acid. ¹H-NMR (400 MHz, d6-DMSO): δ 8.47 (s, 1H), 8.23 (d, 1H), 7.46 (d, 1H), 3.91 (d, 2H), 2.04 (m, 1H), 0.94 (d, 6H). MS (EI) for $C_{10}H_{13}NO_3$: 196 (MH$^+$).

Step 2

3-isobutoxy-N-methoxy-N-methylisonicotinamide

A mixture of 3-isobutoxyisonicotinic acid (2.2 g, 11.2 mmol) and oxalyl chloride (7 g, 55 mmol) in 25 mL of dichloromethane was stirred at room temperature for 1 h. The resulting solution was concentrated down under reduced pressure and the residue was re-dissolved in 50 mL of dichloromethane. To this solution were added N,O-dimethylhydroxyl-amine hydrochloride (4.5 g, 46.4 mmol) and pyridine (5 mL) at 0° C. The reaction was allowed to warm up to room temperature over 30 min period, and quenched with 2 mL of water. The resulting mixture was bacified with 1 mL 10% KOH solution (pH=10), the layers were separated, and the aqueous layer was washed twice with 20 mL portions of dichloromethane. The combined dichloromethane washes were dried over sodium sulfate, and concentrated down under reduced pressure, resulting in 1.8 g (67%) of 3-isobutoxy-N-methoxy-N-methylisonicotinamide. ¹H-NMR (400 MHz, d6-DMSO): δ 8.46 (s, 1H), 8.25 (d, 1H), 7.45 (d, 1H), 3.96 (d, 2H), 3.43 (s, 3H), 2.76 (d, 3H), 2.05 (m, 1H), 0.94 (d, 6H). MS (EI) for $C_{12}H_{18}N_2O_2$: 239 (MH$^+$).

Step 3

1-(3-isobutoxypyridin-4-yl)ethanone

Methyl lithium (4.6 mL, 7.4 mmol, 1.6M in Et$_2$O, Aldrich) was added dropwise to a solution of 3-isobutoxy-N-methoxy-N-methylisonicotinamide (0.88 g, 3.7 mmol) in 15 mL of THF at 0° C. The reaction mixture was allowed to stir at 0° C. for an additional 1 h. To the resulting mixture were added 1 mL of water and 2 drops of conc HCl. The layers were separated and the aqueous layer was washed twice with 20 mL portions of Et$_2$O. The combined organic layers were washed with brine, dried over sodium sulfate, and concentrated under reduced pressure. The product was purified by SiO$_2$ flash chromatography (50:50 hexanes/ethyl acetate) to 450 mg (63%) of the title compound. $^1$H-NMR (400 MHz, d6-DMSO): δ 8.54 (s, 1H), 8.27 (d, 1H), 7.41 (d, 1H), 4.01 (d, 2H), 2.55 (s, 3H), 2.06 (m, 1H), 0.99 (d, 6H). MS (EI) for C$_{12}$H$_{18}$N$_2$O$_2$: 194 (MH$^+$).

Example 23

4-(3-amino-1,2-benzisoxazol-5-yl)-6-{2-[(2-methylpropyl)oxy]phenyl}pyrimidin-2(1H)-one To a solution of acetohydroxamic acid (53 mg, 0.7 mmol) in DMF (5 mL) was added potassium tert-butoxide (80 mg, 1.76 mmol). The mixture was stirred at room temperature for 20 min, followed by the addition of solution of 2-fluoro-5-(6-(2-isobutoxyphenyl)-2-oxo-1,2-dihydropyrimidin-4-yl) benzonitrile (100 mg, 0.27 mmol) (Example 1, Step 4) in DMF (4 mL). The reaction was stirred at room temperature for 16 h. The mixture was quenched by acid and the product was purified by Prep-HPLC to give 75 mg (74%) of 4-(3-amino-1,2-benzisoxazol-5-yl)-6-{2-[(2-methylpropyl)oxy] phenyl}pyrimidin-2(1H)-one. $^1$H NMR (400 MHz, d6-DMSO): δ 11.80 (s, br, 2H), 8.78 (s, 1H), 8.37 (d, 1H), 7.66-7.45 (m, 3H), 7.24-7.00 (m, 3H), 6.60 (s, 2H), 3.83 (d, 2H), 2.05-1.97 (m, 1H), 0.98 (d, 6H). MS (EI) for C$_{21}$H$_{20}$N$_4$O$_3$: 377 (MH$^+$).

Example 24

4-[3-(methylamino)-1H-indazol-5-yl]-6-{2-[(2-methylpropyl)oxy]phenyl}pyrimidin-2(1H)-one To a 5 mL round bottom flask were added commercially available 4-(3-amino-1H-indazol-5-yl)-6-(2-isobutoxyphenyl)pyrimidin-2(1H)-one (100 mg, 0.26 mmol), formaldehyde (0.12 g of 37% H$_2$O solution, 1.6 mmol), dimethylformamide (2 mL) and glacial acetic acid (1 drop). The reaction mixture was stirred at room temperature for 1 h, after which time sodium cyanoborohydride (1M THF solution (Aldrich), 2 mL, 2 mmol) was added. The reaction mixture was stirred at room temperature for an additional 1 h. Formation of product was confirmed by LC/MS and the product was purified by preparatory HPLC (reverse-phase, acetonitrile/water with 0.1% formic acid) to yield 25 mg (25%) of the title compound. $^1$H-NMR (400 MHz, d6-DMSO): δ 11.78 (s, 1H), 8.62 (s, 1H), 8.04 (d, 1H), 7.61 (d, 1H), 7.49 (t, 1H), 7.30 (d, 1H), 7.19 (d, 1H), 7.10 (m, 2H), 6.23 (q, 1H), 3.85 (d, 2H), 2.86 (d, 3H), 2.01 (m, 1H), 0.93 (d, 6H). MS (EI) for C$_{22}$H$_{23}$N$_5$O$_2$: 390 (MH$^+$).

Example 25

6-{2-[(2-methylpropyl)oxy]phenyl}-4-{3-[(phenylmethyl)amino]-1H-indazol-5-yl}pyrimidin-2(1H)-one 6-{2-[(2-methylpropyl)oxy]phenyl}-4-{3-[(phenylmethyl)amino]-$^1$H-indazol-5-yl}pyrimidin-2(1H)-one was prepared by a procedure analogous to Example 4, in which commercially available benzaldehyde was substituted for cyclopropanecarbaldehyde. $^1$H-NMR (400 MHz, d6-DMSO): δ 11.78 (s, 1H), 8.74 (s, 1H), 8.05 (d, 1H), 7.61 (d, 1H), 7.49 (m, 1H), 7.42 (d, 2H), 7.31 (m, 3H), 7.20 (m, 2H), 7.12 (d, 1H), 7.08 (d, 1H), 6.79 (t, 1H), 4.49 (d, 2H), 3.85 (d, 2H), 2.02 (m, 1H), 0.93 (d, 6H). MS (EI) for C$_{28}$H$_{27}$N$_5$O$_2$: 466.5543 (MH+).

Example 26

4-(3-{[(4-bromophenyl)methyl]amino}-1H-indazol-5-yl)-6-{2-[(2-methylpropyl)oxy]phenyl}pyrimidin-2(1H)-one 4-(3-{[(4-bromophenyl)methyl]amino}-1H-indazol-5-yl)-6-{2-[(2-methylpropyl)-oxy]phenyl}pyrimidin-2(1H)-one was prepared by a procedure analogous to Example 4, in which commercially available 4-bromobenaldehyde was substituted for cyclopropane-carbaldehyde. $^1$H-NMR (400 MHz, d6-DMSO): δ 11.79 (s, 1H), 8.72 (s, 1H), 8.05 (d, 1H), 7.61 (d, 1H), 7.50 (d, 3H), 7.37 (d, 2H), 7.31 (d, 1H), 7.18 (d, 1H), 7.12 (d, 1H), 7.08 (d, 1H), 6.88 (t, 1H), 4.45 (d, 2H), 3.85 (d, 2H), 2.02 (m, 1H), 0.93 (d, 6H). MS (EI) for C$_{28}$H$_{26}$BrN$_5$O$_2$: 545.4 (MH+).

Example 27

6-{2-[(2-methylpropyl)oxy]phenyl}-4-{3-[(piperidin-4-ylmethyl)amino]-1H-indazol-5-yl}pyrimidin-2(1H)-one 6-{2-[(2-methylpropyl)oxy]phenyl}-4-{3-[(piperidin-4-ylmethyl)amino]-1H-indazol-5-yl}pyrimidin-2(1H)-one was prepared by a procedure analogous to Example 4, in which commercially available tert-butyl 4-formylpiperidine-1-carboxylate was substituted for cyclopropanecarbaldehyde. The resulting product was dissolved in 10 mL of MeOH and 5 mL of 4N HCl/Dioxane (Aldrich). The reaction mixture was heated to 50° C. for 15 min, concentrated under reduced pressure and purified by preparatory HPLC, resulting in 19 mg of the title compound. $^1$H-NMR (400 MHz, d6-DMSO): δ 11.73 (s, 1H), 8.70 (br s, 1H), 8.41 (s, 1H), 8.02 (d, 1H), 7.61 (d, 1H), 7.49 (t, 1H), 7.30 (d, 2H), 7.19 (d, 1H), 7.11 (m, 2H), 6.34 (t, 1H), 3.86 (d, 2H), 3.16 (m, 5H), 2.67 (m, 2H), 2.01 (m, 1H), 1.82 (m, 2H), 1.23 (m, 2H), 0.92 (d, 6H). MS (EI) for C$_{27}$H$_{32}$N$_6$O$_2$: 473 (MH$^+$).

Example 28

4-{3-[(2-aminoethyl)amino]-1H-indazol-5-yl}-6-{2-[(2-methylpropyl)oxy]phenyl}pyrimidin-2(1H)-one 4-{3-[(2-aminoethyl)amino]-1H-indazol-5-yl}-6-{2-[(2-methylpropyl)oxy]-phenyl}pyrimidin-2(1H)-one mono AcOH was prepared by a procedure analogous to Example 27, in which commercially available tert-butyl 2-oxoethylcarbamate was substituted for tert-butyl 4-formylpiperidine-1-carboxylate. $^1$H-NMR (400 MHz, d6-DMSO): δ 8.68 (br s, 1H), 8.04 (d, 1H), 7.61 (d, 1H), 7.49 (t, 1H), 7.31 (d, 2H), 7.19 (d, 1H), 7.13 (s, 1H), 7.09 (t, 1H), 6.32 (m, 1H), 3.85 (d, 2H), 3.4 (br s, DMSO), 2.67 (m, 2H), 2.01 (m, 1H), 1.82 (s, 3H, AcOH), 0.93 (d, 6H). MS (EI) for C$_{23}$H$_{26}$N$_6$O$_2$: 419 (MH$^+$).

Example 29

N'2',N'2'-dimethyl-N-(2-{[5-(6-{2-[(2-methylpropyl)oxy]phenyl}-2-oxo-1,2-dihydropyrimidin-4-yl)-1H-indazol-3-yl]amino}ethyl)glycinamide To a solution of 4-{3-[(2-aminoethyl)amino]-1H-indazol-5-yl}-6-{2-[(2-methylpropyl)oxy]phenyl}pyrimidin-2(1H)-one (12 mg, 0.028 mmol) in dimethylacetamide (1 mL) and diisopropylethylamine (14 mg, 0.14 mmol) was added 2-dimethylaminoacetic acid (10 mg, 0.056 mmol) followed by HATU (53 mg, 0.4 mmol). The reaction mixture was stirred at room temperature for 2 h. Formation of product was confirmed by LC/MS and the product was purified by preparatory HPLC (reverse-phase, acetonitrile/water with 0.1% formic acid) to yield 2 mg (14%) of the title compound. MS (EI) for C$_{27}$H$_{33}$N$_7$O$_3$: 504 (MH$^+$).

Example 30

N-[5-(6-{2-[(2-methylpropyl)oxy]phenyl}-2-oxo-1,2-dihydropyrimidin-4-yl)-1H-indazol-3-yl]propanamide To a solution of commercially available 4-(3-amino-1H-indazol-5-yl)-6-(2-isobutoxyphenyl)pyrimidin-2(1H)-one (60 mg, 0.15 mmol) in dimethylacetamide (4 mL) and diisopropylethylamine (130 pt, 0.76 mmol, 5 eq) was added propionic acid (56 μL, 0.76 mmol, 5 eq) followed by HATU (290 mg, 0.76 mmol, 5 eq). The reaction mixture was stirred at room temperature for 16 h. Formation of product was confirmed by LC/MS and the product was purified by preparatory HPLC (reverse-phase, acetonitrile/water with 0.1% formic acid) to yield 17 mg (26%) of the title compound: $^1$H-NMR (400 MHz, d6-DMSO): δ 11.85 (s, 1H), 8.79 (s, 1H), 8.28-8.35 (m, 1H), 7.64 (s, 1H), 7.49-7.58 (m, 1H), 7.20 (d, 1H), 7.08-7.13 (m, 1H), 6.63 (s, 2H), 4.07-4.14 (m, 1H), 3.83-3.91 (m, 2H), 3.15-3.19 (m, 1H), 2.93-3.03 (m, 2H), 1.95-2.08 (m, 1H), 1.14-1.21 (m, 3H), 0.90-0.96 (m, 6H). MS (EI) for $C_{24}H_{25}N_5O_3$: 431 (MH$^+$).

Example 31

N'2',N'2'-dimethyl-N-[5-(6-{2-[(2-methylpropyl)oxy]phenyl}-2-oxo-1,2-dihydropyrimidin-4-yl)-1H-indazol-3-yl]glycinamide N'2',N'2'-dimethyl-N-[5-(6-{2-[(2-methylpropyl)oxy]phenyl}-2-oxo-1,2-dihydropyrimidin-4-yl)-1H-indazol-3-yl]glycinamide was prepared with 97% yield by a procedure analogous to Example 30, in which commercially available N'N'-dimethyl glycine was substituted for propionic acid. $^1$H-NMR (400 MHz, d6-DMSO): δ 11.91 (s, 1H), 8.84 (s, 1H), 8.39 (m, 1H), 8.29 (d, 1H), 7.63 (m, 1H), 7.53 (t, 1H), 7.22 (d, 1H), 7.25-6.85 (br s, 1H), 7.13 (t, 1H), 6.81 (s, 2H), 4.36 (br s, 2H), 3.87 (d, 2H), 2.68 (s, 6H), 2.02 (m, 1H), 0.92 (d, 6H). MS (EI) for $C_{25}H_{28}N_6O_3$: 461 (MH$^+$).

Example 32

4-(1,3-benzodioxol-5-yl)-6-{2-[(2-methylpropyl)oxy]phenyl}pyrimidin-2(1H)-one

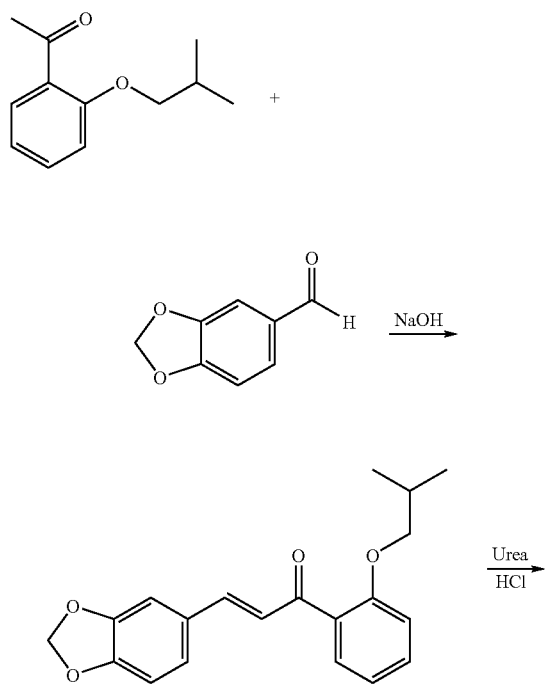

Scheme 4

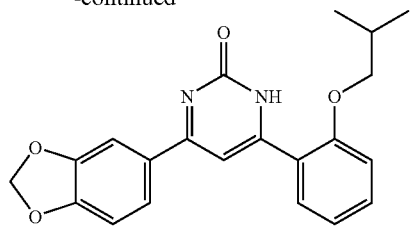

Step 1

(E)-3-(benzo[d][1,3]dioxol-5-yl)-1-(2-isobutoxyphenyl)prop-2-en-1-one

To a round bottomed flask was added EtOH (20 mL) and potassium hydroxide (320.0 mg, 8 mmol). The mixture was stirred until homogeneous before benzo[d][1,3]dioxole-5-carbaldehyde (0.83 mL, 4.0 mmol) and 1-(2-isobutoxyphenyl)ethanone (770 mg, 4 mmol) were added. The reaction was stirred at room temperature for 16 h, and 5 mL of water was added. The reaction mixture was acidified with 1N HCl until pH=6. The resulting orange precipitate was filtered and submitted to the next step without further purification. MS (EI) for $C_{20}H_{20}O_4$: 325 (MH$^+$).

Step 2

4-(1,3-benzodioxol-5-yl)-6-{2-[(2-methylpropyl)oxy]phenyl}pyrimidin-2(1H)-one

To a sealed pressure vessel were added (E)-3-(benzo[d][1,3]dioxol-5-yl)-1-(2-isobutoxyphenyl)prop-2-en-1-one (256 mg, 0.8 mmol), 4N HCl in dioxanes (5 mL), and urea (242 mg, 4 mmol). The pressure vessel was sealed and heated to 120° C. for 20 h. Another 200 mg of urea were added and heated for another 5 h. The reaction was then cooled to room temperature, concentrated under reduced pressure and the product was purified by preparative HPLC to result in 10 mg (34%) of the title compound. $^1$H-NMR (400 MHz, d6-DMSO): δ 7.74 (d, 1H), 7.67 (d, 1H), 7.63 (d, 1H), 7.50 (m, 1H), 7.18 (d, 2H), 7.05-7.10 (m, 2H), 3.85 (dd, 2H), 2.02 (m, 1H), 0.95 (d, 6H). MS (EI) for $C_{21}H_{20}N_2O_4$: 364 (MH$^+$).

Example 33

4-(1-benzofuran-2-yl)-6-{2-[(2-methylpropyl)oxy]phenyl}pyrimidin-2(1H)-one 4-(1-benzofuran-2-yl)-6-{2-[(2-methylpropyl)oxy]phenyl}pyrimidin-2(1H)-one was prepared by a procedure analogous to Example 32, in which commercially available benzofuran-2-carbaldehyde was substituted for benzo[d][1,3]dioxole-5-carbaldehyde. $^1$H-NMR (400 MHz, d6-DMSO): δ 7.82 (t, 1H), 7.76 (d, 1H), 7.66 (d, 1H), 7.51 (m, 2H), 7.35 (t, 1H), 7.20 (d, 1H), 7.12 (t, 1H), 6.82 (s, 1H), 3.91 (d, 2H), 2.07 (m, 1H), 1.03 (d, 6H). MS (EI) for $C_{22}H_{20}N_2O_3$: 361 (MH$^+$).

Example 34

6-[5-(2-chlorophenyl)furan-2-yl]-4-{2-[(2-methylpropyl)oxy]phenyl}pyrimidin-2(1H)-one 6-[5-(2-chlorophenyl)furan-2-yl]-4-{2-[(2-methylpropyl)oxy]phenyl}pyrimidin-2(1H)-one was prepared by a procedure analogous to Example 32, in which commercially available 5-(2-chlorophenyl)furan-2-carbaldehyde was substituted for benzo[d][1,3]dioxole-5-carbaldehyde. $^1$H-NMR (400 MHz, d6-DMSO): δ 8.04 (dd, 1H), 7.68 (s, 1H), 7.62 (dd, 1H), 7.58 (s, 1H), 7.49 (m, 3H), 7.38 (d, 1H), 7.19 (d, 1H), 7.09 (t, 1H), 3.88 (d, 2H), 2.05 (m, 1H), 1.229 (s, 1H), 0.95 (d, 6H). MS (EI) for $C_{24}H_{21}ClN_2O_3$: 420.894 (MH$^+$).

Example 35

6-{2-[(2-methylpropyl)oxy]phenyl}-4-(5-phenylfuran-2-yl)pyrimidin-2(1H)-one

6-{2-[(2-methylpropyl)oxy]phenyl}-4-(5-phenylfuran-2-yl)pyrimidin-2(1H)-one was prepared by a procedure analogous to Example 33, in which commercially available 5-phenylfuran-2-carbaldehyde was substituted for benzo[d][1,3]dioxole-5-carbaldehyde. $^1$H-NMR (400 MHz, d6-DMSO): δ 7.89 (d, 2H), 7.47-7.54 (m, 4H), 7.40 (t, 2H), 7.26 (d, 1H), 7.20 (d, 1H), 7.10 (t, 2H), 6.55 (s, 1H), 3.90 (d, 2H), 2.07 (m, 1H), 0.98 (d, 61-1). MS (EI) for $C_{24}H_{22}N_2O_3$: 387 (MH$^+$).

Example 36

4-(3-methyl-1H-indazol-5-yl)-6-{2-methyl-4-[(piperidin-4-ylmethyl)amino]phenyl}pyrimidin-2(1H)-one Scheme 5

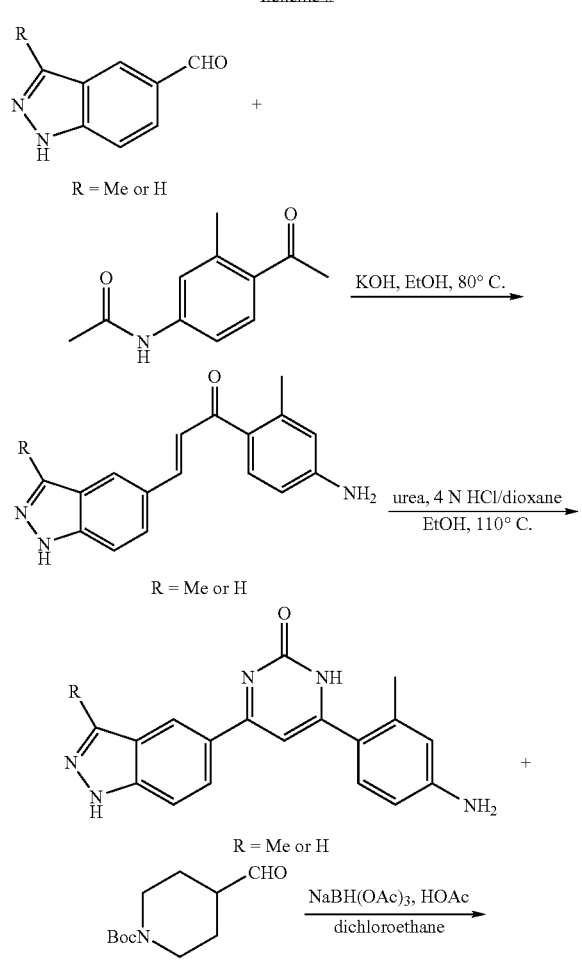

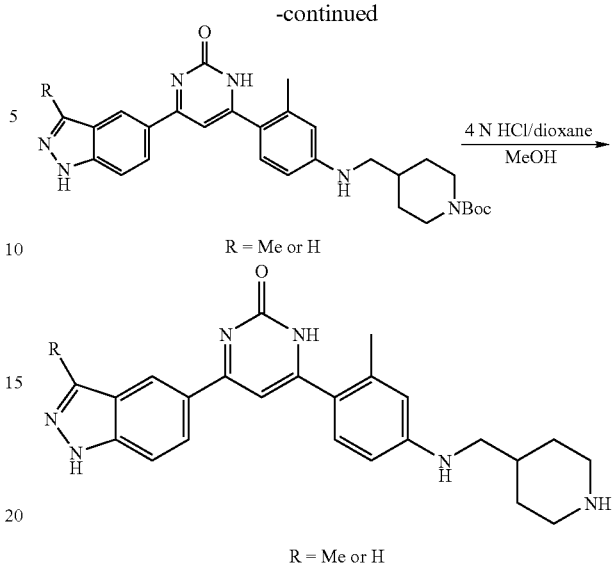

R = Me or H

Step 1

(E)-1-(4-amino-2-methylphenyl)-3-(3-methyl-1H-indazol-5-yl)prop-2-en-1-one

To a solution of KOH (1.5 g, 26 mmol) in 20 mL ethanol were added 3-methyl-1H-indazole-5-carbaldehyde (see Note 1 for synthesis) (0.850 g, 5.3 mmol) and commercially available N-(4-acetyl-3-methylphenyl)acetamide (1.0 g, 5.3 mmol). The reaction mixture was heated to 80° C. for 24 hours and then cooled down to room temperature. After acidification with 1N HCl, the mixture was brought to pH 8 with saturated aqueous NaHCO$_3$ and extracted twice with ethyl acetate (2×100 mL). The combined organic phases were washed with brine, dried over Na$_2$SO$_4$, filtered, and concentrated in vacuo. The product was purified by SiO$_2$ flash chromatography (60:40 to 50:50 hexanes/ethyl acetate) to afford (E)-1-(4-amino-2-methylphenyl)-3-(3-methyl-1H-indazol-5-yl)prop-2-en-1-one (0.500 g, 32%). $^1$H NMR (400 MHz, d$_6$-DMSO): δ 12.8 (s, 1H), 8.12 (s, 1H), 7.81 (dd, 1H), 7.78 (d, 1H), 7.61 (d, 2H), 7.48 (d, 1H), 6.45 (m, 2H), 5.88 (br s, 1H), 3.06 (s, 3H), 2.42 (s, 3H); MS (EI) for $C_{18}H_{17}N_3O$: 292.3 (MH$^+$).

Note 1: 3-methyl-1H-indazole-5-carbaldehyde and 1H-indazole-5-carbaldehyde were synthesized according to a patent published by Piatnitski, Evgueni; Kiselyov, Alexander. Heteroaryl aminophenyl ketone derivatives and their preparation and use as kinase inhibitors, e.g., in the treatment of neoplastic diseases. PCT Int. Appl. (2005), 58 pp. CODEN: PIXXD2 WO 2005000813 A1 20050106 CAN 142:114055 AN 2005:14374 CAPLUS

Step 2

6-(4-amino-2-methylphenyl)-4-(3-methyl-1H-indazol-5-yl)pyrimidin-2(1H)-one

To a solution of (E)-1-(4-amino-2-methylphenyl)-3-(3-methyl-1H-indazol-5-yl)prop-2-en-1-one (0.480 g, 1.64 mmol) in EtOH (5 mL) were added urea (0.900 g, 15 mmol) and 4N HCl/dioxane (5 mL, 20 mmol). The reaction mixture was heated to 110° C. for 17 hours, cooled down and concentrated in vacuo. The product was purified by SiO$_2$ flash chromatography (ethyl acetate to 60:40 ethyl acetate/methanol) and preparative HPLC (reverse-phase, acetonitrile/water with 0.01% ammonium acetate), followed by concentration in vacuo and lyophilization to afford the title compound as an acetate salt (58 mg, 11%). $^1$H NMR (400 MHz, $d_6$-DMSO): δ 8.6 (s, 1H), 8.15 (d, 1H), 7.54 (d, 1H), 7.20 (d, 1H), 7.01 (s, 1H), 6.49 (m, 2H), 5.56 (s, 2H), 2.54 (s, 3H), 2.3 (s, 3H), 1.89 (s, 1H); MS (EI) for $C_{19}H_{17}N_5O$: 332.3 (MH$^±$).

Step 3 tert-butyl 4-((3-methyl-4-(6-(3-methyl-1H-indazol-5-yl)-2-oxo-2,3-dihydropyrimidin-4-yl)phenylamino)methyl)piperidine-1-carboxylate To a solution of 6-(4-amino-2-methylphenyl)-4-(3-methyl-1H-indazol-5-yl)pyrimidin-2(1H)-one (25 mg, 0.06 mmol) in 6 mL dichloroethane were added tert-butyl 4-formylpiperidine-1-carboxylate (76.6 g, 0.36 mmol), NaBH(OAc)$_3$ (76 mg, 0.36 mmol), and 500 µL acetic acid. The reaction mixture was stirred at room temperature for 2 hours and diluted with saturated aqueous NaHCO$_3$ (15 mL) and then extracted with ethyl acetate (3×50 mL). The combined organic phases were washed with brine, dried over Na$_2$SO$_4$ and concentrated in vacuo to afford tert-butyl 4-((3-methyl-4-(6-(3-methyl-1H-indazol-5-yl)-2-oxo-2,3-dihydropyrimidin-4-yl)phenylamino)methyl)piperidine-1-carboxylate, which was submitted to the next step without further purification.

Step 4

4-(3-methyl-1H-indazol-5-yl)-6-{2-methyl-4-[(piperidin-4-ylmethyl)amino]phenyl}pyrimidin-2(1H)-one To a solution of the crude reaction mixture in methanol (2 mL) was added 4N HCl/dioxane (2 mL). The reaction mixture was stirred for 12 hours, concentrated in vacuo and purified by preparative HPLC (reverse-phase, acetonitrile/water with 0.01% ammonium acetate), followed by concentration in vacuo and lyophilization to afford the title compound 4-(3-methyl-1H-indazol-5-yl)-6-{2-methyl-4-[(piperidin-4-ylmethyl)amino]phenyl}pyrimidin-2(1H)-one as an acetate salt (12.6 mg, 49%). $^1$H NMR (400 MHz, $d_6$-DMSO): δ 8.6 (s, 1H), 8.14 (d, 1H), 7.53 (d, 1H), 7.24 (m, 1H), 7.03 (s, 1H), 6.51 (m, 2H), 6.17 (m, 1H), 2.95 (m, 4H), 2.55 (s, 3H), 2.52-2.50 (m, 2H, overlapped), 2.45 (m, 1H), 2.34 (s, 3H), 1.88 (2, 3H), 1.69 (m, 2H), 1.08 (m, 2H); MS (EI) for $C_{25}H_{28}N_6O$: 429.4 (MH$^+$).

Example 37

6-{4-[(2-aminoethyl)amino]-2-methylphenyl}-4-(3-methyl-1H-indazol-5-yl)pyrimidin-2(1H)-one 6-{4-[(2-aminoethyl)amino]-2-methylphenyl}-4-(3-methyl-1H-indazol-5-yl)pyrimidin-2(1H)-one was synthesized in a manner similar to Example 36, in which commerically available tert-butyl 4-formylpiperidine-1-carboxylate was substituted for tert-butyl 2-oxoethylcarbamate. Purification by preparative HPLC (reverse-phase, acetonitrile/water with 0.01% ammonium acetate), followed by concentration in vacuo and lyophilization afforded the title compound as an acetate salt (4 mg, 13%). $^1$H NMR (400 MHz, $d_6$-DMSO): δ 8.60 (s, 1H), 8.14 (d, 1H), 7.53 (d, 1H), 7.26 (d, 1H), 7.03 (s, 1H), 6.52 (m, 2H), 6.16 (m, 1H), 3.09 (m, 2H), 2.73 (m, 2H), 2.56 (s, 3H), 2.35 (2, 3H), 1.87 (s, 3H); MS (EI) for $C_{21}H_{22}N_6O$: 375.4 (MH$^+$).

Example 38

4-(1H-indazol-5-yl)-6-{2-methyl-4-[(piperidin-4-ylmethyl)amino]phenyl}pyrimidin-2(1H)-one 4-(1H-indazol-5-yl)-6-{2-methyl-4-[(piperidin-4-ylmethyl)amino]phenyl}pyrimidin-2(1H)-one was synthesized in a manner similar to Example 36, in which commerically available 1H-indazole-5-carbaldehyde was substituted for 3-methyl-1H-indazole-5-carbaldehyde. $^1$H NMR (400 MHz, $d_6$-DMSO): δ 8.63 (s, 1H), 8.20 (s, 1H), 8.15 (d, 1H), 7.63 (d, 1H), 7.25 (d, 1H), 6.96 (s, 1H), 6.50 (m, 2H), 6.19 (m, 1H), 2.93 (m, 4H), 2.5 (m, 2H, overlapped), 2.35 (s, 3H), 2.32 (m, 1H, overlapped), 1.86 (s, 3H), 1.71 (m, 2H), 1.06 (m, 2H); MS (EI) for $C_{24}H_{26}N_6O$: 415.1 (MH$^+$).

Example 39

6-{4-[(2-aminoethyl)amino]-2-methylphenyl}-4-(1H-indazol-5-yl)pyrimidin-2(1H)-one 6-{4-[(2-aminoethyl)amino]-2-methylphenyl}-4-(1H-indazol-5-yl)pyrimidin-2(1H)-one was synthesized in a manner similar to Example 38, in which commerically available tert-butyl 4-formylpiperidine-1-carboxylate was substituted for tert-butyl 2-oxoethylcarbamate. $^1$H NMR (400 MHz, $d_6$-DMSO): δ 8.63 (s, 1H), 8.21 (s, 1H), 8.15 (d, 1H), 7.63 (d, 1H), 7.27 (s, 1H), 6.97 (s, 1H), 6.53 (m, 2H), 6.15 (m, 1H), 3.10 (m, 2H), 2.74 (m, 2H), 2.36 (s, 3H), 1.9 (s, 2H); MS (EI) for $C_{20}H_{20}N_6O$: 361.3 (MH$^+$)

Example 40

See Scheme 6

4-(3-methyl-1H-indazol-5-yl)-6-(2-{[2-(methyloxy)ethyl]oxy}phenyl)pyrimidin-2(1H)-one Example 41

See Scheme 6

6-{2-[(2-hydroxyethyl)oxy]phenyl}-4-(3-methyl-1H-indazol-5-yl)pyrimidin-2(1H)-one 4-(3-methyl-1H-indazol-5-yl)-6-(2-{[2-(methyloxy)ethyl]oxy}phenyl)pyrimidin-2(1H)-one and 6-{2-[(2-hydroxyethyl)oxy]phenyl}-4-(3-methyl-1H-indazol-5-yl)pyrimidin-2(1H)-one were synthesised as outlined in Scheme 6.

Scheme 6

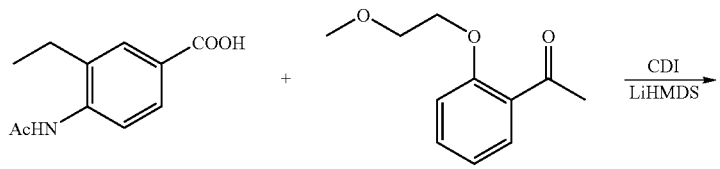

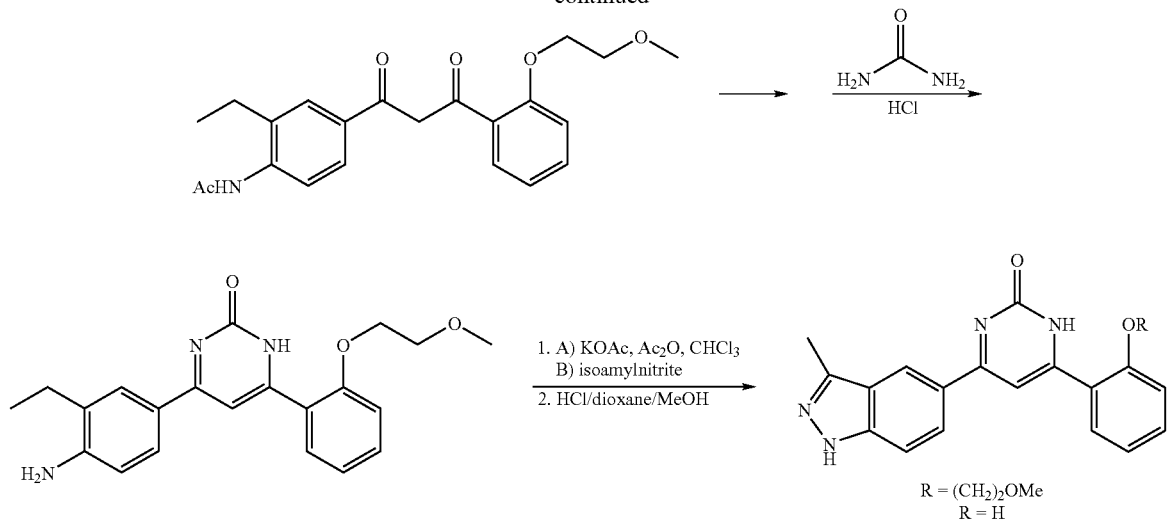

Step 1

1-(4-acetamido-3-ethylphenyl)-3-(2-(2-methoxyethoxy)phenyl)propane-1,3-dione

To a suspension of commercially available 4-acetamido-3-ethylbenzoic acid (Rarechem) (10 g, 48 mmol) in anhydrous THF (100 mL) was added 1,1-carbonyldiimidazole (8.5 g, 53 mmol) and the resulting mixture was stirred for 1 hour at room temperature.

A separated flask was charged with 1-(2-(2-methoxyethoxy)phenyl)ethanone (11.2 g, 57 mmol). (1-(2-(2-Methoxyethoxy)phenyl)ethanone was prepared by a procedure analogous to Example 1, in which commercially 1-bromo-2-methoxyethane was substituted for 1-bromo-2-methyl propane). The 1-bromo-2-methoxyethane was added to anhydrous THF (50 mL) and cooled to −78° C. To this solution was added commercially available lithium hexamethyl-silylamide (1M in hexanes, 172 mL, 172 mmol, Aldrich) over a 3 hour period at −78° C. The mixture was stirred for an additional 2 hours at −78° C. To the resulting mixture were added dropwise a solution of CDI and 4-acetamido-3-ethylbenzoic acid (above) at −78° C. The resulting mixture was stirred at −78° C. for an additional 30 min and subsequently allowed to warm up to room temperature over 12 h. The reaction was quenched with 1 N HCl and extracted with EtOAc and water. The organic layer was separated, dried over sodium sulfate, filtered, and concentrated under reduced pressure. The residue was purified by chromatography to give 1-(4-acetamido-3-ethylphenyl)-3-(2-(2-methoxyethoxy)phenyl)propane-1,3-dione as a white solid (11 g, 60%).

Step 2

4-(2-ethylanilin-4-yl)-6-[2-(2-methoxyethoxy)phenyl]pyrimidin-2(1H)-one

A flask was charged with 1-(4-acetamido-3-ethylphenyl)-3-(2-(2-methoxyethoxy)phenyl)propane-1,3-dione (4.0 g, 10.4 mmol), urea (3.0 g, 50 mmol) and 4 N HCl in dioxane (80 mL). The mixture was heated to 110° C. overnight. The reaction was cooled down, concentrated, neutralized with sodium bicarbonate, and extracted with ethyl acetate. The organic layer was dried over sodium sulfate, filtered, and concentrated under reduced pressure. The residue was purified by column chromatography to result in 4-(2-ethylanilin-4-yl)-6-[2-(2-methoxyethoxy)phenyl]pyrimidin-2(1H)-one as a white solid.

Step 3

4-(3-methyl-1-acetyl-1H-indazol-5-yl)-6-(2-{[2-(methyloxy)ethyl]oxy}phenyl)pyrimidin-2(1H)-one A flask was charged with 4-(2-ethylanilin-4-yl)-6-[2-(2-methoxyethoxy)phenyl]-pyrimidin-2(1H)-one (5.5 g, 15 mmol), chloroform (150 mL), acetic anhydride (6.2 mL, 66.7 mmol) and potassium acetate (2.54 g, 30 mmol). The mixture was heated at 40° C. for 2 hours followed by the addition of isoamyl nitrite (5.24 mL, 39 mmol). The resulting mixture was heated to 60° C. overnight, concentrated under reduced pressure, neutralized with sodium bicarbonate, and extracted with EtOAc. The organic layer was concentrated under reduced pressure, and purified by column chromatography to give 4-(3-methyl-1-acetyl-1H-indazol-5-yl)-6-(2-{[2-(methyloxy)ethyl]oxy}phenyl)pyrimidin-2(1H)-one (4.0 g, 65%).

Step 4

4-(3-methyl-1H-indazol-5-yl)-6-(2-{[2-(methyloxy)ethyl]oxy}phenyl)pyrimidin-2(1H)-one 6-{2-[(2-hydroxyethyl)oxy]phenyl}-4-(3-methyl-1H-indazol-5-yl)pyrimidin-2(1H)-one A flask was charged with 4-(3-methyl-1-acetyl-1H-indazol-5-yl)-6-(2-{[2-(methyloxy)ethyl]oxy}phenyl)pyrimidin-2(1H)-one (2.50 g, 6.2 mmol), MeOH (60 mL) and 10 ml of 4 N HCl in dixoane (Aldrich). The mixture was heated at 60° C. overnight. The reaction was concentrated, and the residue was submitted to preparative HPLC (reverse-phase, acetonitrile/water with 0.01% ammonium acetate) to result in 4-(3-methyl-1H-indazol-5-yl)-6-(2-{[2-(methyloxy)ethyl]oxy}phenyl)pyrimidin-2(1H)-one (1.32 g). $^1$H NMR (400 MHz, d6-DMSO): δ 12.90 (s, br, 1H), 11.75 (s, br, 1H), 8.60 (s, 1H), 8.15 (d, 1H), 7.75 (d, 1H), 7.60-7.45 (m, 3H), 7.25-7.10 (m, 2H), 4.20 (t, 2H), 3.75 (t, 2H), 3.40 (s, 3H), 2.60 (s, 3H). MS (EI) for $C_{21}H_{20}N_4O_3$: 377 (MH$^+$); and 6-{2-[(2- hydroxyethyl)oxy]phenyl}-4-(3-methyl-1H-indazol-5-yl)pyrimidin-2(1H)-one (250 mg) $^1$H NMR (400 MHz, d6-DMSO): δ 8.88 (s, 1H), 8.09 (d, 1H), 7.80-7.45 (m, 4H), 7.35-7.05 (m, 2H), 4.23 (t, 2H), 3.80 (t, 2H), 2.40 (s, 3H). MS (EI) for $C_{20}H_{18}N_4O_3$: 363 (MH$^+$).

Example 42

4-(3-methyl-1H-indazol-5-yl)-6-{2-[(2-methylpropyl)oxy]phenyl}pyridin-2(1H)-one

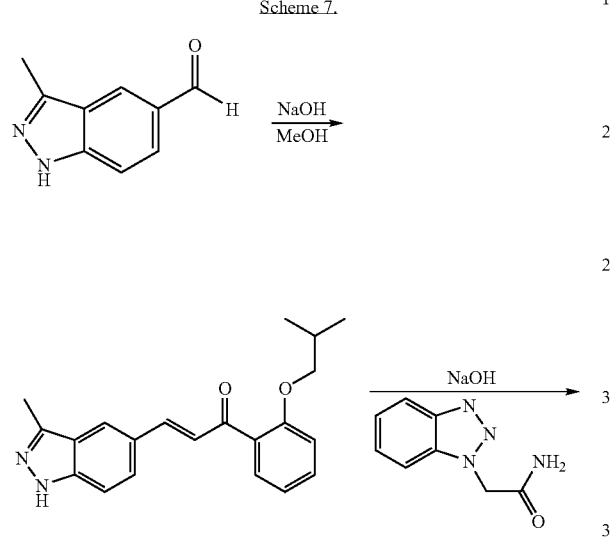

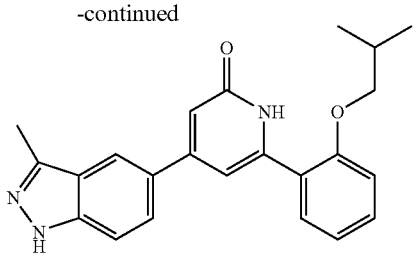

To a solution of NaOH (0.2 g, 5 mmol) in 3 mL ethanol were added commercially available 1-(2-isobutoxyphenyl)ethanone (100 mg, 0.52 mmol) and commercially available 3-methyl-1H-indazole-5-carbaldehyde (200 mg, 1.25 mmol). The reaction mixture was stirred at room temperature for 24 h, concentrated under reduced pressure and the product was purified by SiO$_2$ flash chromatography (60:40 hexanes/ethyl acetate) to afford (E)-1-(2-isobutoxyphenyl)-3-(3-methyl-1H-indazol-5-yl)prop-2-en-1-one (50 mg, 28.6%). $C_{21}H_{22}N_2O_2$: 335 (MH$^+$).

To a mixture of (E)-1-(2-isobutoxyphenyl)-3-(3-methyl-1H-indazol-5-yl)prop-2-en-1-one (50 mg, 0.15 mmol), 2-(1H-benzo[d][1,2,3]triazol-1-yl)acetamide (Aldrich) (50 mg, 2.84 mmol), and 20 mg of NaOH in 10 mL of EtOH was heated to 90° C. for 4 h. The reaction mixture was concentrated down and purified by preparative HPLC (reverse-phase, acetonitrile/water with 0.01% ammonium acetate) to afford 4-(3-methyl-1H-indazol-5-yl)-6-{2-[(2-methylpropyl)oxy]phenyl}pyridin-2(1H)-one (12 mg, 21.4%). $^1$H NMR (400 MHz, d$_6$-DMSO): δ 12.78 (s, 1H), 8.15 (s, 1H), 7.71 (d, 1H), 7.53 (m, 2H), 7.45 (t, 1H), 7.15 (d, 1H), 7.07 (t, 1H), 6.77 (br s, 1H), 6.61 (s, 1H), 3.84 (d, 2H), 2.02 (m, 1H), 0.95 (d, 6H); MS (EI) for $C_{23}H_{23}N_3O_2$: 374 (MH$^+$).

Example 43

4-(3-amino-1H-indazol-5-yl)-6-[2-(propyloxy)phenyl]pyridin-2(1H)-one

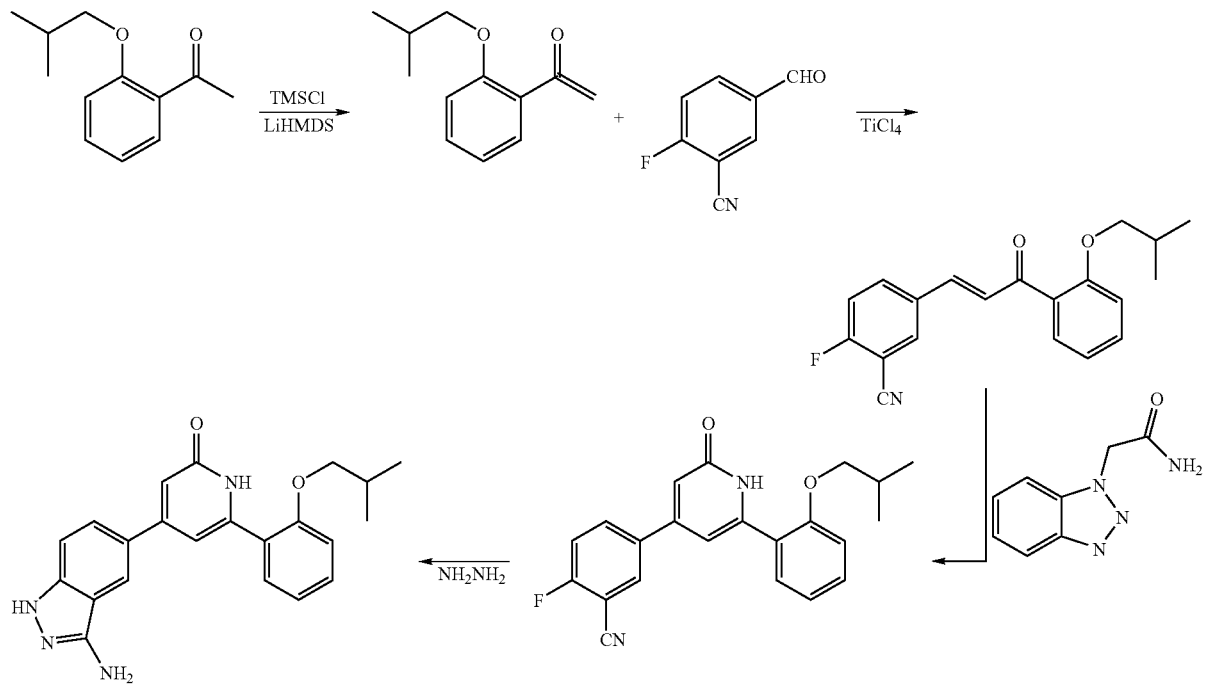

Step 1

(1-(2-isobutoxyphenyl)vinyloxy)trimethylsilane

A solution of commercially available 1-(2-isobutoxyphenyl)ethanone (10.0 g, 56.5 mmol) in THF (30 mL) was added dropwise to a stirred solution of lithium hexamethylsilylamide (1M in hexanes, 62 mL) in THF (200 mL) over a period of 30 min at 0° C. The resulting solution was stirred for an additional 15 min, and a solution of chlorotrimethylsilane (7.1 mL) in THF (8 mL) was added. The reaction mixture was stirred for 4 hours at room temperature. The mixture was concentrated. To the residue was added dichloromethane (60 mL), the mixture was filtered. The filtrate was concentrated to give (1-(2-isobutoxyphenyl)vinyloxy)trimethylsilane, that was submitted to the next step without further purification.

Step 2

(E)-2-fluoro-5-(3-(2-isobutoxyphenyl)-3-oxoprop-1-enyl)benzonitrile

To a solution of commercially available 2-fluoro-5-formylbenzonitrile (2.49 g, 10 mmol) in dichloromethane (40 mL) was added (1-(2-isobutoxyphenyl)vinyloxy)trimethylsilane (1.49 g, 10 mmol), followed by titanium tetrachloride (1.5 eq). The reaction was stirred at room temperature for 5 hours and then heated at 40° C. for overnight. The reaction was cooled and quenched with 1 N HCl (40 mL). The mixture was stirred for 2 hours and diluted with dichloromethane/water. The organic layer was separated, dried over sodium sulfate and concentrated under reduced pressure. The residue was purified by the chromatography to give (E)-2-fluoro-5-(3-(2-isobutoxyphenyl)-3-oxoprop-1-enyl)benzonitrile as a white solid (1.60 g, 50% yield). $^1$H NMR (400 MHz, CDCl$_3$): δ 7.88-7.75 (m, 2H), 7.70 (d, 1H), 7.57 (d, 1H), 7.54-7.45 (m, 2H), 7.28 (d, 1H), 7.08-6.98 (m, 2H), 3.84 (d, 2H), 2.17-2.03 (m, 1H), 1.00 (d, 6H). MS (EI) for C$_{20}$H$_{18}$FNO$_2$: 268 (MH$^+$).

Step 3

2-fluoro-5-(6-{2-[(2-methylpropyl)oxy]phenyl}-2-oxo-1,2-dihydropyridin-4-yl)benzonitrile A mixture of (E)-2-fluoro-5-(3-(2-isobutoxyphenyl)-3-oxoprop-1-enyl)benzonitrile (324 mg, 1 mmol), commercially available 2-(1H-benzo[d][1,2,3]triazol-1-yl)acetamide (176 mg, 1 mmol), and NaOH (80 mg) in 5 mL of EtOH was heated to 50° C. for 5 h. The reaction mixture was acidified with conc. HCl, concentrated and purified by preparative HPLC (reverse-phase, acetonitrile/water with 0.01% ammonium acetate) to afford 2-fluoro-5-(6-{2-[(2-methylpropyl)oxy]phenyl}-2-oxo-1,2-dihydropyridin-4-yl)benzonitrile (70 mg, 39%). $^1$H NMR (400 MHz, CDCl$_3$): δ 7.90-7.80 (m, 2H), 7.78 (d, 1H), 7.46-7.33 (m, 2H), 7.13-7.03 (m, 2H), 6.62 (d, 2H), 3.85 (d, 2H), 2.21-2.14 (m, 1H), 1.06 (d, 6H). MS (EI) for C$_{22}$H$_{19}$FN$_2$O$_2$: 363 (MH$^+$).

Step 4

4-(3-amino-1H-indazol-5-yl)-6-[2-(propyloxy)phenyl]pyridin-2(1H)-one

A mixture of 2-fluoro-5-(6-{2-[(2-methylpropyl)oxy]phenyl}-2-oxo-1,2-dihydropyridin-4-yl)benzonitrile (50 mg), and hydrazine hydrate (2 mL) in ethanol (10 mL) was heated to 100° C. for 3 h. The reaction mixture was concentrated and the product was purified by preparative HPLC (reverse-phase, acetonitrile/water with 0.01% ammonium acetate) to afford 4-(3-amino-1H-indazol-5-yl)-6-[2-(propyloxy)phenyl]pyridin-2(1H)-one (20 mg). $^1$H NMR (400 MHz, d4-CD3OD): δ 8.18 (s, 1H), 7.72 (d, 1H), 7.57 (d, 1H), 7.46 (t, 1H), 7.39 (d, 1H), 7.16-7.08 (m, 2H), 6.92 (d, 1H), 6.76 (s, 1H), 3.88 (d, 2H), 2.12-2.05 (m, 1H), 1.00 (d, 6H). MS (EI) for C$_{22}$H$_{22}$N$_4$O$_2$: 375 (MH$^+$).

Example 44

4-(3-amino-1H-indazol-5-yl)-6-[2-(propyloxy)phenyl]pyridin-2(1H)-one 4-(3-amino-1H-indazol-5-yl)-6-[2-(propyloxy)phenyl]pyridin-2(1H)-one was prepared by a procedure analogous to Example 43, in which commercially available 1-(2-propyloxyphenyl)ethanone was substituted for 1-(2-isobutoxyphenyl)ethanone. $^1$H NMR (400 MHz, d6-DMSO): δ 8.62 (s, 2H), 8.00 (s, 1H), 7.60 (s, 1H), 7.48 (t, 1H), 7.27 (d, 1H), 7.20-7.05 (m, 3H), 5.60 (s, 2H), 4.00 (t, 2H), 1.75-1.63 (m, 2H), 0.90 (t, 3H). MS (EI) for C$_{20}$H$_{19}$N$_5$O$_2$: 362 (MH$^+$).

Example 45

4-(4-hydroxy-3-methylphenyl)-6-(4-methyl-1,3-thiazol-5-yl)pyrimidin-2(1H)-one

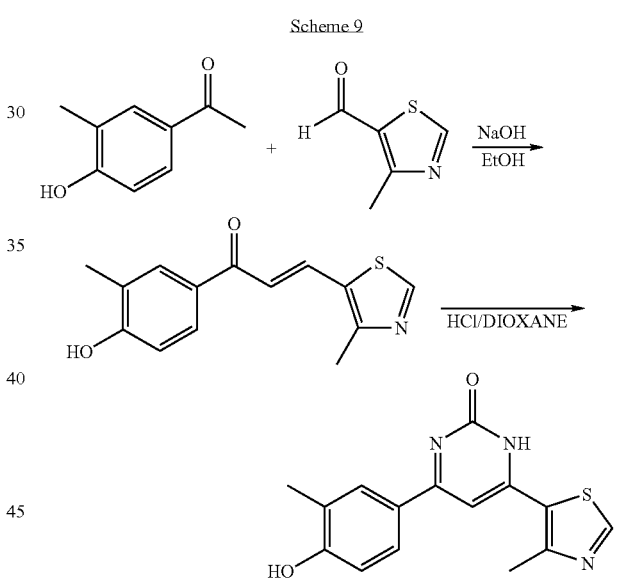

Scheme 9

Step 1

(E)-1-(4-hydroxy-3-methylphenyl)-3-(4-methylthiazol-5-yl)prop-2-en-1-one

Commerically available 4-methylthiazole-5-carbaldehyde (0.59 g, 4.6 mmol) and 4'-hydroxy-3'-methylacetophenone (0.7 g, 4.6 mmol) were dissolved in 10 mL of absolute EtOH. The solution was cooled with an ice-water bath, and NaOH (0.36 g, 9.0 mmol) was added. The reaction mixture was stirred for 18 h at room temperature. Upon completion, the reaction mixture was acidified to pH=4-5 with 1 M HCl. The resulting orange precipitate was filtered out, washed with an additional 5 mL of water, and dried under air. The resulting ((E)-1-(4-hydroxy-3-methylphenyl)-3-(4-methylthiazol-5-yl)prop-2-en-1-one (1.03 g, 87%) was submitted to the next step without further purification. MS (EI) for C$_{14}$H$_{13}$NO$_2$S: 260 (MH$^+$).

Step 2

4-(4-hydroxy-3-methylphenyl)-6-(4-methyl-1,3-thiazol-5-yl)pyrimidin-2(1H)-one (((E)-1-(4-hydroxy-3-methylphenyl)-3-(4-methylthiazol-5-yl)prop-2-en-1-one (200 mg, 0.77 mmol) and urea (0.23 g, 3.8 mmol) were suspended in 5 mL of 4N HCl solution in dioxane (Aldrich), and the reaction mixture was heated in a sealed vessel to 120° C. for 20 h. After cooling to room temperature, the resulting mixture was concentrated in vacuo to remove dioxane. The residue was dissolved in 5 mL of methanol, and the product was purified by preparative HPLC (reverse-phase, acetonitrile/water with 0.1% formic acid) to yield 7.7 mg of 4-(4-hydroxy-3-methylphenyl)-6-(4-methyl-1,3-thiazol-5-yl)pyrimidin-2(1H)-one. $^1$H NMR (400 MHz, d6-DMSO): δ 9.11 (s, 1H), 7.81 (d, 1H), 7.72 (dd, 1H), 7.07 (s, 1H), 6.90 (d, 1H), 2.73 (s, 3H), 2.17 (s, 3H). MS (EI) for $C_{15}H_{13}N_3O_2S$: 300.4 (MH$^+$).

Example 45

6-(1-benzofuran-2-yl)-4-(4-hydroxy-3-methylphenyl)pyrimidin-2(1H)-one 6-(1-benzofuran-2-yl)-4-(4-hydroxy-3-methylphenyl)pyrimidin-2(1H)-one was prepared by a procedure analogous to Example 45, in which commercially available benzofuran-2-carbaldehyde was substituted for 4-methylthiazole-5-carbaldehyde. $^1$H NMR (400 MHz, d6-DMSO): 7.91 (m, 2H), 7.82 (m, 2H), 7.72 (dd, 1H), 7.50-7.46 (m, 1H), 7.41 (s, 1H), 7.37-7.34 (m, 1H), 6.92 (d, 1H), 2.15 (s, 3H). MS (EI) for $C_{19}H_{14}N_2O_3$: 319.4 (MH$^+$).

Example 46

4-(4-hydroxy-3-methylphenyl)-6-(1-methyl-1H-imidazol-2-yl)pyrimidin-2(1H)-one 4-(4-hydroxy-3-methylphenyl)-6-(1-methyl-1H-imidazol-2-yl)pyrimidin-2(1H)-one was prepared by a procedure analogous to Example 45, in which commercially available 1-methyl-1H-imidazole-2-carbaldehyde was substituted for 4-methylthiazole-5-carbaldehyde. $^1$H NMR (400 MHz, d6-DMSO): δ 10.90 (s, 1H), 8.65 (s, 1H), 8.24 (s, 1H), 7.95 (d, 1H), 7.87 (dd, 1H), 7.49 (s, 1H), 7.02 (d, 1H), 3.84 (s, 3H), 2.21 (s, 3H). MS (EI) for $C_{15}H_{14}N_4O_2$: 283.3 (MH$^+$).

Example 47

6-(4,5-dimethylfuran-2-yl)-4-(4-hydroxy-3-methylphenyl)pyrimidin-2(1H)-one 6-(4,5-dimethylfuran-2-yl)-4-(4-hydroxy-3-methylphenyl)pyrimidin-2(1H)-one was prepared by a procedure analogous to Example 45, in which commercially available 4,5-dimethylfuran-2-carbaldehyde was substituted for 4-methylthiazole-5-carbaldehyde. $^1$H NMR (400 MHz, d6-DMSO): δ 11.64 (s, 1H), 10.17 (s, 1H), 7.83 (s, 1H), 7.74 (s, 1H), 7.33 (s, 1H), 7.03 (s, 1H), 6.89 (d, 1H), 2.32 (s, 3H), 2.19 (s, 3H), 1.99 (s, 3H). MS (EI) for $C_{17}H_{16}N_2O_3$: 297 (MH$^+$).

Example 48

6-furan-3-yl-4-(4-hydroxy-3-methylphenyl)pyrimidin-2(1H)-one 6-furan-3-yl-4-(4-hydroxy-3-methylphenyl)pyrimidin-2(1H)-one was prepared by a procedure analogous to Example 45, in which commercially available furan-3-carbaldehyde was substituted for 4-methylthiazole-5-carbaldehyde. $^1$H NMR (400 MHz, d6-DMSO): δ 8.65 (s, 1H), 7.94-7.80 (m, 3H), 7.24 (s, 2H), 6.89 (d, 1H), 2.20 (s, 3H). MS (EI) for $C_{15}H_{12}N_2O_3$: 269 (MH$^+$).

Example 49

6-(4-hydroxy-3-methylphenyl)-4-pyridin-4-ylpyrimidin-2(1H)-one 6-(4-hydroxy-3-methylphenyl)-4-pyridin-4-ylpyrimidin-2(1H)-one was prepared by a procedure analogous to Example 45, in which commercially available isonicotinaldehyde was substituted for 4-methylthiazole-5-carbaldehyde. $^1$H NMR (400 MHz, d6-DMSO): δ 8.77 (d, 2H), 8.1 (d, 2H), 8.00 (s, 1H), 7.89 (s, 1H), 6.91 (d, 1H), 2.21 (s, 3H). MS (EI) for $C_{16}H_{13}N_3O_2$: 280 (MH$^4$).

Example 50

5-(6-{2-[(3-methylbutyl)oxy]phenyl}-2-oxo-1,2-dihydropyrimidin-4-yl)-1,3-dihydro-2H-benzimidazol-2-one Scheme 10

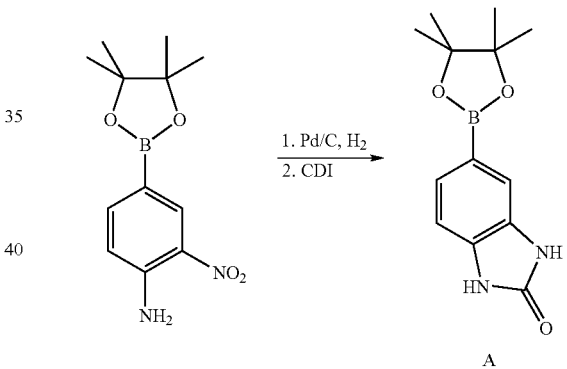

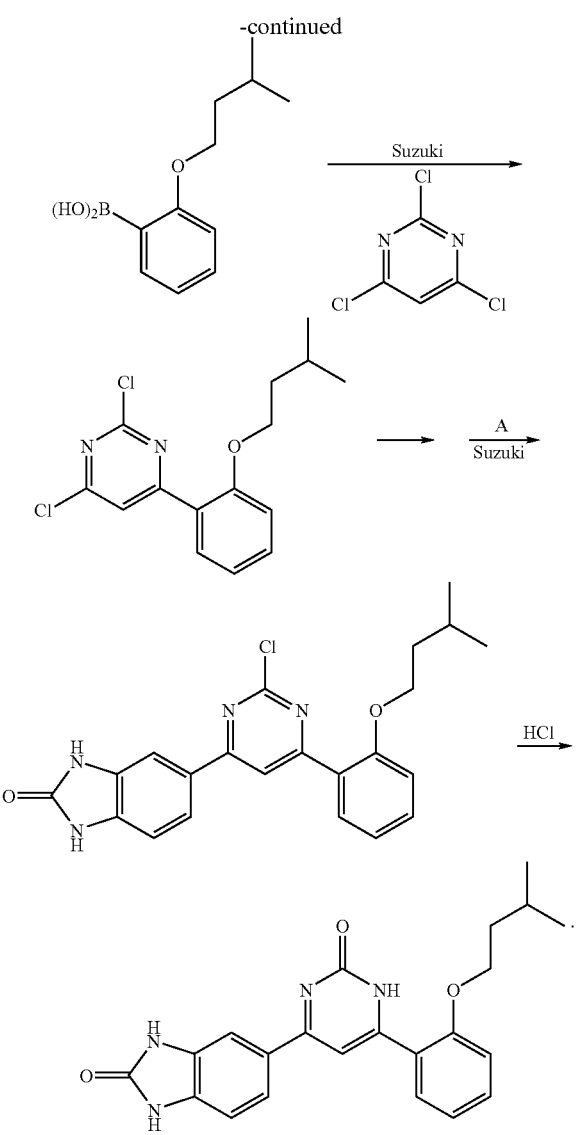

Step 1. (A)

5-(4,4,5,5-tetramethyl-1,3,2-dioxaborolan-2-yl)-1H-benzo[d]imidazol-2(3H)-one To a solution of commercially available 2-nitro-4-(4,4,5,5-tetramethyl-1,3,2-dioxaborolan-2-yl)aniline (2.0 g, 7.5 mmol) in MeOH (50 mL) was added 10% wet Pd—C (50% water in weight, 200 mg). The reaction mixture was flushed with $H_2$ and hydrogenated at 3.3 bar for 2 h. Upon completion the suspension was filtered through Celite to remove the catalyst. The filtrate was concentrated under reduced pressure to give 4-(4,4,5,5-tetramethyl-1,3,2-dioxaborolan-2-yl)benzene-1,2-diamine, that was submitted to the next step without further purification.

To a solution of 4-(4,4,5,5-tetramethyl-1,3,2-dioxaborolan-2-yl)benzene-1,2-diamine (1.20 g, 5.1 mmol) in anhydrous THF (20 mL) was added 1,1'-carbonyldiimidazole (910 mg, 5.6 mmol). The reaction mixture was stirred at room temperature for 2 hours. The resulting solution was acidified with 1 N HCl (10 mL) and extracted twice with 50 mL portions of $Et_2O$. The combined organic layers were washed with saturated brine, dried over $Na_2SO_4$, filtered, and concentrated under reduced pressure to give 1.0 g (79%) of 5-(4,4,5,5-tetramethyl-1,3,2-dioxaborolan-2-yl)-1H-benzo[d]imidazol-2(3H)-one. $^1$H NMR (400 MHz, $CDCl_3$): δ 7.46 (dd, 1H), 7.40 (s, 1H), 7.35 (dd, 1H), 1.35 (s, 12H). MS (EI) for $C_{13}H_{17}BN_2O_3$: 261 (MH$^+$).

Step 2

1-bromo-2-(isopentyloxy)benzene

A round-bottomed flask was charged with commercially available 2-bromophenol (43 g, 0.25 mol), 1-bromo-3-methylbutane (41 mL, 0.33 mol), potassium carbonate (0.38 mol), and 200 mL of $CH_3CN$. The resulting slurry was heated to 80° C. for 18 h. Upon completion, the mixture was cooled down to the room temperature, filtered, and concentrated down under reduced pressure. Vacuum distillation of the residue resulted in 1-bromo-2-(isopentyloxy)benzene (56 g, 93%, b.p. 82° C. at 10 mm Hg) as a colorless liquid. $^1$H NMR (400 MHz, $CDCl_3$): δ 7.55 (d, 1H), 7.25 (t, 1H), 6.90 (d, 1H), 6.80 (t, 1H), 4.05 (t, 2H), 1.97-1.85 (m, 1H), 1.78-1.70 (m, 2H), 0.98 (d, 6H).

Step 3

2-(isopentyloxy)phenylboronic acid

To a solution of 1-bromo-2-(isopentyloxy)benzene (9.68 g, 40 mmol) in THF (160 mL) under $N_2$ atmosphere at −78° C. was added dropwise n-butyl lithium (1.6 M in hexanes, 26.3 mL, 42 mmol, Aldrich) over 30 min period. The reaction mixture was stirred for an additional 1 hour at −78° C., followed by the drop wise addition of triethyl borate (5.86 mL, 51 mmol). The cooling bath was removed, and the reaction was allowed to warm up to the room temperature then stirred for an additional 18 h at room temperature. The reaction mixture was acidified with 2 N HCl (20 mL) and water (50 mL). The resulting slurry was extracted with 5 of 80 mL portions of $Et_2O$. The combined organic layers were dried over sodium sulfate, filtered, and concentrated under reduced pressure to give 6.30 g (77%) of 2-(isopentyloxy)-phenylboronic acid. $^1$H NMR (400 MHz, $CDCl_3$): 7.83 (d, 1H), 7.43 (dd, 1H), 7.03 (t, 1H), 6.93 (t, 1H), 6.05 (s, 1H), 4.10 (t, 2H), 1.85-1.75 (m, 3H), 1.02 (s, 6H).

Step 4

2,4-dichloro-6-(2-(isopentyloxy)phenyl)pyrimidine

To a solution of 2,4,6-trichloropyrimidine (7.32 g, 40 mmol) in 40 mL of THF was added 2-(isopentyloxy)phenylboronic acid (4.1 g, 20 mmol), Pd(OAc)$_2$ (0.4 mmol), PPh$_3$ (0.8 mmol), and $Na_2CO_3$ solution (40 mL, 1M). The reaction was heated to 60° C. for 3 hours with stirring. The resulting mixture was cooled down to room temperature then partitioned between EtOAc and water. Layers were separated, and the organic layer was washed with brine, dried over sodium sulfate, filtered, and concentrated under reduced pressure. The residue was purified by column chromatography to result in 4.3 g (70%) of 2,4-dichloro-6-(2-(isopentyloxy)phenyl)pyrimidine as a white solid. $^1$H NMR (400 MHz, $CDCl_3$): δ 8.18-8.14 (m, 2H), 7.45 (dd, 1H), 7.09 (t, 1H), 7.01 (t, 1H), 4.10 (t, 2H), 1.90-1.75 (m, 3H), 1.02 (s, 6H).

Step 5

5-(6-{2-[(3-methylbutyl)oxy]phenyl}-2-oxo-1,2-dihydropyrimidin-4-yl)-1,3-dihydro-2H-benzimidazol-2-one A round bottom flask was charged with 2,4-dichloro-6-(2-(isopentyloxy)phenyl)pyrimidine (100 mg, 0.32 mmol), 5-(4, 4,5,5-tetramethyl-1,3,2-dioxaborolan-2-yl)-1H-benzo[d]imidazol-2(3H)-one (91 mg, 0.35 mmol), Pd(dppf)Cl$_2$ (3 mol %), 1 M NaHCO$_3$ (0.3 mL), and THF (5 mL). The reaction mixture was heated to 70° C. for 2 hours. The reaction mixture was allowed to cool down to the room temperature, and 4 mL of conc. HCl was slowly added. The resulting slurry was heated to 100° C. for an additional 5 hours. The mixture was cooled down to room temperature, filtered, and concentrated under reduced pressure. The product was purified by preparative HPLC to result in 5-(6-{2-[(3-methylbutyl)oxy]phenyl}-2-oxo-1,2-dihydropyrimidin-4-yl)-1,3-dihydro-2H-benzimidazol-2-one. $^1$H NMR (400 MHz, d6-DMSO): δ 10.95 (s, 2H), 7.81-7.75 (m, 3H), 7.53 (t, 1H), 7.20 (d, 1H), 7.14-7.05 (m, 2H), 4.08 (t, 2H), 1.80-1.60 (m, 3H), 0.85 (s, 6H). MS (EI) for $C_{22}H_{22}N_4O_3$: 391 (MH$^+$).

Example 51

6-(1H-indazol-6-yl)-4-{2-[(3-methylbutyl)oxy]phenyl}pyrimidin-2(1H)-one 6-(1H-indazol-6-yl)-4-{2-[(3-methylbutyl)oxy]phenyl}pyrimidin-2(1H)-one was prepared by a procedure analogous to Example 50, in which commercially available 1H-indazol-6-ylboronic acid was substituted for 5-(4,4,5,5-tetramethyl-1,3,2-dioxaborolan-2-yl)-1H-benzo[d]imidazol-2(3H)-one. $^1$H NMR (400 MHz, d6-DMSO): δ 8.38 (s, 1H), 8.18 (s, 1H), 7.93-7.85 (m, 2H), 7.70 (d, 1H), 7.57 (t, 1H), 7.38 (s, 1H), 7.21 (d, 1H), 7.15 (t, 1H). MS (EI) for $C_{22}H_{22}N_4O_2$: 375 (MH$^+$).

Example 52

5-[6-(2-chlorophenyl)-2-oxo-1,2-dihydropyrimidin-4-yl]-1,3-dihydro-2H-benzimidazol-2-one 5-[6-(2-chlorophenyl)-2-oxo-1,2-dihydropyrimidin-4-yl]-1,3-dihydro-2H-benzimidazol-2-one was prepared by a procedure analogous to Example 50, in which commercially available 2-chlorophenylboronic acid was substituted for 2-(isopentyloxy)-phenylboronic acid. $^1$H NMR (400 MHz, d6-DMSO): δ 11.00 (s, 2H), 7.81-7.75 (m, 2H), 7.62-7.43 (m, 4H), 7.12-7.00 (m, 3H). MS (EI) for $C_{17}H_{11}ClN_4O_3$: 339 (MH$^+$).

Biological Assay:

For a biochemical measurement of CK2 inhibitory activity, compounds of the invention were screened in a luciferase-coupled chemiluminescence assay that detects consumption of ATP by the CK2 enzyme. The assay was performed using two different constructs of the enzyme, CK2 holoenzyme and CK2 alpha subunit. The assay buffer is composed of 20 mM Tris, pH 7.5, 10 mM MgCl$_2$, 0.03% Triton-X-1000, 1 mM DTT and 0.1 mM NaVO$_3$.

For the CK2 alpha subunit assay, the assay is performed as follows: 0.5 μl of test compound is added to a microtiter plate, followed by the addition of 10 μl substrate containing CK2 peptide (RRRDDDSDDD) and ATP and 10 μl of alpha subunit of the CK2 enzyme. The concentration of CK2 peptide is 9 μM, ATP is 2 μM and CK2-alpha subunit is 10 nM.

For the CK2 holoenzyme assay, the assay is performed as follows: 0.5 μl of test compound is added to a microtiter plate, followed by the addition of 10 μl substrate containing casein and ATP and 10 μl of CK2 holoenzyme. The concentration of casein is 2 μM, ATP is 2 μM and CK2 holoenzyme is 6 nM.

For both assays, the mixture is shaken briefly and incubated for 120 min at room temperature. At the end of the incubation, 10 μl of Kinase Glo (luciferase) is added and the signal is detected in a luminescence reader (Victor, Perkin Elmer).

The compounds in Table 1 have been tested for their CK2 inhibitory activity (IC$_{50}$ values), and these compounds have CK2 IC$_{50}$ values of less than 5000 nM. A preferred group of compounds of Table 1 have CK2 IC$_{50}$ values of less than 4000 nm. Another preferred group of compounds of Table 1 have CK2 IC$_{50}$ values of less than 510 nm. Another preferred group of compounds of Table 1 have CK2 IC$_{50}$ values of less than 500 nm. Another preferred group of compounds of Table 1 have CK2 IC$_{50}$ values of less than 200 nm. Another preferred group of compounds of Table 1 have CK2 IC$_{50}$ values of less than 100 nm.

Compounds of the invention may also be active against PIM 1 and/or PIM 2 kinase activity. Accordingly, compounds of the invention can also be useful for treating proliferative disorders associated with PIM 1 and/or PIM 2 kinase activity.

PIM Assay Protocol

PIM kinase activity can be measured by monitoring peptide substrate dependent hydrolysis of ATP via quantitation of remaining ATP with luciferase based chemiluminescence. For compound evaluation, 0.5 ul compound dissolved in DMSO is added to 10 ul of PIM-1, PIM 2 and/or PIM-3 dissolved in assay buffer (20 mM HEPES pH 7.5, 10 mM MgCl2, 0.03% Triton and 1 mM DTT). After preincubation for about 30 minutes at about room temperature, the reaction is initiated by addition of 10 ul of ATP and substrate peptide AKRRRLSA in assay buffer. The reaction mixture is incubated for about 120 min at room temperature, and the reaction progress can be quantitated by addition of 10 ul Kinase-Glo (Promega) and measuring chemiluminescence in a Victor reader (Perkin Elmer). A reaction in which compound is omitted is used to determine maximum reaction progress. Omission of compound and enzyme from the reaction can be used to determine zero reaction progress.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A compound in the form of Formula I,

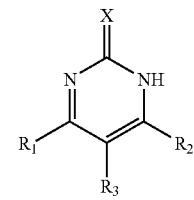

or a pharmaceutically acceptable salt thereof, wherein
X is O or S;
R$_1$ is phenyl substituted with —O—CH$_2$—C(H)(CH$_3$)$_2$;
R$_2$ is benzodioxolyl, benzofuranyl, imidazolyl, 1,2-dihydro-2H-benzimidizol-2-one, 1,3-dihydro-2H-benzimidizol-2-one, thiazolyl, indazolyl, furanyl, or benzisoxazolyl, wherein each of said benzodioxolyl, benzofuranyl, imidazolyl, 1,2-dihydro-2H-benzimidizol-2-one, 1,3-dihydro-2H-benzimidizol-2-one, thiazolyl, indazolyl, furanyl, or benzisoxazolyl is optionally substituted with 1, 2 or 3 groups, which can be the same or different, selected from —N(H)(C$_1$-C$_6$)alkyl-N(H)C(O)—(C$_1$-C$_6$)alkyl-N[(C$_1$-C$_6$)alkyl]$_2$, —N(H)(C$_1$-C$_6$)alkyl-R$_9$, —(C$_1$-C$_6$)alkyl, —N[(C$_1$-C$_6$)alkyl](C$_1$-C$_6$)alkyl-R$_{10}$, —N(H)C(O)(C$_1$-C$_6$)alkyl-N[(C$_1$-C$_6$)alkyl]$_2$, —O—(C$_1$-C$_6$)alkyl, —NH$_2$, —N(H)(C$_1$-C$_6$)alkyl-N([C$_1$-C$_6$)alkyl]$_2$, —N(H)C(O)—(C$_1$-C$_6$)alkyl, phenyl optionally substituted with halo, —N(H)(C$_1$-C$_6$)alkyl-(C$_6$-C$_{10}$)aryl optionally substituted with halo or alkoxy at any ring position, and —N(H)(C$_1$-C$_6$)alkyl-NH$_2$;
R$_3$ is H and each of $R_9$, and $R_{10}$ are independently selected from H, —OH, halo, —CF$_3$, —O(C$_1$-C$_6$)alkyl, —(C$_6$-C$_{10}$)aryl optionally substituted with halo or alkoxy, —O—(C$_1$-C$_6$)alkyl-(C$_6$-C$_{10}$)aryl, —(C$_3$-C$_{10}$)cycloalkyl, —CN, -(5-10 membered)heteroaryl, -(4-10 membered)heterocycloalkyl, —NH$_2$, —N(H)(C$_1$-C$_6$)alkyl, and —N(H)[(C$_1$-C$_6$)alkyl]$_2$.

2. The compound according to claim 1, or a pharmaceutically acceptable salt thereof, wherein $R_2$ is indazolyl optionally substituted with 1, 2 or 3 groups independently selected from —N(H)(C$_1$-C$_6$)alkyl-N(H)C(O)—(C$_1$-C$_6$)alkyl-N[(C$_1$-C$_6$)alkyl]$_2$, —N(H)C(O)(C$_1$-C$_6$)alkyl-N[(C$_1$-C$_6$)alkyl]$_2$, —NH$_2$, —N(H)(C$_1$-C$_6$)alkyl, —N(H)C(O)—(C$_1$-C$_6$)alkyl, —(C$_1$-C$_3$)alkyl, —N(H)(C$_1$-C$_6$)alkyl-(C$_6$-C$_{10}$)aryl optionally substituted with halo or alkoxy at any ring position, and —N(H)(C$_1$-C$_6$)alkyl-NH$_2$.

3. The compound according to claim 2, or a pharmaceutically acceptable salt thereof, wherein X is O.

4. A compound according to Formula I,

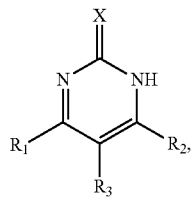

or a pharmaceutically acceptable salt thereof, wherein
X is O;
$R_1$ is phenyl ortho-substituted with —O(C$_1$-C$_6$)alkyl-R$_4$;
$R_2$ is indazolyl substituted with 1, 2 or 3 groups, which can be the same or different, selected from —N(H)(C$_1$-C$_6$)alkyl-N(H)C(O)—(C$_1$-C$_6$)alkyl-N[(C$_1$-C$_6$)alkyl]$_2$, —N(H)C(O)(C$_1$-C$_6$)alkyl-N[(C$_1$-C$_6$)alkyl]$_2$, —O—(C$_1$-C$_6$)alkyl, —NH$_2$, —N(H)(C$_1$-C$_6$)alkyl, —N(H)C(O)—(C$_1$-C$_6$)alkyl, phenyl optionally substituted with halo, —N(H)(C$_1$-C$_6$)alkyl-(C$_6$-C$_{10}$)aryl optionally substituted with halo or alkoxy at any ring position, and —NH(C$_1$-C$_6$)alkyl-NH$_2$
$R_3$ is H; and
$R_4$ is selected from H, —OH, halo, —CF$_3$, —O(C$_1$-C$_6$)alkyl, —(C$_6$-C$_{10}$)aryl optionally substituted with halo or alkoxy, —O—(C$_1$-C$_6$)alkyl-(C$_6$-C$_{10}$)aryl, —(C$_3$-C$_{10}$)cycloalkyl, —CN, -(5-10 membered)heteroaryl, -(4-10 membered)heterocycloalkyl, —NH$_2$, —N(H)(C$_1$-C$_6$)alkyl, and —N(H)[(C$_1$-C$_6$ alkyl]$_2$.

5. The compound according to claim 1, or a pharmaceutically acceptable salt thereof, wherein
X is O; and
$R_2$ is indazolyl optionally substituted with 1, 2 or 3 groups, which can be the same or different, selected from —N(H)(C$_1$-C$_6$)alkyl-N(H)C(O)—(C$_1$-C$_6$)alkyl-N[(C$_1$-C$_6$)alkyl]$_2$, —N(H)C(O)(C$_1$-C$_6$)alkyl-N[(C$_1$-C$_6$)alkyl]$_2$, —O—(C$_1$-C$_6$)alkyl, —NH$_2$, —N(H)(C$_1$-C$_6$)alkyl, —N(H)C(O)—(C$_1$-C$_6$)alkyl, phenyl optionally substituted with halo, —N(H)(C$_1$-C$_6$)alkyl-(C$_6$-C$_{10}$)aryl optionally substituted with halo or alkoxy at any ring position, and —N(H)(C$_1$-C$_6$)alkyl-NH$_2$.

6. The compound according to claim 5, or a pharmaceutically acceptable salt thereof, wherein $R_1$ is phenyl ortho-substituted with —O—CH$_2$—C(H)(CH$_3$)$_2$.

7. A compound in the form of Formula I,

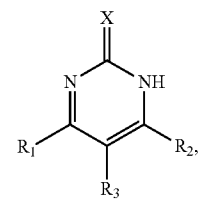

or a pharmaceutically acceptable salt thereof, wherein
X is O;
$R_1$ is phenyl substituted with —OH and —(C$_1$-C$_3$)alkyl;
$R_2$ is indazolyl optionally substituted with 1, 2 or 3 groups, which can be the same or different, selected from —N(H)(C$_1$-C$_6$)alkyl-N(H)C(O)—(C$_1$-C$_6$)alkyl-N[(C$_1$-C$_6$)alkyl]$_2$, —N(H)C(O)(C$_1$-C$_6$)alkyl-N[(C$_1$-C$_6$)alkyl]$_2$, —O—(C$_1$-C$_6$)alkyl, —NH$_2$, —N(H)(C$_1$-C$_6$)alkyl, —N(H)C(O)—(C$_1$-C$_6$)alkyl, phenyl optionally substituted with halo, —N(H)(C$_1$-C$_6$)alkyl-(C$_6$-C$_{10}$)aryl optionally substituted with halo or alkoxy at any ring position, and —N(H)(C$_1$-C$_6$)alkyl-NH$_2$; and
$R_3$ is H.

8. The compound in the form of Formula I,

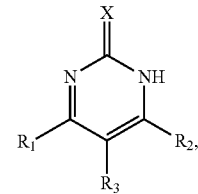

or a pharmaceutically acceptable salt thereof, wherein
X is O;
$R_1$ is phenyl substituted with —N(H)(C$_1$-C$_6$)alkyl-NH$_2$ or —N(H)(C$_1$-C$_6$)alkyl-(4-6 membered)heterocycloalkyl, and the $R_1$ phenyl group is further optionally substituted with one —(C$_1$-C$_6$)alkyl;
$R_2$ is indazolyl optionally substituted with 1, 2 or 3 groups, which can be the same or different, selected from —N(H)(C$_1$-C$_6$)alkyl-N(H)C(O)—(C$_1$-C$_6$)alkyl-N[(C$_1$-C$_6$)alkyl]$_2$, —N(H)C(O)(C$_1$-C$_6$)alkyl-N[(C$_1$-C$_6$)alkyl]$_2$, —O—(C$_1$-C$_6$)alkyl, —NH$_2$, —N(H)(C$_1$-C$_6$)alkyl, —N(H)C(O)—(C$_1$-C$_6$)alkyl, phenyl optionally substituted with halo, —N(H)(C$_1$-C$_6$)alkyl-(C$_6$-C$_{10}$)aryl optionally substituted with halo or alkoxy at any ring position, and —N(H)(C$_1$-C$_6$)alkyl-NH$_2$; and
$R_3$ is H.

9. A compound selected from:
4-(1,3-benzodioxol-5-yl)-6-{2-[(2-methylpropyl)oxy]phenyl}pyrimidin-2(1H)-one;
4-(1-benzofuran-2-yl)-6-{2-[(2-methylpropyl)oxy]phenyl}pyrimidin-2(1H)-one;
4-(3-amino-1H-indazol-5-yl)-6-{2-[(2-methylpropyl)oxy]phenyl}pyrimidin-2(1H)-one;
6-{2-[(2-methylpropyl)oxy]phenyl}-4-[3-(propylamino)-1H-indazol-5-yl]pyrimidin-2(1H)-one;
6-[5-(2-chlorophenyl)furan-2-yl]-4-{2-[(2-methylpropyl)oxy]phenyl}pyrimidin-2(1H)-one;
6-phenyl-4-[3-(propylamino)-1H-indazol-5-yl]pyrimidin-2(1H)-one;
$N^2,N^2$-dimethyl-N-[5-(6-{2-[(2-methylpropyl)oxy]phenyl}-2-oxo-1,2-dihydropyrimidin-4-yl)-1H-indazol-3-yl]glycinamide;
6-{2-[(2-methylpropyl)oxy]phenyl}-4-(5-phenylfuran-2-yl)pyrimidin-2(1H)-one;

N-[5-(6-{2-[(2-methylpropyl)oxy]phenyl}-2-oxo-1,2-dihydropyrimidin-4-yl)-1H-indazol-3-yl]propanamide;
4-{3-[(cyclopropylmethyl)amino]-1H-indazol-5-yl}-6-{2-[(2-methylpropyl)oxy]phenyl}pyrimidin-2(1H)-one;
4-(3-amino-1,2-benzisoxazol-5-yl)-6-{2-[(2-methylpropyl)oxy]phenyl}pyrimidin-2(1H)-one;
4-(3-amino-1H-indazol-5-yl)-6-[2-(propyloxy)phenyl]pyrimidin-2(1H)-one;
4-(3-{[(4-fluorophenyl)methyl]amino}-1H-indazol-5-yl)-6-{2-[(2-methylpropyl)oxy]phenyl}pyrimidin-2(1H)-one;
6-{2-[(2-methylpropyl)oxy]phenyl}-4-{3-[(piperidin-4-ylmethyl)amino]-1H-indazol-5-yl}pyrimidin-2(1H)-one;
4-{3-[(2-aminoethyl)amino]-1H-indazol-5-yl}-6-{2-[(2-methylpropyl)oxy]phenyl}pyrimidin-2(1H)-one;
4-(3-amino-1H-indazol-5-yl)-6-{2-[(cyclopropylmethyl)oxy]phenyl}pyrimidin-2(1H)-one;
$N^2,N^2$-dimethyl-N-(2-{[5-(6-{2-[(2-methylpropyl)oxy]phenyl}-2-oxo-1,2-dihydropyrimidin-4-yl)-1H-indazol-3-yl]amino}ethyl)glycinamide;
4-[3-({[3-(methyloxy)phenyl]methyl}amino)-1H-indazol-5-yl]-6-{2-[(2-methylpropyl)oxy]phenyl}pyrimidin-2(1H)-one;
4-(3-amino-1H-indazol-5-yl)-6-(2-hydroxyphenyl)pyrimidin-2(1H)-one;
4-(3-amino-1H-indazol-5-yl)-6-{2-[(trifluoromethyl)oxy]phenyl}pyrimidin-2(1H)-one;
4-[3-(methylamino)-1H-indazol-5-yl]-6-{2-[(2-methylpropyl)oxy]phenyl}pyrimidin-2(1H)-one;
6-{2-[(2-methylpropyl)oxy]phenyl}-4-{3-[(phenylmethyl)amino]-1H-indazol-5-yl}pyrimidin-2(1H)-one;
4-(3-{[(4-bromophenyl)methyl]amino}-1H-indazol-5-yl)-6-{2-[(2-methylpropyl)oxy]phenyl}pyrimidin-2(1H)-one;
4-(3-amino-1H-indazol-5-yl)-6-[3-(methyloxy)phenyl]pyrimidin-2(1H)-one;
4-(3-amino-1H-indazol-5-yl)-6-(3-isobutoxyphenyl)pyrimidin-2(1H)-one;
4-(3-amino-1H-indazol-5-yl)-6-[2-(methyloxy)phenyl]pyrimidin-2(1H)-one;
4-(3-amino-1H-indazol-5-yl)-6-{3-[(cyclohexylmethyl)oxy]phenyl}pyrimidin-2(1H)-one;
4-(3-amino-1H-indazol-5-yl)-1,5-dihydro-2H-indeno[1,2-d]pyrimidin-2-one;
4-(3-amino-1H-indazol-5-yl)-6-{2-[(piperidin-4-ylmethyl)oxy]phenyl}pyrimidin-2(1H)-one;
4-(3-amino-1H-indazol-5-yl)-6-{5-(methyloxy)-2-[(2-methylpropyl)oxy]phenyl}pyrimidin-2(1H)-one;
4-(3-amino-1H-indazol-5-yl)-6-{5-chloro-2-[(2-methylpropyl)oxy]phenyl}pyrimidin-2(1H)-one;
4-(3-amino-1H-indazol-5-yl)-6-{4-fluoro-2-[(2-methylpropyl)oxy]phenyl}pyrimidin-2(1H)-one;
4-(3-amino-1H-indazol-5-yl)-6-{5-fluoro-2-[(2-methylpropyl)oxy]phenyl}pyrimidin-2(1H)-one;
4-(3-methyl-1H-indazol-5-yl)-6-(2-{[2-(methyloxy)ethyl]oxy}phenyl)pyrimidin-2(1H)-one;
4-(1H-indazol-5-yl)-6-{2-methyl-4-[(piperidin-4-ylmethyl)amino]phenyl}pyrimidin-2(1H)-one;
4-(3-methyl-1H-indazol-5-yl)-6-{2-methyl-4-[(piperidin-4-ylmethyl)amino]phenyl}pyrimidin-2(1H)-one;
6-{4-[(2-aminoethyl)amino]-2-methylphenyl}-4-(1H-indazol-5-yl)pyrimidin-2(1H)-one;
6-{4-[(2-aminoethyl)amino]-2-methylphenyl}-4-(3-methyl-1H-indazol-5-yl)pyrimidin-2(1H)-one;
4-(3-methyl-1H-indazol-5-yl)-6-{2-[(2-methylpropyl)oxy]phenyl}pyridin-2(1H)-one;
4-(3-amino-1H-indazol-5-yl)-6-{2-[(2-methylpropyl)oxy]phenyl}pyridin-2(1H)-one;
4-(3-amino-1H-indazol-5-yl)-6-[2-(propyloxy)phenyl]pyridin-2(1H)-one;
6-{2-[(2-hydroxyethyl)oxy]phenyl}-4-(3-methyl-1H-indazol-5-yl)pyrimidin-2(1H)-one;
4-(3-amino-1H-indazol-5-yl)-6-{2-(methyloxy)-6-[(2-methylpropyl)oxy]phenyl}pyrimidin-2(1H)-one;
6-furan-3-yl-4-(4-hydroxy-3-methylphenyl)pyrimidin-2(1H)-one;
6-(4,5-dimethylfuran-2-yl)-4-(4-hydroxy-3-methylphenyl)pyrimidin-2(1H)-one;
4-(4-hydroxy-3-methylphenyl)-6-(1-methyl-1H-imidazol-2-yl)pyrimidin-2(1H)-one;
4-(4-hydroxy-3-methylphenyl)-6-(4-methyl-1,3-thiazol-5-yl)pyrimidin-2(1H)-one;
6-(1-benzofuran-2-yl)-4-(4-hydroxy-3-methylphenyl)pyrimidin-2(1H)-one;
5-[6-(2-chlorophenyl)-2-oxo-1,2-dihydropyrimidin-4-yl]-1,3-dihydro-2H-benzimidazol-2-one; and
6-(4-hydroxy-3-methylphenyl)-4-pyridin-4-ylpyrimidin-2(1H)-one,
or a pharmaceutically acceptable salt of any of the above compounds.

10. A pharmaceutical composition comprising the compound according to claim 1, 4, 7, 8, or 9, and a pharmaceutically acceptable carrier, excipient, or diluent.

* * * * *